(12) United States Patent
Askew et al.

(10) Patent No.: US 9,717,729 B2
(45) Date of Patent: Aug. 1, 2017

(54) FLUORINATED INTEGRIN ANTAGONISTS

(71) Applicant: SciFluor Life Sciences, Inc., Cambridge (MA)

(72) Inventors: Ben C. Askew, Marshfield, MA (US); Richard W. Heidebrecht, Somerville, MA (US); Takeru Furuya, Cambridge, MA (US); Mark E. Duggan, Wellesley, MA (US); D. Scott Edwards, Bedford, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 0 days.

(21) Appl. No.: 15/343,823

(22) Filed: Nov. 4, 2016

(65) Prior Publication Data

US 2017/0071939 A1    Mar. 16, 2017

Related U.S. Application Data

(63) Continuation of application No. 14/766,322, filed as application No. PCT/US2014/015372 on Feb. 7, 2014, now Pat. No. 9,518,053.

(60) Provisional application No. 61/762,087, filed on Feb. 7, 2013, provisional application No. 61/900,706, filed on Nov. 6, 2013.

(51) Int. Cl.
| | |
|---|---|
| *A61K 31/4375* | (2006.01) |
| *C07D 471/04* | (2006.01) |
| *A61K 31/506* | (2006.01) |
| *A61K 45/06* | (2006.01) |
| *A61K 31/444* | (2006.01) |
| *A61K 9/00* | (2006.01) |
| *A61K 31/4709* | (2006.01) |

(52) U.S. Cl.
CPC .......... *A61K 31/506* (2013.01); *A61K 9/0048* (2013.01); *A61K 31/4375* (2013.01); *A61K 31/444* (2013.01); *A61K 31/4709* (2013.01); *A61K 45/06* (2013.01); *C07D 471/04* (2013.01)

(58) Field of Classification Search
CPC .......................... C07D 471/04; A61K 31/4375
USPC .......................................... 546/122; 514/300
See application file for complete search history.

(56) References Cited

U.S. PATENT DOCUMENTS

| | | |
|---|---|---|
| 5,501,969 A | 3/1996 | Hastings et al. |
| 5,736,357 A | 4/1998 | Bromme et al. |
| 6,017,926 A | 1/2000 | Askew et al. |
| 6,066,648 A | 5/2000 | Duggan et al. |
| 6,211,184 B1 | 4/2001 | Duggan et al. |
| 6,268,378 B1 | 7/2001 | Duggan et al. |
| 6,291,503 B1 | 9/2001 | Schoop et al. |
| 6,297,249 B1 | 10/2001 | Duggan et al. |
| 6,407,241 B1 | 6/2002 | Jensen et al. |
| 6,410,526 B1 | 6/2002 | Duggan et al. |
| 6,426,353 B1 | 7/2002 | Arison et al. |
| 6,472,403 B2 | 10/2002 | Duggan et al. |
| 7,056,909 B2 | 6/2006 | Wang |
| 8,901,144 B2 | 12/2014 | Askew et al. |
| 9,266,884 B2 | 2/2016 | Askew et al. |
| 2001/0053853 A1 | 12/2001 | Askew et al. |
| 2002/0016461 A1 | 2/2002 | Albers et al. |
| 2002/0037889 A1 | 3/2002 | Duggan et al. |
| 2002/0040030 A1 | 4/2002 | Coleman et al. |
| 2002/0040039 A1 | 4/2002 | Hartman et al. |
| 2002/0049224 A1 | 4/2002 | Arison et al. |
| 2004/0038963 A1 | 2/2004 | Wang |
| 2004/0053968 A1 | 3/2004 | Hartman et al. |
| 2004/0249158 A1 | 12/2004 | Wells et al. |
| 2005/0004199 A1 | 1/2005 | Hartman et al. |
| 2006/0030581 A1 | 2/2006 | DeBusi |
| 2013/0129621 A1 | 5/2013 | Mackel et al. |
| 2016/0130270 A1 | 5/2016 | Askew et al. |

FOREIGN PATENT DOCUMENTS

| | | |
|---|---|---|
| CN | 1284955 A | 2/2001 |
| CN | 1589145 A | 3/2005 |
| EP | 1040098 A1 | 10/2000 |
| WO | WO 96/13523 A1 | 5/1996 |
| WO | WO 01/47867 A1 | 7/2001 |
| WO | WO 01/87840 A1 | 11/2001 |
| WO | WO 2011/060395 A1 | 5/2011 |
| WO | WO 2011/150156 A2 | 12/2011 |
| WO | WO 2013/000909 A1 | 1/2013 |

OTHER PUBLICATIONS

U.S. Appl. No. 15/380,239, filed Dec. 15, 2016, Askew et al.
Abdollahi et al., "Inhibition of $\alpha_v\beta_3$ Integrin Survival Signaling Enhances Antiangiogenic and Antitumor Effects of Radiotherapy", *Clinical Cancer Research*, 11: 6270-6279 (2005).
All Y. et al. "Industrial Perspective in Ocular Drug Delivery," *Advanced Drug Delivery Reviews*, 58:1258-1268 (2006).
Ando, M. et al., "Facile one-pot synthesis of N-difluoromethyl-2-pyridone derivatives" *Organic Letters*, 8(17):3805-3808 (2006).
Bourges, J.L. et al., "Ocular drug delivery targeting the retina and retinal pigment epithelium using polylactide nanoparticles," *Invest. Ophthalmol. Vis. Sci.*, 44:3562-3569 (2003).
Bradshaw, B. et al., "Synthesis of 5-hydroxy-2,3,4,5-tetrahydro-[1H]-2-benzazepin-4-ones: selective antagonists of muscarinic ($M_3$) receptors," *Org. Biomol. Chem.*, 6(12):2138-57 (2008).

(Continued)

*Primary Examiner* — Niloofar Rahmani
(74) *Attorney, Agent, or Firm* — Cooley LLP; Ivor R. Elrifi; Heidi A. Erlacher

(57) ABSTRACT

The present invention relates to fluorinated compounds of formula I and methods of synthesizing these compounds. The present invention also relates to pharmaceutical compositions containing the fluorinated compounds of the invention, and methods of treating macular degeneration, diabetic retinopathy (DR), macular edema, diabetic macular edema (DME), and macular edema following retinal vein occlusion (RVO), by administering these compounds and pharmaceutical compositions to subjects in need thereof.

19 Claims, 3 Drawing Sheets

(56) References Cited

OTHER PUBLICATIONS

Brinkmann et al., "Fingolimod (FTY720): discovery and development of an oral drug to treat multiple sclerosis", *Nature Reviews, Drug Discovery*, 9:883-897 (2010).
Bunz, "The Cancer Gene Theory", *Principles of Cancer Genetics*, 1:1-47 (2008).
Campochiaro, P.A., et al., "Reduction of Diabetic Macular Edema by Oral Administration of the Kinase Inhibitor PKC412," *Invest. Ophthalmol. Vis. Sci.*, 45:922-931.
Cao, F., et al. "Zn—Al—NO3-layered double hydroxides with intercalated diclofenac for ocular delivery," *International Journal of Pharmaceuticals*, 404:250-256 (2011).
Coughlin et al.," Approaches and limitations of phosphatidylinositol-3-kinase pathway activation status as a predictive biomarker in the clinical development of targeted therapy", *Breast Cancer Research Treatment*, 1-11 (2010).
Chavakis, E. et al., "Kinetics of integrin expression in the mouse model of proliferative retinopathy and success of secondary intervention with cyclic RGD peptides," *Diabetologia*, 45:262-267 (2002).
Coleman, P.J. et al. et al. "Nonpeptide $\alpha v \beta 3$ Antagonists. Part 11: Discovery and Preclinical Evaluation of potent $\alpha v \beta 3$ Antagonists for the Prevention and Treatment of Osteoporosis," *J. Med. Chem.*, 47:4829-4837 (2004).
D'Ambrosio et al., "Chemokine receptors in inflammation: an overview", *Journal of Immunological Methods*, 273:3-13 (2003).
Data from the National Cancer Institute (http://www.cancer.gov/ (Downloaded May 29, 2014).
Diebold, Y. et al., "Applications of nanoparticles in ophthalmology," *Progress in Retinal and Eye Research*, 29:596-609 (2010).
Dorrell, M., "Combination angiostatic therapy completely inhibits ocular and tumor angiogenesis," *Proceedings of the National Academy of Sciences of the United States of America*. 104(3):967-972 (2007).
Doukas, J., et al., "Topical Administration of a Multi-Targeted Kinase Inhibitor Suppresses Choroidal Neovascularization and Retinal Edema," *Journal of Cellular Physiology*, 216:29-37 (2008).
Duan et al., "Association of $\alpha_v \beta_3$ integrin expression with the metastatic potential and migratory and chemotactic ability of human osteosarcoma cells", *Clinical & Experimental Metastasis*, 21:747-753 (2004).
Felding-Habermann, "Involvement of tumor cell integrin $\alpha_v \beta_3$ in hematogenous metastasis of human melanoma cells", *Clinical & Experimental Metastasis*, 19:427-436 (2002).
Freund, K.B. et al., "Age-related Macular Degeneration and Choroidal Neovascularization," *American Journal of Ophthalmology*, 115:786-791 (1993).
Friedlander, P., *Ber. Dtsch. Chem. Ges.* 1882, 15, 2572.
Friedlander, M. et al. "Involvement of integrins $\alpha_v \beta_3$ and $\alpha_v \beta_5$ in ocular neovascular diseases". *Proc Natl Acad Sci U S A* 93:9764-9769 (1996).
Fu, Y., et al., "Angiogenesis Inhibition and Choroidal Neovascularization Suppression by Sustained Delivery of an Integrin Antagonist, EMD478761," *Invest. Ophthalmol. Vis. Sci.*, 48(11):5184-5190 (2007).
Gaudana, R. et al., "Recent perspectives in ocular drug delivery," *Pharm Res.*, 26(5):1197-1216 (2009),
Hallinan, E.A. et al., "N-Substituted dibenzoxazepine as analgesic $PGE_2$ antagonists," *J. Med. Chem.*, 36:3293-3299 (1993).
Hariharan et al., "Assessment of the biological and pharmacological effects of the $\alpha_v \beta_5$ and $\alpha_v \beta_5$ integrin receptor antagonist, cilengitide (EMD 121974), in patients with advanced solid tumors", *Annals of Oncology*, 18:1400-1407 (2006).
Haynes et al., Bone Resorption in, *Wiley Encyclopedia of Biomedical Engineering* (M. Akay ed., 2006).
Hodivala-Dilke, "$\alpha_v \beta_3$ integrin and angiogenesis: a moody integrin in a changing Environment", *Current Opinion in Cell Biology*, 20:514-519 (2008).
Hutchison, John H., et al., Nonpeptide $\alpha v \beta 3$ Antagonists. 8. In Vitro and In Vivo Evaluation of a Potent $\alpha v \beta 3$ Antagonist for the Prevention and Treatment of Osteoporosis, *J. Med. Chem.*, 46:4790-4798 (2003).
Hynes, "Integrins: Bidirectional, Allosteric Signaling Machines", *Cell*, 110:673-687 (2002).
Jacot, J.L. et al., "Potential Therapeutic Roles for Inhibition of the P13K/Akt/mTOR Pathway in the Pathophysiology of Diabetic Retinopathy," *Journal of Ophthalmology*, vol. 2011, Article ID 589813 (2011).
Jubb et al., "Predicting benefit from antiangiogenic agents in malignancy", *Nature Reviews/Cancer*, 6: 626-635 (2006).
Judge et al., "Potassium channel blockers in multiple sclerosis: Neuronal Kv channels and effects of symptomatic treatment", *Pharmacology & Therapeutics*, 111 :224-259 (2006).
Kamizuru, H.K.H. et al., "Monoclonal antibody-mediated drug targeting to choroidal neovascularization in the Rat.," *Investigative Opthalmology & Visual Science*, 42:2664-2672 (2001).
Kaur, H., et al., "Niosomes: A Novel Drug Delivery System," *Int J Pharm Sci Rev Res*, 15(1):113-120 (2012).
Kern, T.S., et al., "Topical administration of nepafenac inhibits diabetes-induced retinal microvascular disease and underlying abnormalities of retinal metabolism and physiology," *Diabetes*, 56(2):373-379 (2007).
Klein, R. et al., "The Wisconsin Epidemiologic Study of diabetic retinopathy. XIV. Ten-year incidence and progression of diabetic retinopathy," *Arch Ophthalmol*, 12:1217-1228 (1994).
Koelink et al., "Targeting chemokine receptors in chronic inflammatory diseases: An extensive review", *Pharmacology & Therapeutics*, 133 :1-18 (2012).
Kuppen et al., "Tumor structure and extracellular matrix as a possible barrier for therapeutic approaches using immune cells or adenoviruses in colorectal cancer", *Histochemistry and Cell Biology*, 115:67-72 (2001).
Linderman, R.J., "Oxidation of Fluoroalkyl-Substituted Carbinols by the Dess-Martin Reagent," *J. Org. Chem.*, 54(3):661-668 (1989).
Lissoni et al, "Biotherapy with the pineal hormone melatonin plus aloe and myrrh tincture in untreatable metastatic cancer patients as an essence therapy of cancer", *Cancer Research*, 7:397-401 (2009).
Lorger et al., Activation of tumor cell integrin $\alpha_v \beta_3$ controls angiogenesis and metastatic growth in the brain, *PNAS*, 106:10666-10671 (2009).
Luna, J. et al. "Antagonists of Integrin $\alpha v \beta 3$ Inhibit Retinal Neovascularization in a Murine Model," *Laboratory Investigation*, 75(4):563-573 (1996).
Luo et al., "Principles of Cancer Therapy: Oncogene and Non-oncogene Addiction",*Cell*, 136: 823-837 (2009).
Lyons et al., "Integrins in metastatic adenoid cystic carcinoma", *International Journal of Oral and Maxillofacial Surgery*, 34 :912-914 (2005).
Marelli et al., "Tumor targeting via integrin ligands", *Frontiers in Oncology*, 3:1-12 (2013).
Max et al., "Immunohistochemical Analysis of Integrin $A_v B_3$ Expression on Tumor-Associated Vessels of Human Carcinomas", *International Journal of Cancer*, 71:320-324 (1997).
McDermott et al., "Personalized Cancer Therapy With Selective Kinase Inhibitors: An Emerging Paradigm in Medical Oncology", *Journal of Clinical Oncology*, 27:5650-5659 (2009).
Meissner, R.S. et al., "Nonpeptide $\alpha_v \beta_3$ Antagonists. Part 2: Constrained Glycyl Amides Derived from the RGD Tripeptide", *Bioorganic & Medicinal Chemistry Letters*, 12:25-29 (2002).
Millauer, B., et al., "Dominant-Negative Inhibition of Flk-1 Suppresses the Growth of Many Tumor Types in Vivo", *Cancer Research*, 56:1615-1620 (1996).
Moors et al. Journal of Medicinal Chemistry (2011 ), 54(17), 6098-6105.
Mousa, "Cell Adhesion Molecules: Potential Therapeutic & Diagnostic Implications", *Molecular Biotechnology*, 38:33-40 (2008).
Muller et al., Antiviral Strategies in, *Antiviral Strategies* 1-24, 4 (H.-G. Krausslich et al., eds., 2009).
Murphy, M.G., et al., "Effect of L-000845704, an $\alpha v \beta 3$ Integrin Antagonist, on Markers of Bone Turnover and Bone Mineral

(56) References Cited

OTHER PUBLICATIONS

Density in Postmenopausal Osteoporotic Women," *The Journal of Clinical Endocrinology & Metabolism*, 90(4):2022-2028 (2005).
Nahm, S., et al., "N-methoxy-n-methyl amides as effective acylating agents," *Tetrahedron Letters*, 22(39):3815-3818(1981).
Pialat, A. et al., "Oxidative para-Triflation of Acetanilides," *Organic Letters*, 15:1764-1767 (2013).
Prasasya et al., "Analysis of cancer signaling networks by systems biology to develop therapies", *Seminars in Cancer Biology*, 21: 200-206 (2011).
Rabinow, Barrett E., "Nanosuspensions in Drug delivery," *Nature Reviews Drug Discovery*, 3:785-796 (2004).
Reinmuth et al., "$\alpha_v\beta_3$ Integrin Antagonist S247 Decreases Colon Cancer Metastasis and Angiogenesis and Improves Survival in Mice", *Cancer Research*, 63:2079-2087 (2003).
Riecke, B. et al. "Topical Application of Integrin Antagonists Inhibit Proliferative Retinopathy," *Horm Metab Res*, 33:307-311 (2001).
Rolli et al., "Activated integrin $\alpha_v\beta_3$ cooperates with metalloproteinase MMP-9 in regulating migration of metastatic breast cancer cells", *PNAS*, 100:9482-9487 (2003).
Rowe, Raymond C., "Handbook of Pharmaceutical Excipients", Fifth Edition, Pharmaceutical Press and American Pharmacists Association (2006).
Santulli, R. et al., "Studies with an Orally Bioavailable αv Integrin Antagonist in Animal Models of Ocular Vasculopathy: Retinal Neovascularization in Mice and Retinal Vascular Permeability in Diabetic Rats," *The Journal of Pharmacology and Experimental Therapeutics*, 324:894-90 (2008).
Santulli et al., "Evaluation of the anti-angiogenic properties of the new selective $\alpha_v\beta_3$ integrin antagonist RGDechiHCit", *Journal of Translational Medicine*, 9:1-10 (2011).
Sato, I. et al., "Enantioselective Synthesis of Substituted 3-Quinolyl Alkanols and Their Application to Asymmetric Autocatalysis," *Synthesis*, 9:1419-1428 (2004).
Sawyers, "The Cancer Biomarker Problem", Nature, 548-552 (2008).
Seebach, D. et al., "Total Synthesis of Myxovirescin, 1 Strategy and Construction of the Southeastern Part [O(1)—C(14)]", *Liebigs Ann. Chem.*, pp. 701-717 (1994).
Sondej, S.C. et al., "Gem-Difluoro Compounds: A Convenient Preparation from Ketones and Aldehydes by Halogen Fluoride Treatment of 1,3-dithiolanes," *J. Org. Chem.*, 51:3508-3513 (1986).
Soussi, "p53 Antibodies in the Sera of Patients with Various Types of Cancer: A Review", *Cancer Research*, 60:1777-1788 (2000).
Speicher, M.A. et al. "Pharmacologic therapy for diabetic retinopathy," *Expert Opin Emerging Drugs*, 8(1):239-250 (2003).
Stragies, R. et al. "Design and Synthesis of a New Class of Selective Integrin $\alpha5\beta1$ antagonists", *J. Med. Chem.*, 50:3786-3794 (2007).
Stupp et al., "Integrin Inhibitors Reaching the Clinic", *Journal of Clinical Oncology*, 25:1637-1638 (2007).
Sutherland et al., "Management of Chronic Obstructive Pulmonary Disease", *The New England Journal of Medicine*, 350:2689-2697 (2004).
Takagi, H. et al., "Role of Vitronectin Receptor-Type Integrins and Osteopontin in Ischemia-Induced Retinal Neovascularization," *Japanese Opthalmological Society*, 46:270-278 (2002).
Takahashi, K et al. "Suppression and Regression of Choroidal Neovascularization by the Multitargeted Kinase Inhibitor Pazopanib," *Arch. Ophthalmol.*, 127(4): 494-499 (2009).
Takayama et al., "The Relationship Between Bone Metastasis from Human Breast Cancer and Integrin $\alpha_v\beta_3$ Expression", Anticancer Research, 25 :79-84 (2005).
Vandamme, Th.F., "Microemulsions as ocular drug delivery systems: recent developments and future challenges," *Progress in Retinal and Eye Research*, 21:15-34 (2002).
Wagh, V.D. et al. "Niosomes as ophthalmic drug delivery systems: a review," *Journal of Pharmacy Research*, 3(7):1558-1563 (2010).
Wang, W. et al. "The Antiangiogenic Effects of Integrin $\alpha5\beta1$ Inhibitor (ATN-161) In Vitro and In Vivo," *Invest. Ophthalmol. Vis. Sci.*, 52(10):7213-7220 (2011), Published online before print Aug. 3, 2011.
Wang et al., "Mathematical modeling in cancer drug discovery", *Drug Discovery Today*, 19: 145-150 (2014).
Ward et al., "Inflammation and $\alpha_v\beta_3$ Integrin", *American Journal of Respiratory and Critical Care Medicine*, 185:5-6 (2012).
Williams, R. et al. "Epidemiology of diabetic retinopathy and madular oedema: a review," *Eye*, 18:963-983 (2004).
Yang, X.M., "Role of PI3K/Akt and MEK/ERK in Mediating Hypoxia-Induced Expression of HIF-1α and VEGF in Laser-Induced Rat Choroidal Neovascularization," *Investigative Ophthalmology & Visual Science*, 50(4):1873-1879 (2009).
Yanni, S.E. et al., "The effects of nepafenac and amfenac on retinal angiogenesis," Elsevier, *Brain Research Bulletin*, 81:310-319 (2010).
Yasuda, N., et al., "An Efficient Synthesis of an αvβ3 Antagonist," *J. Org. Chem.*, 69:1959-1966 (2004).
Yasukawa, T, et al. "Inhibition of experimental choroidal neovascularization in rats by an $\alpha_v$-integrin antagonist," *Current Eye Research*, 28(5):359-366 (2004).
Zarbin, M.A. "Current Concepts in the Pathogenesis of Age-Related Macular Degeneration", *Arch. Ophthalmol.*, 122:598-614 (2004).
Zhao et al., Journal of Physical Chemistry B (2009), 113(17), 5929-5937.
Zhou, Hong-Yon et al., "Nanoparticles in the ocular drug delivery," *Int. J. Ophthalmol*, 6(3):390-396 (2013).

A

B

C

FLUORINATED INTEGRIN ANTAGONISTS

CROSS-REFERENCE TO RELATED APPLICATIONS

This application is a continuation of U.S. Ser. No. 14/766,322, filed on Aug. 6, 2015 (now allowed), which is a U.S. National Phase application of International Application No. PCT/US2014/015372, filed on Feb. 7, 2014, which claims priority to and the benefit of U.S. Ser. No. 61/762,087, filed on Feb. 7, 2013, and U.S. Ser. No. 61/900,706, filed on Nov. 6, 2013, the contents of each of which are incorporated herein by reference in their entireties.

BACKGROUND OF THE INVENTION

Age-related macular degeneration (AMD) is the leading cause of blindness in people over the age of 55; and diabetic retinopathy (DR) is the leading cause in people under 55 (Klein, 1994; Williams, 2004). Both diseases are characterized by new blood vessel growth—choriodal neovascularization in AMD and retinal neovascularization in DR (Freund, 1993; Speicher, 2003; Zarbin, 2004). Macular edema occurs when fluid and protein deposits collect on or under the macula of the eye (a yellow central area of the retina) and cause it to thicken and swell (edema). Diabetic macular edema (DME) is similarly caused by leaking macular capillaries. DME is the most common cause of visual loss in both proliferative and non-proliferative DR. Thrombosis of central retinal vein (CRV) and its branches is the second most prevalent vascular pathology after DR, and results in abrupt decrease in visual acuity and is accompanied by macular edema. Thus, anti-angiogenesis treatments are useful in combating all these conditions.

αv integrins have been shown to be involved in ocular angiogenesis. Expression of αv integrins is upregulated in various diseases or conditions, such as AMD and DR, and in mouse model of oxygen-induced retinopathy (OIR) or retinopathy of prematurity (ROP) model (Takagi, 2002). Also, αvβ3 is expressed in new vessels after photocoagulation, but not in normal choroidal vessels, in the laser-induced choroidal neovascularization model for AMD (Kamizuru, 2001). Administration of αv integrins antagonists, such as a cyclic RGD peptide, has been shown to inhibit retinal and choroidal neovascularization (Friedlander, 1996; Chavakis, 2002; Luna, 1996; Riecke, 2001; Yasukawa, 2004).

Angiogenesis inhibitors targeting vascular endothelial growth factor (VEGF), other growth factors (e.g., fibroblast growth factor (FGF), platelet-derived growth factor (PDGF)), chemokines (e.g., IL8, SDF1, G-CSF), receptors (e.g., CXCR1, FGF-R, PLGFR, PDGFR, Tie-receptors), intracellular mediators (e.g., c-kit kinase, PI3 kinase, PKC), and extracellular mediators (e.g., integrins, cadherins), as well as inhibitors of pro-angiogenic targets (e.g., phosphoinositide 3 kinase), have been investigated for the treatment of AMD and DR. However, application of these drugs is limited due to various concerns, such as toxicity and complexity of administration. Further, αv integrins inhibitors tested or currently in clinical trials for treating AMD and DR are not being successfully developed due to poor ocular pharmacokinetics and/or high levels of excipient/carrier (e.g., benzalconium chloride and mannitol) known to cause damage to the eye.

Thus, there continues to be a need for improved compounds, compositions, and methods for treating AMD, DR, DME, and macular edema following retinal vein occlusion, that are safe, effective, and conveniently administered. The present invention addresses the need.

SUMMARY OF THE INVENTION

The present invention provides novel fluorinated compounds which are αv integrin antagonists, having formula I:

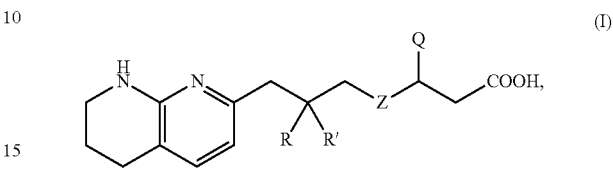

or a pharmaceutically acceptable salt or solvate thereof.

The present invention provides a pharmaceutical composition comprising a compound of the invention or a pharmaceutically acceptable salt or solvate thereof, and a pharmaceutically acceptable carrier or excipient.

The present invention also provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tie-1, and f) an inhibitor of phosphoinositide 3-kinase, and a mixture thereof.

The present invention further provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factors, d) an inhibitor of VEGF, and e) an inhibitor of phosphoinositide 3-kinase, and a mixture thereof.

The present invention provides a method of treating or preventing a disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the invention provides treating a disease or condition. In one aspect, the invention provides preventing a disease or condition. In one aspect, the compound or pharmaceutical composition of the invention is administered topically.

The present invention provides a method of treating or preventing a disease or condition mediated by an αv integrin in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the disease or condition is a disease or condition in which angiogenesis is involved. In a further aspect, the disease or condition is a disease or condition in which ocular angiogenesis is involved.

The present invention also provides a method of treating or preventing an αvβ3 and/or αvβ5 integrin-mediated disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO).

The present invention further provides a method of treating or preventing AMD, DR, DME, or macular edema following RVO, comprising administering to a subject in need thereof, a therapeutically effective amount of a compound of the invention or a pharmaceutically acceptable salt or solvate thereof or a therapeutically effective amount of a pharmaceutical composition of the invention. In one aspect, the invention provides treating AMD, DR, DME, or macular edema following RVO. In one aspect, the invention provides preventing AMD, DR, DME, or macular edema following RVO.

The present invention further provides a method of treating or preventing a disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention, in combination with one or more therapies for treating or preventing the disease or condition. In one aspect, the disease or condition is mediated by an αv integrin. In a further aspect, the disease or condition is mediated by an αvβ3 and/or αvβ5 integrin. In one aspect, the disease or condition is a disease or condition in which angiogenesis is involved. In a further aspect, the disease or condition is a disease or condition in which ocular angiogenesis is involved. In one aspect, the therapy is an anti-VEGF therapy. In a further aspect, the anti-VEGF therapy is intravitreally injected.

The present invention provides the use of a compound of the invention or a pharmaceutically acceptable salt or solvate thereof in treating or preventing a disease or condition in a subject. In one aspect, the use is for treating a disease or condition. In one aspect, the use is for preventing a disease or condition. In one aspect, the compound or pharmaceutical composition of the invention is formulated for use in topical administration.

The present invention provides the use of a compound of the invention or a pharmaceutically acceptable salt or solvate thereof in the manufacture of a medicament for the treatment or prevention of a disease or condition in a subject. In one aspect, the invention provides for the treatment of a disease or condition. In one aspect, the invention provides for the prevention of a disease or condition. In one aspect, the medicament is formulated for topical administration.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
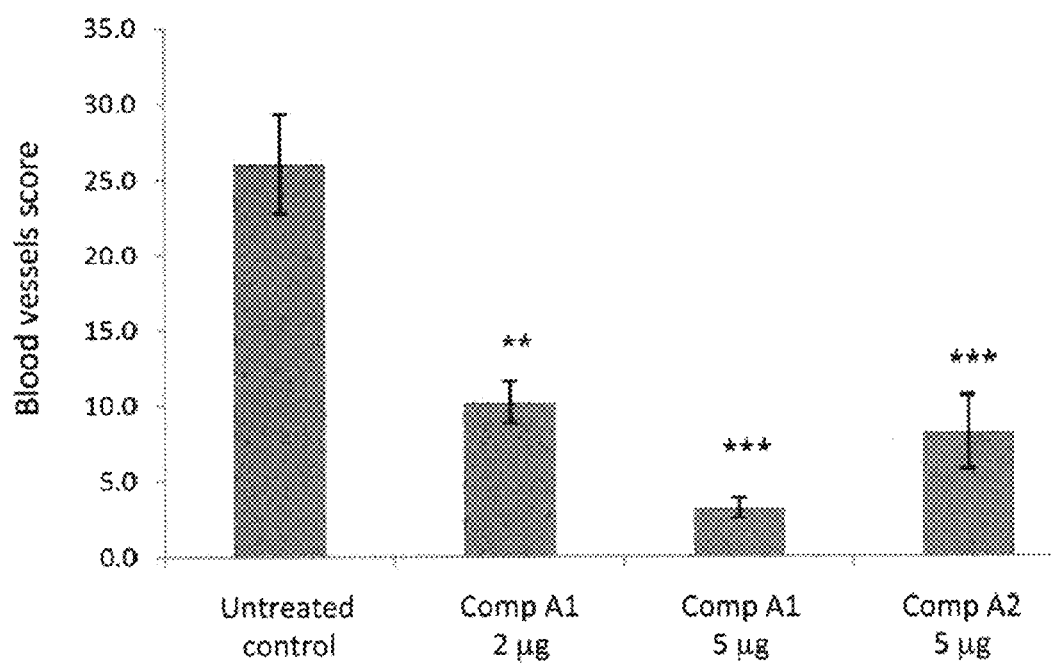
FIG. 1. A bar graph showing blood vessel counts (score) in the chick CAM assay FIG. 2. A bar graph showing plasma and ocular distribution of Compound A1 in rabbit FIG. 3. A bar graph showing plasma and ocular distribution of Compound A2 in rabbit FIG. 4. A bar graph showing plasma and ocular distribution of Compound A3 in rabbit FIG. 5. Representative Fluorescein Angiography (FA) images of the eye on day 35 in animals following twice daily topical administration of (A) 50 μL Compound A1, (B) 50 μL Compound A2, (C) 50 μL vehicle

It is believed that a wide variety of diseases and conditions can be treated or prevented by inhibiting processes mediated by αv integrins. Thus, αv integrin antagonists represent a useful class of drugs for treating or preventing those diseases and conditions. Integrins are heterodimeric transmembrane proteins through which cells attach and communicate with extracellular matrices and other cells. The αv integrins are key receptors involved in mediating cell migration and angiogenesis. Antagonists of the integrins αvβ3 and αvβ5 are useful for treating and preventing bone resorption, osteoporosis, vascular restenosis, diabetic retinopathy, macular degeneration, angiogenesis, atherosclerosis, inflammation, viral disease, tumor growth, and metastasis.

αv integrins have also been found to be involved in ocular angiogenesis, a process that can lead to various ocular diseases, such as age-related macular degeneration (AMD), diabetic retinopathy (DR), diabetic macular edema (DME), and macular edema following retinal vein occlusion (RVO) (Freund, 1993; Speicher, 2003; Zarbin, 2004). Pro-angiogenic growth factors, including VEGF and FGF, are up-regulated in AMD and DR, which, in turn, stimulate αv integrin expression. In the well-established mouse model of oxygen-induced retinopathy (OIR) or retinopathy of prematurity (ROP) model, αv integrins and the ligand osteopontin are overexpressed in neovascular endothelial cells during the peak time of retinal vessel growth (Takagi, 2002). Cyclic peptides mimicking the arginine-glycine-asparagine (RGD) binding motif, through which αv integrins bind to their extracellular matrix ligands, have been shown to inhibit retinal neo-vascularization in the mouse OIR model via various routes of administration (e.g., subcutaneous, intraperitoneal, periocular, or topical) (Friedlander, 1996; Chavakis, 2002; Luna, 1996; Riecke, 2001). Also, in the laser-induced choroidal neovascularization model (rats), a well-accepted model for AMD, integrins αvβ3 and von Willebrand factor are expressed on endothelial cells of new vessels after photocoagulation, but not in normal choroidal vessels (Kamizuru, 2001). In this model, intravitreal injection of a cyclic RGD peptide significantly reduces the development of choroidal neovascularization (Yasukawa, 2004). In humans, expression of αvβ3 and αvβ5, which are not expressed in normal retinal tissue, is observed in vascular cells in the eyes of DR patients (Friedlander, 1996; Luna, 1996), and high levels of αvβ5 expression is primarily observed in ocular tissues in AMD patients (Friedlander, 1996).

Diseases or conditions of the retina (which is located at the back of the eye), including macular degeneration, DR, DME, and macular edema following RVO, are very difficult to treat by systemic administration (e.g., oral, intravenous, intra-nasally, or inhalation) because the retina is difficult to access from the systemic circulation due to the blood-retinal barrier. Therefore, currently approved treatments (e.g., anti-VEGF proteins or a chemically-modified anti-VEGF aptamer) for macular degeneration, DME, and macular edema following RVO must be repeatedly administered by intra-ocular injection (intravitreal administration).

Many angiogenesis inhibitors targeting vascular endothelial growth factor (VEGF) (e.g., the VEGF aptamer, pegaptanib, and the VEGF or VEGF receptor (VEGFR)-targeted monoclonal antibodies, bevacizumab, ranibizumab, aflibercept) have been investigated for the treatment of AMD and DR. However, only pegatanib, ranibizumab, aflibercept are approved by the Food and Drug Administration. Further, all the VEGF-targeted drugs must be administered by intravitreal injection to treat AMD or DR. Intravitreal injection requires adequate anesthesia and a broad-spectrum microbicide, and the insertion of a syringe needle into the eye using aseptic conditions, thus necessitating the administration to be performed in a physician's office. For example, the dosage and administration section of the ranibizumab Package Insert describes the complex requirements for administering the drug in a safe and effective manner: all of the ranibizumab vial contents are withdrawn through a 5-micron, 19-gauge filter needle attached to a 1-cc tuberculin syringe under aseptic technique; the filter needle should be discarded after withdrawal of the vial contents and should be replaced with a sterile 30-gauge×½-inch needle for the intravitreal injection; the contents should be expelled until the plunger tip is aligned with the line that marks 0.05 mL on the syringe; the intravitreal injection procedure should be carried out under controlled aseptic conditions (e.g., using sterile gloves, a sterile drape, and a sterile eyelid speculum).

In addition to the practical limitations and strictures related to the need for intravitreal injection in the treatment of ocular diseases, VEGF-targeted drugs only address VEGF-promoted angiogenesis, but not angiogenesis promoted by other growth factors, including fibroblast growth factor (FGF), and platelet-derived growth factor (PDGF). Targeting angiogenic molecules other than, or in addition to VEGF, may reveal more effective and safer inhibitors of intraocular neovascularisation. Potential targets include growth factors (e.g., angiopoietin, FGF, HGF, IGF-1, PDGF-B, PLGF), chemokines (e.g., IL8, SDF1, G-CSF), receptors (e.g., CXCR1, FGF-R, PLGFR, PDGFR, Tie-receptors), intracellular mediators (e.g., c-kit kinase, PI3 kinase, PKC), and extracellular mediators (e.g., integrins, cadherins). Several drugs which do not selectively target VEGF have indeed shown anti-angiogenic efficacy in eyes: Pazopanib (which blocks PDGFRs, c-Kit, FGFR, and c-fms) suppresses choroidal neovascularization in mouse models; and PKC412 (which blocks PKC, VEGF-R, PDGF-R and SCF-R isoforms) reduces macular oedema in diabetics (Doukas, 2008; Takahashi, 2009; Campochiara, 2004). Treatments that combine the action of the VEGF-targeted therapies with inhibition of one of these other growth factors have also been studied. For example, a Phase 3 clinical trial is underway testing the combination of ranibizumab and the anti-PDGF antibody designed E10030 (ClinTrials.gov, NCT01944839). However, these therapies are limited by safety concerns and complexity of administration, such as liver toxicity observed following oral administration of PKC412, and intravitreal administration of ranibizumab and E10030.

Another approach for treating or preventing ocular diseases is to selectively target a distinct pro-angiogenic target, such as PI3K. A broad-spectrum PI3K inhibitor LY294002 suppresses retinal or choroidal neovascularisation following intraocular injection in rodents (Yang, 2009). Additional alternative treatments for AMD and DR involving intravitreal administration of several small molecule inhibitors which prevent angiogenesis (e.g., fibronectin receptor antagonists, JSM6427 (Clin Trials.gov, NCT00536016) and ATN-161 (Wang, 2011), vascular endothelial protein tyrosine phosphatase inhibitors (ClinTrials.gov, NCT01702441), and mTOR inhibitors, sirolimus, and Palomar 529 (Jacot, 2011)) are being tested in animals or in clinical trials. Further, combination therapies involving multiple foci of pro-angiogenic pathways with several selective inhibitors (e.g., combining angiostatic therapy with a VEGF aptamer, an integrin antagonist, and a proteolytic fragment of tryptophan tRNA synthetase) have been shown to inhibit ocular angiogenesis (Dorrell, 2007). Despite these studies and clinical trials, no therapy with a favorable efficacy and safety profile has been reported.

Recent advances in drug delivery technology, including formulation, polymer chemistry, nanotechnology, microdrug devices, and surgical advancements, have offered new options and opportunities for topical ocular drug administration. These technologies include the use of hydrogels, mucoadhesive polymers, cyclodextrins, nanocomposite formulations, micellar and lipid nanoparticles, niosomes, microemulsion, microspheres, and prodrug derivatization. For instance, nanocomposites have been used to deliver Diclofenac (Cao, 2011), and topical administration of Nepafenac has been shown to reduce the extent of microangiopathy in animal models of DR (Kern, 2007) and oxygen-induced retinopathy (Yanni, 2010). Also, nanoparticle technology has been employed to enhance the surface penetration of hydrophobic compounds such as glucocorticoids to posterior ocular structures (Diebold, 2010), and injection of nanoparticles into the vitreous has demonstrated intraretinal localization for several months after initial dosing and therefore can be used as a localized drug release depot (Bourges, 2003). Topical administration using eye drops (e.g., eye drop formulation comprising TG100572, which inhibits FGF, PDGF and VEGF (Doukas, 2008), or tyrosine kinase inhibitors (TKIs) (e.g., sorafenib (WO2013/000909), bradykinin receptor antagonists (ClinTrials.gov, NCT01319487), or an anti-microbial agent, squalamine (ClinTrials.gov, NCT01678963)) has been studied or is under investigation. However, none of these approaches have been shown to be suitable for replacing the current standard anti-VEGF treatments that require intravitreal injection.

Oral or topical administration of drugs that inhibit αv integrins (e.g., cyclic penta-peptide inhibitor of αvβ3 and αvβ5, cyclo-RGDfV, cilengetide, and the non-peptide αvβ3 and αvβ5 antagonist, JNJ-26076713 and EMD478761), for example, by means of a polyvinyl alcohol-based reservoir implant, has been tested or is currently in clinical trials for treating AMD and DR (Friedlander, 1996; Santulli, 2008; Fu, 2007). Cyclo-RGDfV was also tested in a mouse model of retinopathy of prematurity administered by topical administration (Riecke, 2000); however, the compound needed to be administered six times a day, due to the poor ocular pharmacokinetics of the compound (i.e., the amount of the compound that distributes to the retina after administration as eye drops, and then maintains an adequate retinal concentration between administrations). In addition, the peptide was formulated with high levels of benzalconium chloride and mannitol, which are known to cause damage to the eye. As a result, topical administration has not been successfully developed. To date, the most recent approach to treating ocular angiogenesis is through intravitreal injection of ALG-1001 (a synthetic oligo-peptide inhibitor of $\alpha v\beta 3$, $\alpha v\beta 5$, and $\alpha 5\beta 1$), which cannot be administered topically.

The present invention relates to novel fluorinated compounds, which are antagonists of the $\alpha v$ integrins, particularly integrins $\alpha v\beta 3$ and/or $\alpha v\beta 5$. The compounds of the present invention or pharmaceutically acceptable salts or solvates thereof are useful in treating or preventing bone resorption, osteoporosis, vascular restenosis, atherosclerosis, inflammation, viral disease, tumor growth, or metastasis. In particular, the compounds of the present invention or pharmaceutically acceptable salts or solvates thereof and pharmaceutical composition comprising the compounds are effective in treating macular degeneration, DR, DME, and macular edema following retinal vein occlusion (RVO) when administered topically.

Prior attempts to use small molecule integrin antagonists by topical administration have not succeeded because those compounds lack the appropriate physiochemical properties (e.g., lipophilicity, molecular size and polar surface area) to allow delivery of therapeutically effective amounts of those compounds by a convenient formulation and dosing regimen. The compounds of the present invention have been surprisingly shown to distribute to the retina after topical administration in therapeutically effective amounts to inhibit the function of integrins $\alpha v\beta 3$ and $\alpha v\beta 5$ and thus treat or prevent retinal angiogenesis. The compounds of the present invention have advantages such as providing improved potency, selectivity, tissue penetration, half-life, and/or metabolic stability, and successful distribution to the retina in therapeutically effective amounts via convenient topical administration to the eyes.

Compounds of the Invention

The present invention relates to novel fluorinated compounds of formula I:

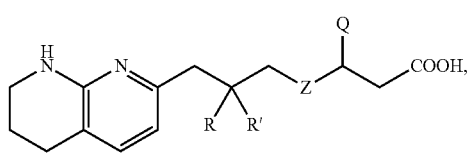

(I)

or a pharmaceutically acceptable salt or solvate thereof, wherein:
  Z is

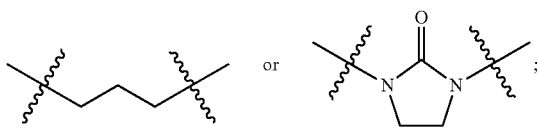 [SMILES: *CCC* ; *N1CCN(*)C1=O]

R and R' are each independently H or F, or R and R', together with the carbon atom to which they are attached, form a 3- or 4-membered carbocyclic or heterocyclic ring;
  Q is

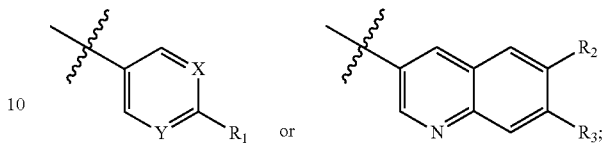

X is CH or N;
Y is CH or N;
$R_1$ is $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms; and
$R_2$ and $R_3$ are each independently H, F, $CH_2F$, $CHF_2$, or $CF_3$, provided that one of $R_2$ and $R_3$ is not H, provided that the compound of formula (I) contains at least one fluorine atom.

The compounds of the present invention contain at least one fluorine atom. In one aspect, the compounds of the present invention contain at least one fluorine atom in the R or R' substituent. In another aspect, the compounds of the present invention contain at least one fluorine atom in the $R_1$ substituent. In another aspect, the compounds of the present invention contain at least one fluorine atom in the $R_2$ or $R_3$ substituent. Fluorination at any particular position, such as that present in the compounds of the invention, has not been taught or suggested.

In one aspect, Z is

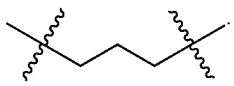

In another aspect, Z is

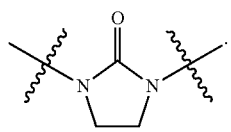

In one aspect, R and R' are each H. In another aspect, R and R' are each F. In another aspect, R is H and R' is F.

In another aspect, R and R', together with the carbon atom to which they are attached, form a 3- or 4-membered carbocyclic or heterocyclic ring. In a further aspect, R and R', together with the carbon atom to which they are attached, form a 4-membered heterocyclic ring. In a further embodiment, the 4-membered heterocyclic ring is an oxetane ring. For example, the oxetane ring is an oxetan-3-yl ring or oxetan-2-yl ring.

In one aspect, Q is

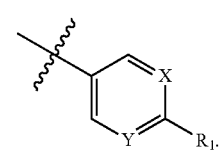

In one aspect, X is N and Y is CH. In another aspect, X and Y are each CH. In another aspect, X and Y are each N.

In one aspect, $R_1$ is straight chain $C_1$-$C_4$ or branched $C_3$-$C_4$ alkyl, and is substituted with 1, 2, 3, 4, 5, 6, 7, 8, or 9 fluorine atoms. In a further aspect, $R_1$ is methyl, ethyl, propyl, or butyl, and is substituted with 1, 2, 3, 4, 5, 6, 7, 8, or 9 fluorine atoms. In a further aspect, $R_1$ is methyl substituted with 1, 2, or 3 fluorine atoms. In a further aspect, $R_1$ is $CF_3$.

In another aspect, $R_1$ is straight chain $C_1$-$C_6$ or branched $C_3$-$C_6$ alkoxy, and is substituted with 0, 1, 2, 3, 4, 5, 6, or 7 fluorine atoms. In a further aspect, $R_1$ is methoxy, ethoxy, propoxy, or butoxy, and is substituted with 0, 1, 2, 3, 4, 5, 6, or 7 fluorine atoms. In a further aspect, $R_1$ is methoxy substituted with 0, 1, 2, or 3 fluorine atoms. In a further aspect, $R_1$ is $OCH_3$, $OCH_2F$, $OCHF_2$, or $OCF_3$. In a further aspect, $R_1$ is $OCHF_2$.

In another aspect, Q is

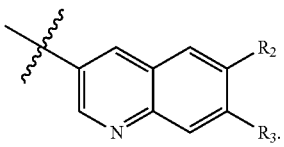

In one aspect, $R_2$ is F. In a further aspect, $R_2$ is F and $R_3$ is H. In another aspect, $R_2$ is $CH_2F$, $CHF_2$, or $CF_3$.

In one aspect, $R_3$ is F. In a further aspect, $R_3$ is F and $R_2$ is H. In another aspect, $R_3$ is $CH_2F$, $CHF_2$, or $CF_3$. In a further aspect, $R_3$ is $CF_3$. In a further aspect, $R_3$ is $CF_3$ and $R_2$ is H.

In one aspect, $R_2$ and $R_3$ are each F.

In one aspect, Z is

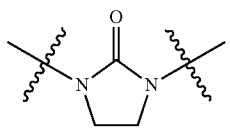

and Q is

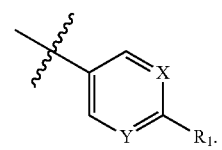

In a further aspect, Z is

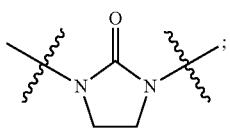

Q is

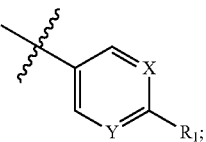

and R and R' are each H.

In a further aspect, Z is

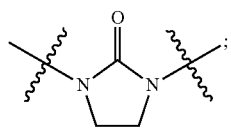

Q is

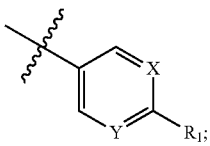

R and R' are each H; and $R_1$ is $OCH_3$, $OCH_2F$, $OCHF_2$, or $OCF_3$. In a further aspect, X is N and Y is CH; and $R_1$ is $OCHF_2$.

In one aspect, Z is

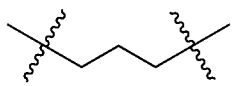

and Q is

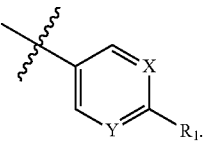

In one aspect, Z is

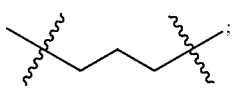

and Q is

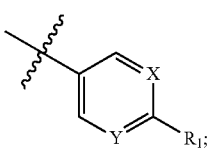

and X and Y are each N. In a further aspect, $R_1$ is methyl substituted with 1, 2, or 3 fluorine atoms. In a further aspect, $R_1$ is $CF_3$.

In another further aspect, Z is

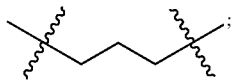

Q is

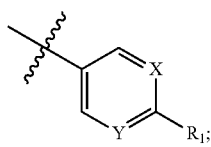

and X is N and Y is CH.

In a further aspect, $R_1$ is $OCH_3$, $OCH_2F$, $OCHF_2$, or $OCF_3$. In a further aspect, $R_1$ is $OCHF_2$.

In one aspect, Z is

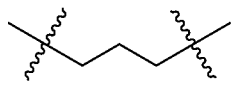 [SMILES: *CCC*]

and Q is

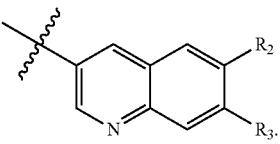

In one aspect, a compound of present invention is of formula II:

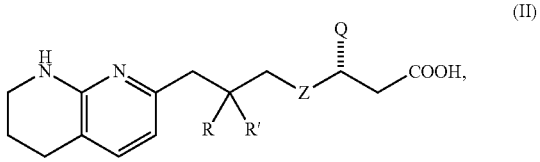

(II)

or a pharmaceutically acceptable salt or solvate thereof, wherein each of the variables are as defined above. Compounds of the present invention include compounds of formula II, wherein the variables are illustrated in the various aspects of formula I above.

Representative compounds of the present invention include the compounds listed in Table 1.

TABLE 1

| Cmpd # | Chemical Structure |
|---|---|
| A1 | ![structure A1] |
| A2 | ![structure A2] |
| A3 | ![structure A3] |

TABLE 1-continued

| Cmpd # | Chemical Structure |
|---|---|
| A4 | 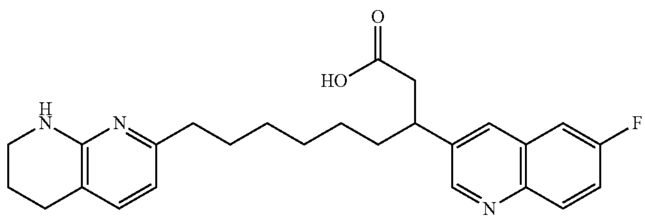 [SMILES: O=C(O)CC(CCCCCCc1ccc2c(n1)NCCC2)c1cnc2ccc(F)cc2c1] |
| A5 | 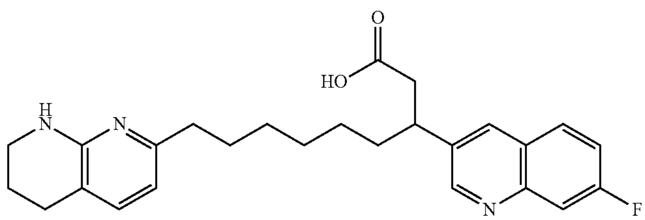 [SMILES: O=C(O)CC(CCCCCCc1ccc2c(n1)NCCC2)c1cnc2cc(F)ccc2c1] |
| A6 | 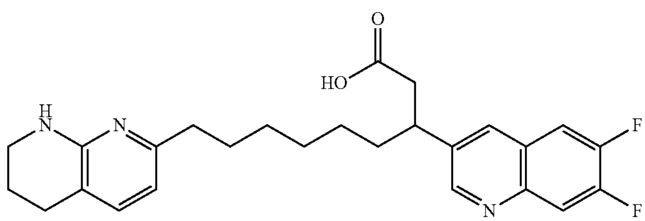 [SMILES: O=C(O)CC(CCCCCCc1ccc2c(n1)NCCC2)c1cnc2cc(F)c(F)cc2c1] |
| A7 | 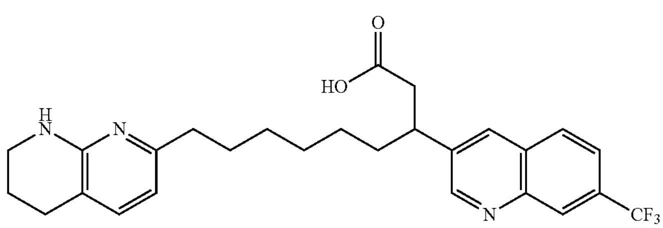 [SMILES: O=C(O)CC(CCCCCCc1ccc2c(n1)NCCC2)c1cnc2cc(C(F)(F)F)ccc2c1] |
| A8 | 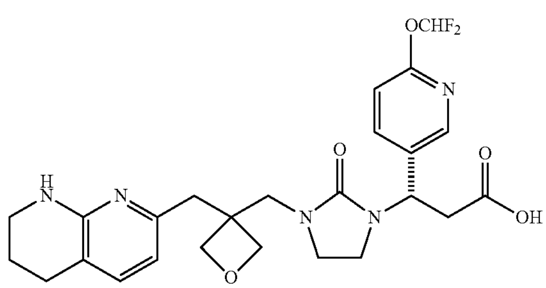 [SMILES: O=C(O)C[C@@H](c1ccc(OC(F)F)nc1)N1CCN(CC2(Cc3ccc4c(n3)NCCC4)COC2)C1=O] |
| A9 | 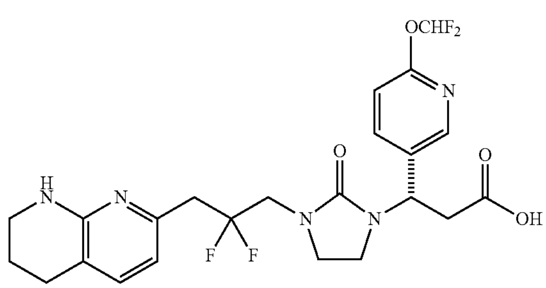 |

TABLE 1-continued
| Cmpd # | Chemical Structure |
|---|---|
| A10 | 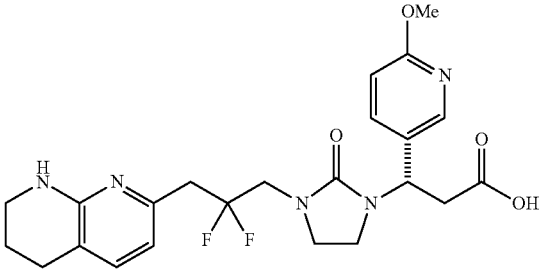 [SMILES: COc1ccc([C@H](CC(=O)O)N2CCN(CC(F)(F)Cc3ccc4c(n3)NCCC4)C2=O)cn1] |
| A11 | 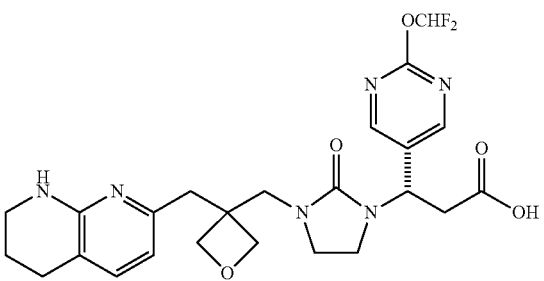 [SMILES: O=C(O)C[C@@H](c1cnc(OC(F)F)nc1)N1CCN(CC2(Cc3ccc4c(n3)NCCC4)COC2)C1=O] |
| A12 | 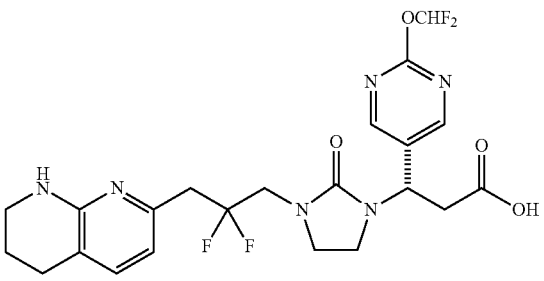 |
| A13 | 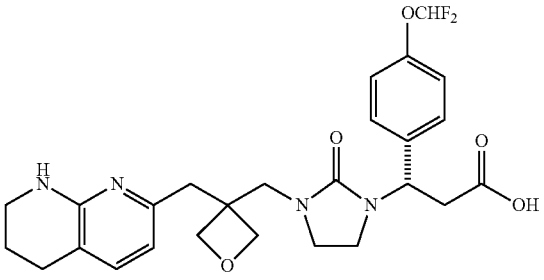 |
| A14 | 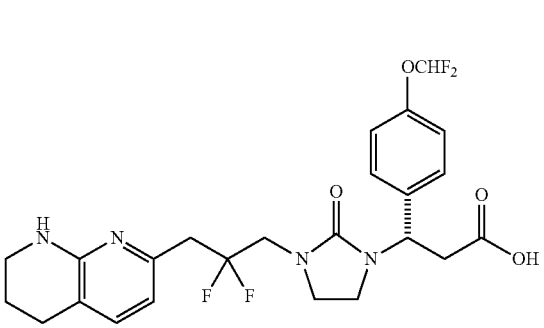 [SMILES: O=C(O)C[C@@H](c1ccc(OC(F)F)cc1)N1CCN(CC(F)(F)Cc2ccc3c(n2)NCCC3)C1=O] |

In one aspect, a compound of the present invention is selected from compounds A1, A2, and A3, or a pharmaceutically acceptable salt or solvate thereof. In a further aspect, a compound of the present invention is selected from compounds A1 and A2, or a pharmaceutically acceptable salt or solvate thereof. In a further aspect, a compound of the present invention is compound A1, or a pharmaceutically acceptable salt or solvate thereof.

In one aspect, a compound of the present invention is a pharmaceutically acceptable salt. In one aspect, a compound of the present invention is a solvate. In a further aspect, a compound of the present invention is a hydrate.

In one aspect, a compound of the present invention inhibits the activity of αv integrins (e.g., αvβ3 and αvβ5) at a submicromolar concentration, e.g., below 1 μM, 0.8 μM, 0.6 μM, 0.5 μM, 0.2 μM, or 0.1 μM.

In one aspect, a compound of the present invention inhibits cellular adhesion to vitronectin through the αv integrin (e.g., αvβ3 and αvβ5) at or below an $IC_{50}$ of 2.0E-07 M using a human dermal microvascular endothelial cell (HMVEC) assay. In a further aspect, a compound of the present invention inhibits cellular adhesion to vitronectin through the αv integrin (e.g., αvβ3 and αvβ5) at or below an $IC_{50}$ of 2.5E-08 M using an HMVEC assay. In a further aspect, a compound of the present invention inhibits cellular adhesion to vitronectin through the αv integrin (e.g., αvβ3 and αvβ5) at or below an $IC_{50}$ of 1.0E-08 M using an HMVEC assay. In one aspect, a compound of the present invention inhibits cellular adhesion to vitronectin through the αv integrin (e.g., αvβ3 and αvβ5) at or below an $IC_{50}$ of 2.5E-07 M using a rat lung microvascular endothelial cell (RLMVEC) assay. In a further aspect, a compound of the present invention inhibits cellular adhesion to vitronectin through the αv integrin (e.g., αvβ3 and αvβ5) at or below an $IC_{50}$ of 3.5E-08 M using an RLMVEC assay. In one aspect, a compound of the present invention inhibits cellular adhesion to vitronectin through the αv integrin (e.g., αvβ3 and αvβ5) at or below an $IC_{50}$ of 2.0E-08 M using a rabbit aortic endothelial cell (RAEC) assay. In a further aspect, a compound of the present invention inhibits cellular adhesion to vitronectin through the αv integrin (e.g., αvβ3 and αvβ5) at or below an $IC_{50}$ of 1.0E-08 M using an RAEC assay.

In one aspect, a compound of the present invention inhibits or decreases formation of blood vessels in a tissue or organ, in vivo or in vitro. In one aspect, a compound of the present invention decreases the formation of blood vessels below 90%, 80%, 70%, 60%, 50%, 40%, 30%, 20%, 10%, or 5%, as compared to that in an untreated control. In a further aspect, a compound of the present invention decreases the formation of blood vessels below 60%, 50%, 40%, 30%, 20%, 10%, or 5%, as compared to that in an untreated control. In a further aspect, a compound of the present invention decreases the formation of blood vessels below 40%, 30%, 20%, 10%, or 5%, as compared to that in an untreated control. In one aspect, the tissue is a tissue from the eye, such as a retinal tissue. In one aspect, the organ is the eye.

In one aspect, a compound of the present invention is efficiently distributed to the back of the eye, e.g., retina, after topical administration. In one aspect, a compound of the present invention is efficiently distributed to the retina within 12 hours, 10 hours, 8 hours, 6 hours, 4 hours, 2 hours, or 1 hour, after topical administration to the eye. In a further aspect, a compound of the present invention is efficiently distributed to the retina within 8 hours, 6 hours, 4 hours, 2 hours, or 1 hour, after topical administration to the eye.

Compounds of the present invention can be conveniently prepared by a variety of methods familiar to those skilled in the art. The compounds of each of the formulae described herein may be prepared according to the following procedures from commercially available starting materials or starting materials which can be prepared using literature procedures. These procedures show the preparation of representative compounds of this invention. It is understood that compounds of the present invention other than those illustrated in the following schemes can be made using these schemes with modifications commonly known in the art (e.g., using different starting material, changing reaction solvents, or adjusting reaction duration or temperature).

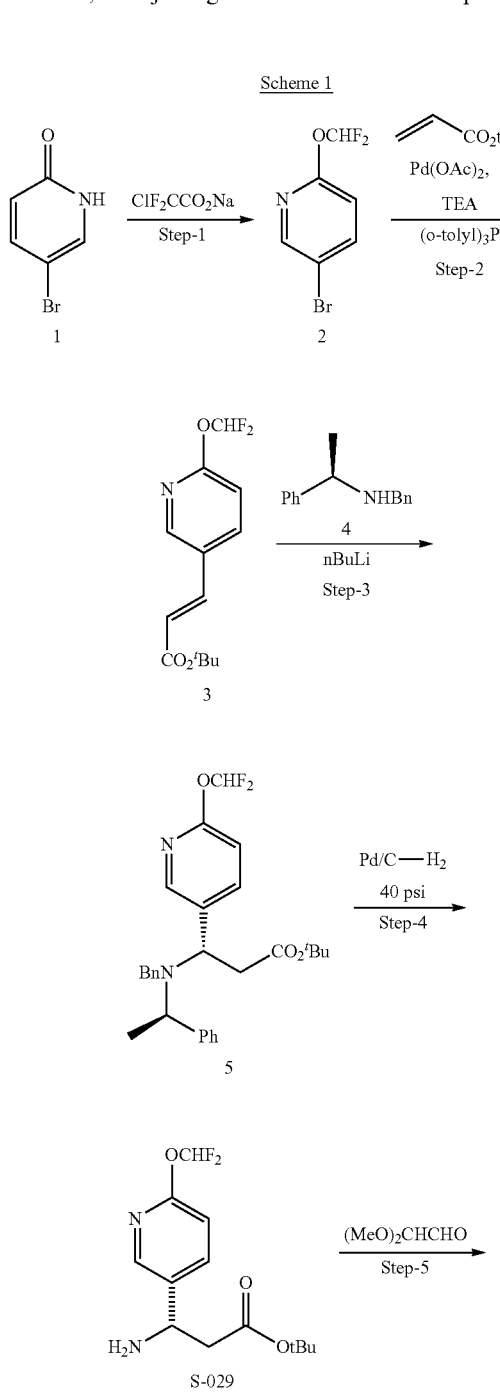

Scheme 1

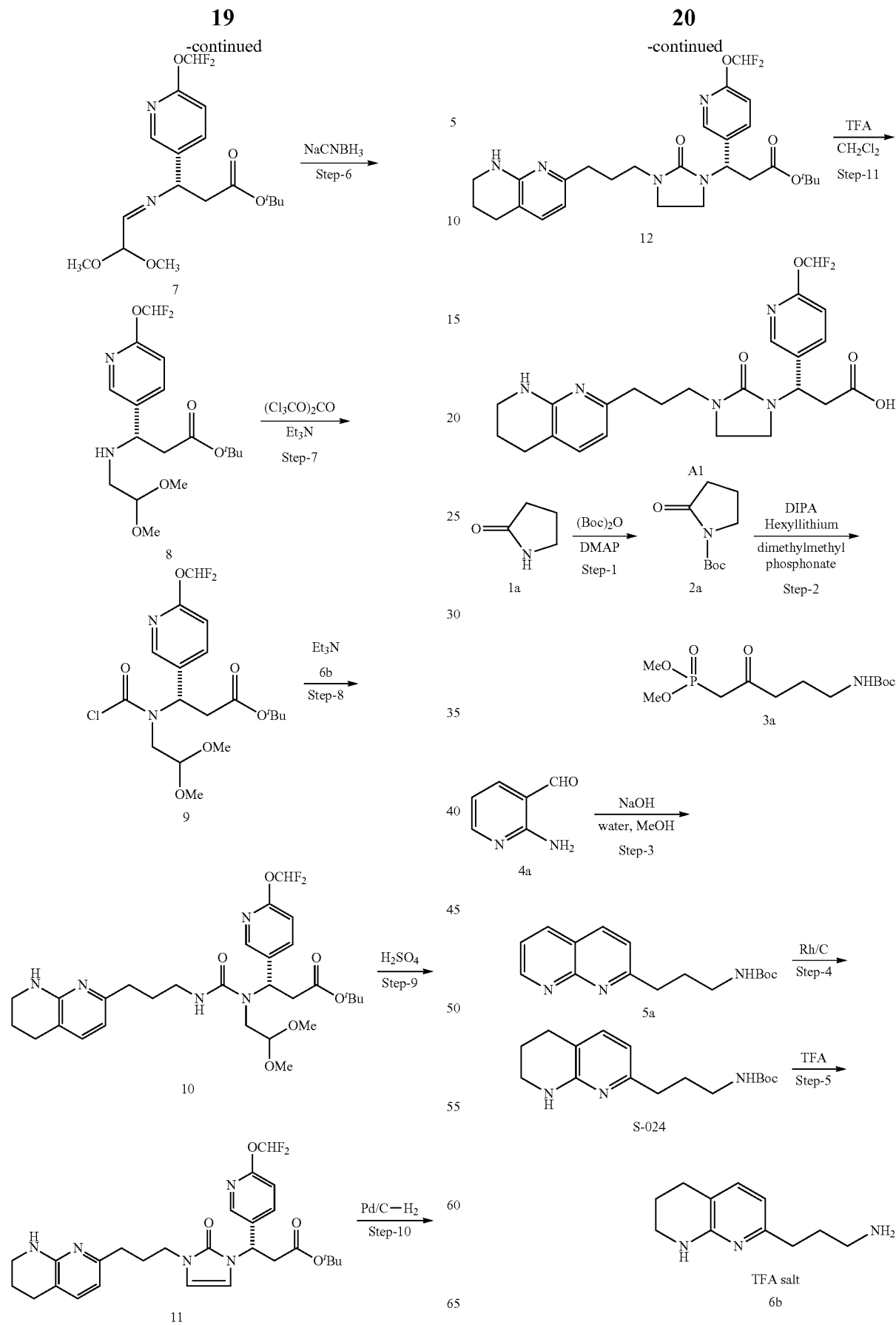

Scheme 2
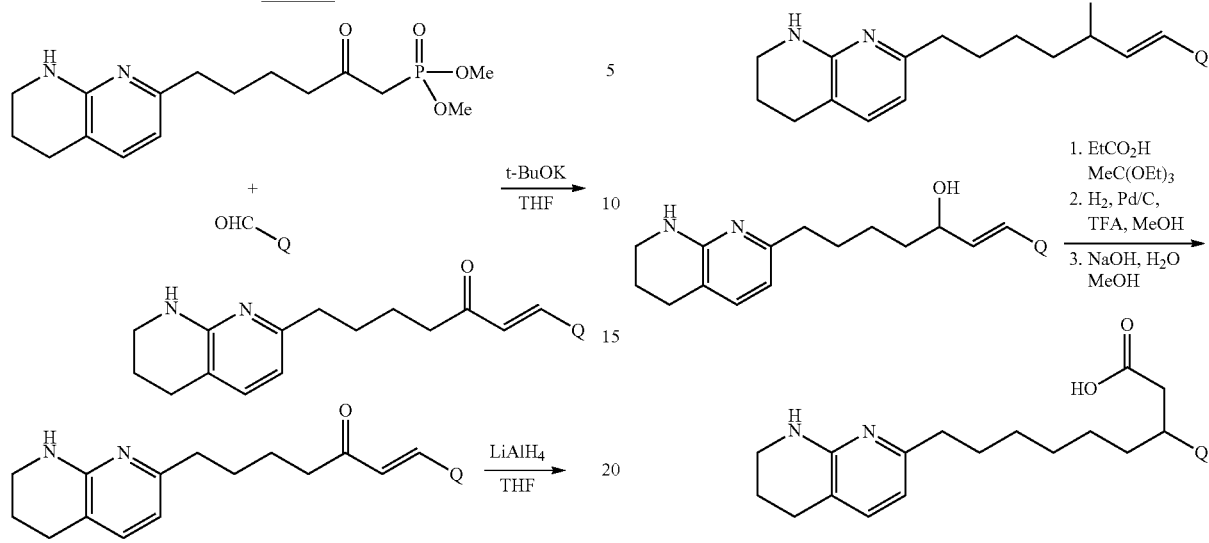
Scheme 3
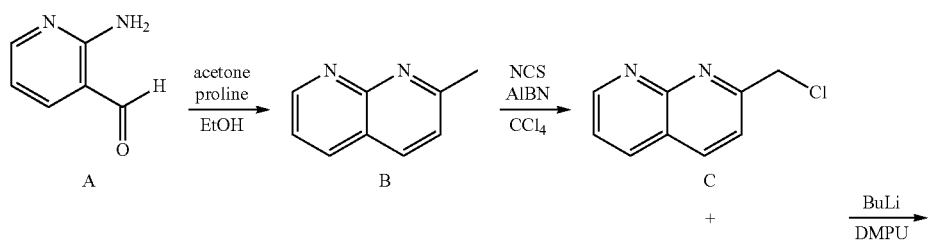
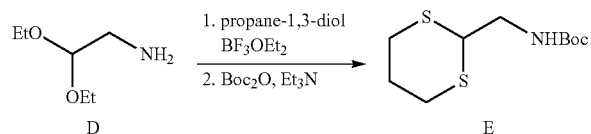
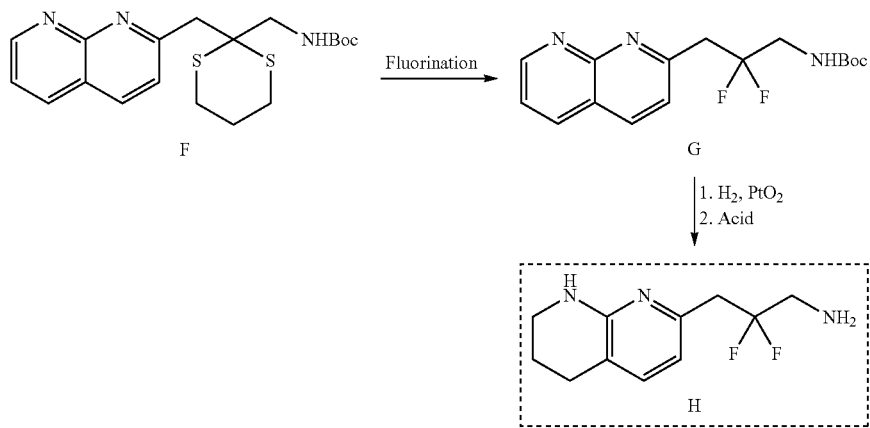

Scheme 4
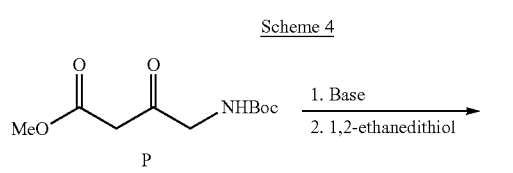
P
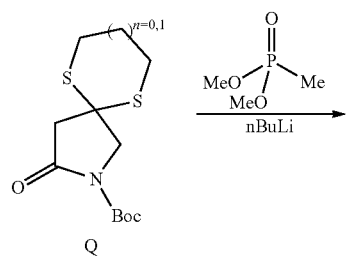
Q
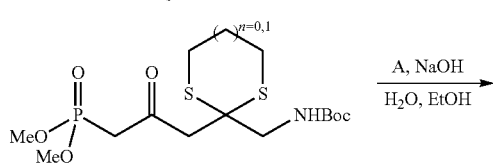
R
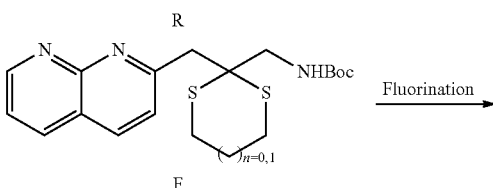
F
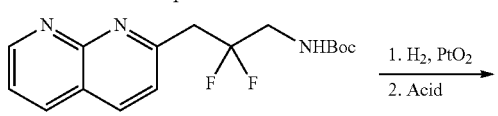
G
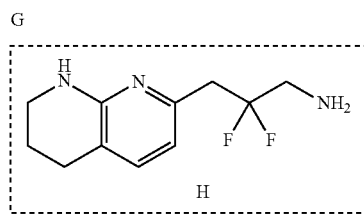
H
Scheme 5
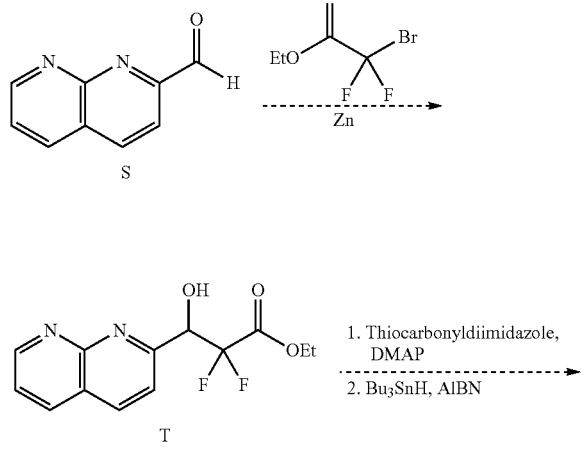
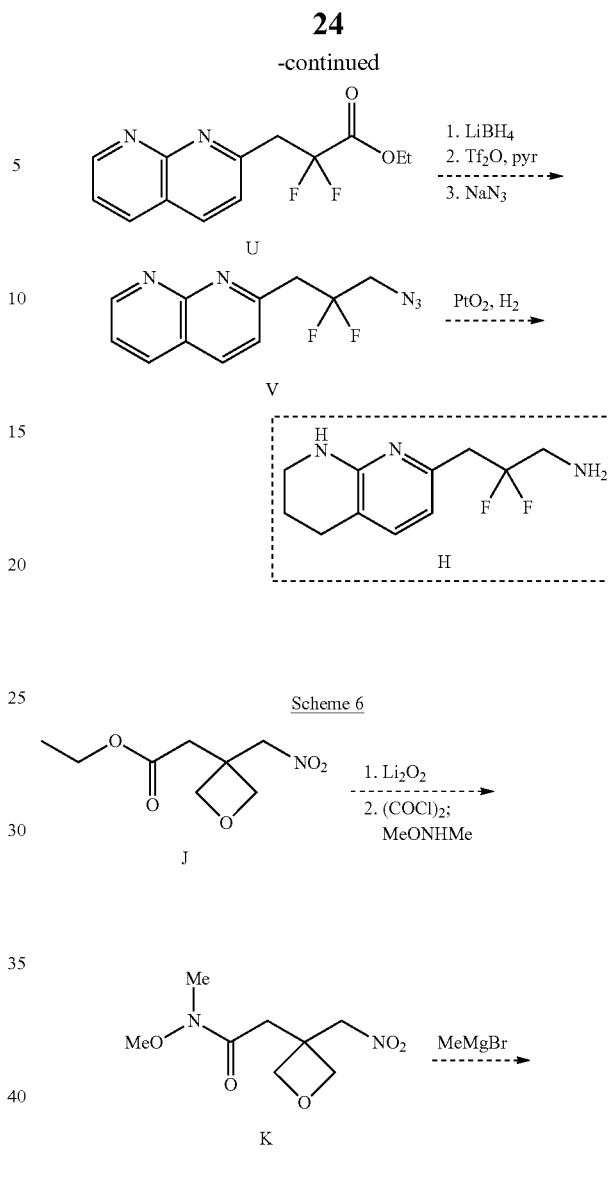
Scheme 6
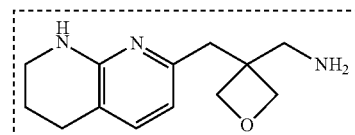

25

Scheme 7

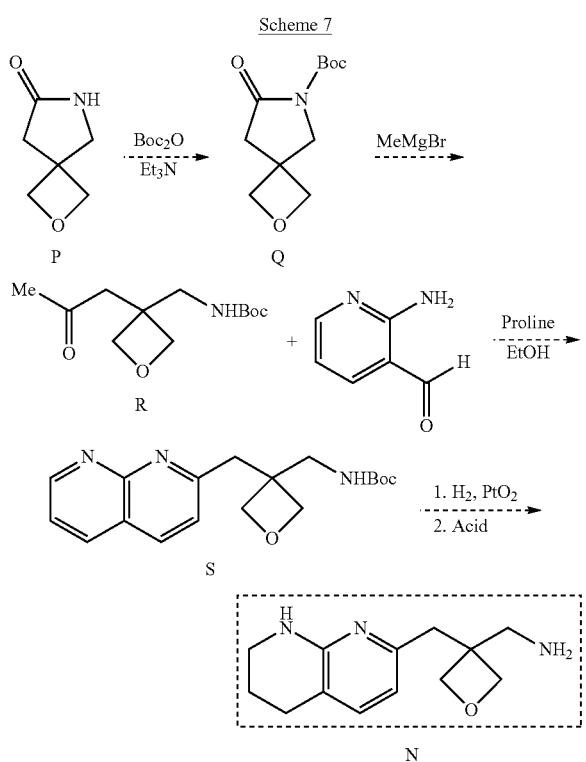

Scheme 8

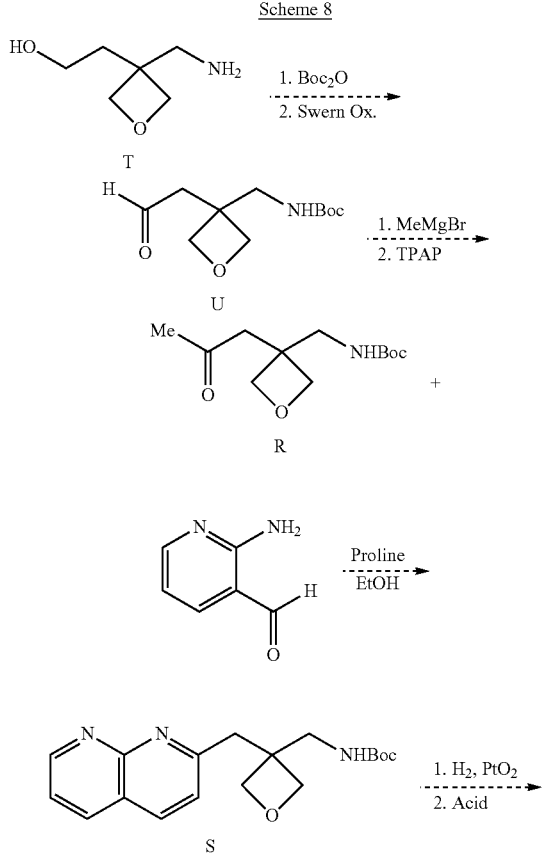

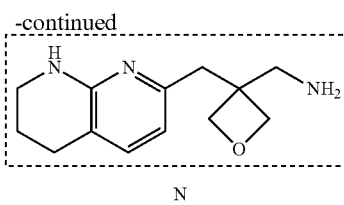

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers. It is intended that all of the possible optical isomers and diastereomers in mixtures and as pure or partially purified compounds are included within the ambit of the invention. The invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diasteriomeric mixture is often a mixture of diasteriomeric salts formed by contacting a racemic mixture of compounds with an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which are well known in the art.

Alternatively, any enantiomer of a compound may be obtained by stereoselective synthesis using optically pure starting materials or reagents of known configuration by methods well known in the art.

Some of the compounds of the invention may exist in unsolvated as well as solvated forms such as, for example, hydrates.

"Solvate" means a solvent addition form that contains either a stoichiometric or non-stoichiometric amounts of the solvent molecules. Some compounds have a tendency to trap a fixed molar ratio of the solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances (e.g., a compound of the invention) in which the water retains its molecular state as $H_2O$, such combination being able to form one or more hydrate. In hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates include sesquihydrates, monohydrates, dehydrates, and trihydrates. Equally suitable are the hydrates of salts of the compounds of the invention.

For use in medicine, the salts of the compounds of the invention refer to non-toxic "pharmaceutically acceptable salts". Other salts may, however, be useful in the preparation of the compounds of the invention or pharmaceutically acceptable salts thereof. Salts encompassed within the term "pharmaceutically acceptable salts" refer to non-toxic salts of the compounds of the invention which can be prepared by reacting the free base with a suitable organic or inorganic acid. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts which may be derived from ammonia or organic amines, such as, for example, diethylamine, triethylamine, ethyldiisopropylamine, procaine, dibenzylamine, N-methylmorpholine, dihydroabietylamine, or methylpiperidine.

The invention includes within its scope prodrugs of the compounds of the invention. In general, such prodrugs will be functional derivatives of the compounds of the invention which are readily convertible in vivo into the required compound. Thus, in the methods of treatment of the invention, the term "administering" shall encompass the treatment of the various disease and conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of the invention into the biological milieu.

The invention also includes one or more metabolites of a compound of the invention.

The present invention also comprehends deuterium labeled compounds of formula I or II or the compounds listed in Table 1, wherein a hydrogen atom is replaced by a deuterium atom. The deuterium labeled compounds comprise a deuterium atom having an abundance of deuterium that is substantially greater than the natural abundance of deuterium, e.g., 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of formula I or II or the compounds listed in Table 1 can generally be prepared by carrying out the procedures disclosed in the Schemes and/or Examples described herein, by substituting a readily available deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium, i.e., $^2$H, can afford certain therapeutic advantages resulting from greater metabolic stability, for example, increased in vivo half-life and/or reduced dosage requirements.

In one aspect, the present invention relates to a method of synthesizing a compound of the invention or a pharmaceutically acceptable salt or solvate thereof.

Pharmaceutical Compositions of the Invention

The present invention relates to pharmaceutical compositions comprising a compound of the invention as an active ingredient. In one aspect, the invention provides a pharmaceutical composition comprising at least one compound of formula I or II, or a pharmaceutically acceptable salt or solvate thereof and one or more pharmaceutically acceptable carriers or excipients. In one aspect, the invention provides a pharmaceutical composition comprising at least one compound selected from Table 1. In a further aspect, the invention provides a pharmaceutical composition comprising at least one compound selected from compounds A1, A2, and A3. In a further aspect, the invention provides a pharmaceutical composition comprising at least one compound selected from compounds A1 and A2. In a further aspect, the invention provides a pharmaceutical composition comprising compound A1.

As used herein, the term "composition" is intended to encompass a product comprising the specified ingredients in the specified amounts, as well as any product which results, directly or indirectly, from combination of the specified ingredients in the specified amounts.

The compounds of the invention can be formulated for oral administration in forms such as tablets, capsules (each of which includes sustained release or timed release formulations), pills, powders, granules, elixirs, tinctures, suspensions, syrups and emulsions. The compounds of the invention can also be formulated for intravenous (bolus or in-fusion), intraperitoneal, topical (e.g., ocular eye-drop), subcutaneous, intramuscular or transdermal (e.g., patch) administration, all using forms well known to those of ordinary skill in the pharmaceutical arts. Preferably, compounds of the invention for the treatment of macular degeneration, DR, DME, or macular edema following RVO, are formulated for topical administration, for example, in the form of eye-drops.

For topical ocular administration, the compositions are provided as ophthalmic formulation comprising a compound of the present invention in concentration between about 0.01 and about 5 weight percent, preferably between about 0.1 and about 5.0 weight percent, more preferably between about 0.5 and about 5.0 weight percent, and most preferably between about 0.8 and about 3.0 weight percent.

The ophthalmic formulation of the present invention may be in the form of an aqueous solution comprising an aqueous vehicle.

The aqueous vehicle component of the ophthalmic formulation may comprise water and at least one ophthalmically acceptable excipient. Preferably, the aqueous vehicle comprises a solution of the one or more ophthalmically acceptable excipients in water.

Suitable ophthalmically acceptable excipients include those selected from the group consisting of a solubility enhancing agent, chelating agent, preservative, tonicity agent, viscosity/suspending agent, buffer, and pH modifying agent, and a mixture thereof. Preferably, the ophthalmically acceptable excipient is selected from the group consisting of a solubility enhancing agent, chelating agent, preservative, tonicity agent, viscosity/suspending agent, and pH modifying agent, and a mixture thereof.

Any suitable ophthalmically acceptable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof. Preferably, solubility enhancing agent includes β-cyclodextrin sulfobutyl ether, hyrdoxypropyl-β-cyclodextrin, sulphated β-cyclodextrin (S-β-CD), and maltosyl-β-cyclodextrin, and mixtures thereof. β-cyclodextrin sulfobutyl ether is a particularly preferred solubility enhancing agent. The solubility enhancing agent(s) may be added in an amount of about 1 to about 20 wt %, preferably about 1 to about 10 wt %, and more preferably about 5 to about 10 wt %.

Any suitable ophthalmically acceptable chelating agent can be used. Examples of a suitable ophthalmically acceptable chelating agent include those selected from the group consisting of ethylenediaminetetraacetic acid and metal salts thereof, disodium edetate, trisodium edetate, and tetrasodium edetate, and mixtures thereof. Disodium edetate is a particularly preferred chelating agent. The chelating agent(s) may be added in an amount of about 0.001 to about 0.05 wt %, preferably about 0.001 to about 0.02 wt %, more preferably about 0.002 to about 0.01 wt %, and most preferably about 0.002 to about 0.005 wt %.

Preferably, the aqueous vehicle includes a preservative. Preferred preservatives include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, sorbic acid, and mixtures thereof. More preferably, the preservative is a quaternary ammonium salt such as benzalkonium halides (preferably benzalkonium chloride), chlorhexidine gluconate, benzethonium chloride, cetyl pyridinium chloride, potassium sorbate, sodium benzoate, ethyl p-hydroxybenzoate, butyl p-hydroxybenzoate, or propylaminopropyl biguanide, or mixtures thereof. Propylaminopropyl biguanide is an especially preferred preservative. The preservative(s) may be used in an amount of about 0.00001 to about 0.0001 wt %, preferably about 0.00001 to about 0.00008 wt %, and more preferably about 0.00002 to about 0.00005 wt %.

The aqueous vehicle may also include a tonicity agent to adjust the tonicity (osmotic pressure) in order to achieve an ophthalmically compatible formulation. The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof. Preferably, the tonicity agent is selected from the group consisting of glycerin, mannitol, potassium chloride, and sodium chloride. More preferably mannitol and/or sodium chloride (and most preferably a mixture thereof) are employed. The tonicity agent(s) may be used in an amount of about 0.05 to about 8 wt %, preferably about 0.1 to about 6 wt %, more preferably about 0.1 to about 4 wt %, and most preferably about 0.2 to about 4 wt %.

When a mixture of mannitol and sodium chloride is used as tonicity agents, preferably the weight ratio of mannitol: sodium chloride is about 4:1 to about 15:1, more preferably about 6:1 to about 14:1, or 8:1 to about 14:1 and particularly about 10:1 to about 12:1. If mannitol alone is used as the tonicity agent, it is preferably used in an concentration of about 4.5 to about 6.5 wt %, and more preferably in a concentration of about 5.0 to about 5.5 wt %. If sodium chloride alone is used as the tonicity agent, it is used in a concentration of about 0.05 to about 8 wt %, preferably about 0.1 to about 6 wt %, more preferably about 0.1 to about 4 wt %, and most preferably about 0.2 to about 4 wt %.

The aqueous vehicle preferably also contains a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof. In preferred embodiments of the present invention, the viscosity/suspending agent is a carbomer, more preferably Carbopol 974P. The viscosity/suspending agent(s) may be present in an amount of about 0.05 to about 2 wt %, preferably 0.1 to about 1 wt %, more preferably about 0.2 to about 0.8 wt %, and most preferably about 0.3 to about 0.5 wt %.

In order to adjust the formulation to an ophthalmically acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target ophthalmically acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ϵ-aminocaproic acid, and mixtures thereof. The buffer agent(s) may be present in an amount of about 0.05 to about 5 wt %, preferably 0.1 to about 5 wt %, more preferably about 0.2 to about 5 wt %, and most preferably about 0.5 to about 5 wt %.

The ophthalmic formulation for topical administration to the eye may further comprise a wetting agent. In any embodiment of the present invention the wetting agent is preferably a non-ionic wetting agent. More preferably, the wetting agent is water soluble or swellable. Most preferably the wetting agent is water soluble. "Water soluble" is to be understood in the manner used in standard texts such as the "Handbook of Pharmaceutical Excipients" (Raymond C Rowe, Paul J Sheskey and Sian C Owen, Fifth Edition, Pharmaceutical Press and American Pharmacists Association 2006). Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Specific examples of suitable wetting agents include those selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monostearate (polysorbate 60), poly(oxyethylene)sorbitan tristearate (polysorbate 65), poly(oxyethylene) sorbitan monooleate (polysorbate 80), poly(oxyethylene) sorbitan monolaurate, poly(oxyethylene) sorbitan trioleate, polyethoxylated ethers of castor oils such as polyoxyethylene hydrogenated castor oil 10, polyoxyethylene hydrogenated castor oil 40, polyoxyethylene hydrogenated castor oil 50 and polyoxyethylene hydrogenated castor oil 60, polyoxyl 40 stearate, sucrose fatty esters, and polyoxyethylene fatty esters, and mixtures thereof.

Preferably, the wetting agent is selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], and polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monosteaxate (polysorbate 60), poly(oxyethylene)sorbitan tristearate (polysorbate 65), poly(oxyethylene) sorbitan monooleate (polysorbate 80), poly(oxyethylene) sorbitan monolaurate, and poly(oxyethylene) sorbitan trioleate and mixtures thereof.

More preferably, the wetting agent is a polyoxyethylene-polyoxypropylene block copolymer (poloxamer). Examples of suitable poloxamers include: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127] and polyoxyethylene (20) polyoxypropylene (20) glycol [Pluronic L44] or a mixture thereof.

Further preferred are wetting agents selected from the group consisting of polyoxyethylene (42) polyoxypropylene (67) glycol [Pluronic PI 23], polyoxyethylene (54) polyoxypropylene (39) glycol [Pluronic P85], polyoxyethylene (196) polyoxypropylene (67) glycol [Poloxamer 407, Pluronic F127] and mixtures thereof.

An especially preferred wetting agent is polyoxyethylene (196) polyoxypropylene (67) glycol [Poloxamer 407, Pluronic F127].

Particularly preferred formulations for topical administration to the eye of the present invention comprise a compound of the present invention, a solubility enhancing agent, a cheating agent, a preservative, a tonicity agent, a viscosity/suspending agent, a buffer, and a pH modifying agent. More particularly preferred formulations are comprised of an aqueous solution of a β-cyclodextrin, a borate salt, boric acid, sodium chloride, disodium edetate, and propylaminopropyl biguanide.

In one aspect, the ophthalmic formulation of the present invention is in the form of a solution, such as one of the following:

| Solution Composition | |
|---|---|
| a compound of the invention | 0.1-5.0 g |
| a solubility enhancing agent | 1-20 g |
| a buffering agent | 0.05-5.0 g |
| an tonicity agent | 0.05-8 g |
| a chelating agent | 1-50 mg |
| a preservative | 0.01-0.1 mg |
| water | 100 ml |
| a compound of the invention | 0.8-3.0 g |
| a solubility enhancing agent | 5-10 g |
| a buffering agent | 0.5-5.0 g |
| an tonicity agent | 0.2-4 g |
| a chelating agent | 2-5 mg |
| a preservative | 0.02-0.05 mg |
| water | 100 ml |

| Solution Composition | I | II | III | IV |
|---|---|---|---|---|
| a compound of the invention | 2.5 g | 2.0 g | 1.5 g | 1.0 g |
| a solubility enhancing agent | 10 g | 10 g | 10 g | 5 g |
| buffering agent 1 | 1.05 g | 1.05 g | 1.05 g | 1.05 g |
| buffering agent 2 | 0.285 g | 0.285 g | 0.285 g | 0.285 g |
| an tonicity agent | 0.25 g | 0.25 g | 0.25 g | 0.25 g |
| a chelating agent | 2.5 mg | 2.5 mg | 2.5 mg | 2.5 mg |
| a preservative | 0.03 mg | 0.03 mg | 0.03 mg | 0.03 mg |
| water | 100 ml | 100 ml | 100 ml | 100 ml |

The ophthalmic formulation of the present invention may also be in the form of a gel or a semi-gel, or both; a jelly; a suspension; an emulsion; an oil; an ointment; a cream; or a spray.

The ophthalmic gel, semi-gel, jelly, suspension, emulsion, oil, ointment, cream, or spray may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzalkonium chloride, P-oxybenzoates such as methyl p-oxybenzoate or ethyl p-oxybenzoate, benzyl alcohol, phenethyl alcohol, sorbic acid or its salt, thimerosal, chlorobutanol and the like), solubilizing enhancing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, Ssdium citrate, condensed sodium phosphate) and the like. Each of these additives may be in the amount or concentration similar to those described for the ophthalmic formulation in the form of a solution above.

Furthermore the compounds of the invention may be formulated for topical administration by incorporation into novel ophthalmic formulations including but not limited to: microemulsions, liposomes, niosomes, gels, hydrogel, nanoparticles, and nanosuspension.

1. Microemulsions

Microemulsions are dispersion of water and oil facilitated by a combination of surfactant and cosurfactant in a manner to reduce interfacial tension. These systems are usually characterized by higher thermodynamic stability, small droplet size (approximately 100 nm) and clear appearance. Their transparent appearance is due to the high level of dispersion of the internal phase, and the size of it ranges from 100-1000 angstroms. Processes for forming microemulsions suitable for use in ophthalmic formulations are described in Vandamme T F. Prog Retinal Eye Res 2002; 21:15-34, which is incorporated by reference.

2. Liposomes

Liposomes are lipid vesicles containing aqueous core and have been widely exploited in ocular delivery for various drug substances. Depending on the nature of the lipid composition selected, liposomes can provide extended release of the drug.

3. Niosomes

Niosomes are bilayered structural vesicles made up of nonionic surfactant and are capable of encapsulating both lipophilic and hydrophilic compounds. They can release the drug independent of pH and enhance ocular bioavailability. Niosomes are microscopic lamellar structures that are formed on the admixture of nonionic surfactant of the alkyl or diakyl polyglycerol ether class and cholesterol with subsequent hydration in aqueous media. Structurally niosomes are similar to liposomes, in that they are also made up of a bilayer. However, the bilayer in the case of nisomes is made up of nonionic surface-active agents rather than phospholipids as in the case of liposomes. Niosomes may be unilamellar or multilamellar depending on the method used to prepare them. They are capable of entrapping hydrophilic and hydrophobic solutes. They possess great stability and lack many disadvantages associate with liposomes such as high cost and the variable purity of phospholipids. The properties of niosomes and process for preparing them are well known in the art, see e.g., Wagh V D et al., J Pharm Res 2010; 3(7):1558-1563; Kaur H et al., Int J Pharm Sci Rev Res 2012; 15(1):113-120, each of which is incorporated by reference.

4. Gels

Ophthalmic gels are composed of mucoadhesive polymers that provide localized delivery of an active ingredient to the eye. Such polymers have a property known as bioadhesion, meaning attachment of a drug carrier to a specific biological tissue. These polymers are able to extend the contact time of the drug with the biological tissues and thereby improve ocular bioavailability. The choice of the polymer plays a critical role in the release kinetics of the drug from the dosage form. Several bioadhesive polymers are available with varying degree of mucoadhesive performance. Some examples are carboxymethylcellulose, carbopol, polycarbophil, and sodium alginate. The use of gel formulations in ocular drug deliver has been reviewed in Ali Y et al., Adv Drug Deliv Rev 2006; 58: 1258-1268, which is incorporated by reference.

5. Hydrogels

Hydrogels are three-dimensional, hydrophilic, polymeric networks capable of taking in large amounts of water or biological fluids. Residence time can be significantly enhanced with a hydrogel formulation. The gelation can be obtained by changing temperature and pH. Poloxamers, the most widely used polymer, contains the hydrophobic part in the centre surrounded by a hydrophilic part. Though they are widely employed to enhance the residence time. Recent perspectives in the use of hydrogels in ocular drug deliver are described by Gaudana R, Jwala J, Boddu S H S, Mitra A K. Pharm Res. 2009; 26(5):1197-1216 which is incorporated by reference.

6. Nanoparticles

Nanoparticles are defined as particles with a diameter of less than 1 μm, comprising of various biodegradable or non biodegradable polymers, lipids, phospholipids or metals. They can be classified as nanospheres or nanocapsules depending upon whether the drug has been uniformly dispersed or coated within polymeric material. The uptake and distribution of nanoparticles is dependent on their size. The use of nanoparticles in ocular drug delivery has recently been reviewed by Hing et al., Int. J. Ophthalmol 2013; 6:390-396, which is incorporated by reference.

7. Nanosuspensions

Nanosuspensions are defined as sub-micron colloidal systems that consist of poorly water soluble drugs suspended in an appropriate dispersion medium stabilized by surfactants. Usually, nanosuspensions consist of colloidal carriers like polymeric resins which are inert in nature. Nanosuspensions enhance drug solubility and thus bioavailability. Unlike microemulsions, nanosuspensions are non-irritant. Charge on the surface of nanoparticles facilitates their adhesion to the cornea. The use of nanosuspensions in drug delivery is reviewed in Rabinow, Nature Rev Drug Disc 2004; 785-796, which is incorporated by reference.

The compounds of the present invention can also be administered in the form of a formulation suitable for ocular topical delivery. Detailed descriptions of formulation suitable for ocular topical delivery are described in J. D. Bartlett and S. D. Jaanus, "Clinical Ocular Pharmacology", 2008, Elsevier Health Sciences, which is incorporated by reference.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, and polyethyleneoxidepolylysine substituted with palmitoyl residues. Furthermore, the compounds of the invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and crosslinked or amphipathic block copolymers of hydrogels.

The present invention also provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin $\alpha 5\beta 1$, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof.

The present invention further provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin $\alpha 5\beta 1$, b) a cytotoxic/antiproliferative agent, c) an inhibitor of epidermal-derived, fibroblast-derived, or platelet-derived growth factors, d) an inhibitor of VEGF, and e) an inhibitor of phosphoinositide 3-kinase, and a mixture thereof.

Nonlimiting examples of antagonists of integrin $\alpha 5\beta 1$ are (S)-2-((R)-2-((S)-2-((S)-2-((S)-1-acetylpyrrolidine-2-carboxamido)-3-(1H-imidazol-5-yl)propanamido)-3-hydroxy-propanamido)-3-mercaptopropanamido)succinamide, and JSM6427, described in Stragies, R. et al., J. Med. Chem. 2007, 50:3786-3794, herein incorporated by reference.

Nonlimiting examples of cytotoxic/antiproliferative agents are taxol, vincristine, vinblastine, and doxorubicin.

Nonlimiting examples of inhibitors of epidermal-derived, fibroblast-derived, or platelet-derived growth factors are pazopanib, and sunitinib, Nonlimiting examples of inhibitors of vascular endothelial derived growth factor (VEGF) are bevacizumab and ranibizumab, Nonlimiting examples of inhibitors of phosphoinositide 3-kinase are indelalisib and 2-morpholin-4-yl-8-phenylchroman-4-one.

Methods of Use

Compounds of the invention typically display submicromolar inhibitory activity for the integrins $\alpha v$, such as $\alpha v\beta 3$ and $\alpha v\beta 5$. Inhibiting the function of $\alpha v\beta 3$ and $\alpha v\beta 5$ integrins prevents endothelial cell proliferation. Endothelial cell proliferation can result in deleterious neovascularization or angiogenesis, particularly choroidal neovascularization in the choriocapillaris, through Bruch's membrane, ultimately leading to blood and protein leakage below the macula. Bleeding, leaking, and scarring from these blood vessels eventually cause irreversible damage to the photoreceptors and rapid vision loss if left untreated.

Diabetic retinopathy, a closely related condition, is the result of microvascular retinal changes. Hyperglycemia-induced intramural pericyte death and thickening of the basement membrane lead to incompetence of the vascular walls in the retina, which affects the blood-retinal barrier and makes the retinal blood vessels more permeable. Damaged blood vessels leak fluid and lipids onto the macula, the part of the retina that provides us with detailed vision, causing the macula to swell. Eventually this can progress to develop a condition called macular edema.

Accordingly, AMD, DR, DME, and macular edema following central retinal vein occlusion (thrombosis) can be treated or prevented through administration (e.g., topical administration) of the compounds or pharmaceutical compositions of the present invention.

The present invention provides a method of treating or preventing a disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the invention provides treating a disease or condition. In one aspect, the invention provides preventing a disease or condition.

In one aspect, the compound or pharmaceutical composition of the invention is administered topically. In a further aspect, the compound or pharmaceutical composition of the invention is administered as an ophthalmic solution. In another aspect, the compound or pharmaceutical composition of the invention is administered as an ophthalmic emulsion, suspension, gel, or semi-gel. In another aspect, the compound or pharmaceutical composition of the invention is administered as an ophthalmic jelly, oil, ointment, cream, or spray.

The compounds or pharmaceutical compositions of the invention are administered in dosages effective to inhibit the function of $\alpha v\beta 3$ and/or $\alpha v\beta 5$ integrins and thus treat or prevent a disease condition mediated by the $\alpha v\beta 3$ and/or $\alpha v\beta 5$ integrin.

The present invention provides a method of treating or preventing a disease or condition mediated by an $\alpha v$ integrin in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the disease or condition is a disease or condition in which angiogenesis is involved. In a further aspect, the disease or condition is a disease or condition in which ocular angiogenesis is involved.

The present invention also provides a method of treating or preventing an $\alpha v\beta 3$ and/or $\alpha v\beta 5$ integrin-mediated disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO).

The present invention further provides a method of treating or preventing AMD, DR, DME, or macular edema following RVO, comprising administering to a subject in need thereof, a therapeutically effective amount of a compound of the invention or a pharmaceutically acceptable salt or solvate thereof or a therapeutically effective amount of a pharmaceutical composition of the invention. In one aspect, the invention provides treating AMD, DR, DME, or macular edema following RVO. In one aspect, the invention provides preventing AMD, DR, DME, or macular edema following RVO.

The present invention further provides a method of treating or preventing a disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention, in combination with a second therapy for treating or preventing the disease or condition. In one aspect, the disease or condition is mediated by an αv integrin. In a further aspect, the disease or condition is mediated by an αvβ3 and/or αvβ5 integrin. In one aspect, the disease or condition is a disease or condition in which angiogenesis is involved. In a further aspect, the disease or condition is a disease or condition in which ocular angiogenesis is involved. In one aspect, the second therapy comprises administration of one or more of the following: a) an antagonist of integrin α5β1, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof. In a further aspect, the second therapy comprises administration of one or more of the following: a) an antagonist of integrin α5β1, b) a cytotoxic/antiproliferative agent, c) an inhibitor of epidermal-derived, fibroblast-derived, or platelet-derived growth factor, d) an inhibitor of VEGF, and e) an inhibitor of phosphoinositide 3-kinase, and a mixture thereof. In a further aspect, the second therapy comprises administration of an inhibitor of VEGF. In a further aspect, the VEGF inhibitor is bevacizumab or ranibizumab.

The second therapy can be administered via any administration routes, including oral administration in forms such as tablets, capsules (each of which includes sustained release or timed release formulations), pills, powders, granules, elixirs, tinctures, suspensions, syrups emulsions, intravenous administration (bolus or in-fusion), intraperitoneal administration, topical administration (e.g., ocular eyedrop), subcutaneous administration, intramuscular administration, transdermal (e.g., patch) administration, and intravitreal administration. In one aspect, the second therapy is administered through intravitreal injection.

Administration of the second therapy in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner.

In accordance with the method of the invention, the individual components of the combination can be administered separately at different times during the course of therapy or concurrently in divided or single combination forms. The instant invention is therefore to be understood as embracing all such regimens of simultaneous or alternating treatment, and the term "administering" is to be interpreted accordingly. It will be understood that the scope of combinations of the compounds of the invention with other agents useful for treating αv integrin-mediated conditions includes in principle any combination with any pharmaceutical composition useful for treating macular degeneration, DR, DME, or macular edema following RVO. When the method of the invention is a combination treatment of a formulation of the present invention topically administered to the eyes and an anti-VEGF protein or aptamer, the procedures, dosages and frequencies of the anti-VEGF protein or aptamer are as described in the package inserts for those agents.

The dosage regimen utilizing the compounds of the invention is selected in accordance with a variety of factors including type, species, age, weight, sex and medical condition of the patient; the severity of the condition to be treated; and the particular compound or salt thereof employed. An ordinary skilled physician, veterinarian or clinician can readily determine and prescribe the effective amount of the drug required to prevent, counter or arrest the progress of the condition.

In the methods of the invention, the compounds herein described in detail can form the active ingredient, and are typically administered in admixture with suitable pharmaceutical diluents, excipients or carriers (collectively referred to herein as "carrier") suitably selected with respect to the intended topical administration to the eye and consistent with conventional pharmaceutical practices.

For purposes of the invention, the following definitions will be used (unless expressly stated otherwise):

"A compound of the invention", "compounds of the invention", "a compound of the present invention", or "compounds of the present invention" refers to a compound (s) disclosed herein, e.g., a compound(s) of the invention includes a compound(s) of any of the formulae described herein including formula I and II and/or a compound(s) explicitly disclosed herein. Whenever the term is used in the context of the invention it is to be understood that the reference is being made to the free base and the corresponding pharmaceutically acceptable salts or solvates thereof, provided that such is possible and/or appropriate under the circumstances.

"Pharmaceutical" or "pharmaceutically acceptable" when used herein as an adjective, means substantially non-toxic and substantially non-deleterious to the recipient.

By "pharmaceutical composition" it is further meant that the carrier, diluent, solvent, excipient, and salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

"Solution" refers to a clear, homogeneous liquid dosage form that contains one or more chemical substances dissolved in a solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" refers to a liquid dosage form that contains solid particles dispersed in a liquid vehicle. "Suspension" as disclosed herein contemplates any variations based on the current state of the art or variations achieved by one skilled in the art.

"Excipient" is used herein to include any other compound that is not a therapeutically or biologically active compound and may be contained in or combined with one or more of the compounds of the present invention. As such, an excipient should be pharmaceutically or biologically acceptable or relevant (for example, an excipient should generally be non-toxic to the subject). "Excipient" includes a single such compound and is also intended to include a plurality of excipients. For the purposes of the present disclosure the term "excipient" and "carrier" are used interchangeably throughout the description of the present application.

"Therapeutically effective amount" refers to that amount of a drug or pharmaceutical agent that will elicit the biological or medical response of a tissue, system, animal, or human that is being sought by a researcher or clinician.

"Treat," "treating," or "treatment" refers to decreasing the symptoms, markers, and/or any negative effects of a disease or condition in any appreciable degree in a subject who currently has the disease or condition. In some embodiments, treatment may be administered to a subject who exhibits only early signs of a disease or condition for the purpose of decreasing the risk of developing the disease or condition. In some embodiments, "Treat," "treating," or "treatment" refers to amelioration of one or more symptoms of a disease or condition. For example, amelioration of one or more symptoms of a disease or condition includes a decrease in the severity, frequency, and/or length of one or more symptoms of a disease or condition.

"Prevent," "prevention," or "preventing" refers to any method to partially or completely prevent or delay the onset of one or more symptoms or features of a disease or condition. Prevention may be administered to a subject who does not exhibit any sign of a disease or condition.

"Subject" means a human or animal (in the case of an animal, more typically a mammal). In one aspect, the subject is a human.

The term "symptom" is defined as an indication of disease, illness, injury, or that something is not right in the body. Symptoms are felt or noticed by the individual experiencing the symptom, but may not easily be noticed by others. Others are defined as non-health-care professionals.

"αv integrin antagonist" refers to a compound which binds to and inhibits or interferes with the function of either αvβ3 or αvβ5, or a compound which binds to and inhibits or interferes with the function of both αvβ3 and αvβ5 (i.e., a dual αvβ3/αvβ5 antagonist). The compounds bind to the receptors as antagonists, blocking or interfering with the binding of the native agonist, such as vitronectin, while not provoking a biological response themselves.

"Bone resorption" refers to the process by which osteoclasts degrade bone.

"Alkyl" refers to straight chain or branched alkyl of the number of carbon atoms specified (e.g., $C_1$-$C_4$ alkyl), or any number within this range (methyl, ethyl, propyl, i-propyl, butyl, i-butyl, t-butyl, etc.).

"Alkoxy" refers to straight chain or branched alkoxides of the number of carbon atoms specified (e.g., $C_1$-$C_6$ alkoxy), or any number within this range (methoxy, ethoxy, propoxy, i-propoxy, butoxy, i-butoxy, t-butoxy, etc.).

"Carbocyclic ring" refers to saturated cycloalkyl of the number of carbon atoms specified (i.e., $C_3$ or $C_4$), such as cyclopropyl and cyclobutyl.

"Heterocyclic ring" refers to saturated heterocyclic ring of the number of carbon atoms specified (i.e., $C_3$ or $C_4$), further comprising one additional heteroatoms selected from N, O, and S.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

EXAMPLES

Example 1. Synthesis of (S)-3-(6-(difluoromethoxy)-pyridin-3-yl)-3-(2-oxo-3-(3-(5,6,7,8-tetrahydro-1,8-naphthyridin-2-yl)propyl)imidazolidin-1-yl) propanoic acid (Compound A1)

Compound A1 is made using a convergent synthesis scheme as shown in Scheme 1: fragment 6b is reacted with fragment 9 to form compound 10, which is further reacted in three steps to form Compound A1.

Synthesis of Fragment 6b tert-butyl 2-oxopyrrolidine-1-carboxylate (2a)

To a stirred solution of compound 1a (10.0 g, 117 mmol, 1.0 equiv.) in DCM, $(Boc)_2O$ (25.5 g, 117 mmol, 1.00 equiv.) and DMAP (0.022 g, 0.180 mmol, 0.001 equiv.) were added at RT and stirred for 12 h. After consumption of the starting material (monitored by TLC), volatiles were removed under reduced pressure to afford compound 2a (19.6 g, 90.3%) as a brown syrup.

TLC: 50% EtOAc/Hexane ($R_f$: 0.40)
$^1$H NMR (400 MHz, $CDCl_3$): δ 3.74 (t, J=6.8 Hz, 2H), 2.50 (t, J=8.0 Hz, 2H), 2.01 (t, J=7.6 Hz, 2H), 1.52 (s, 9H)

tert-butyl (5-(dimethoxyphosphoryl)-4-oxopentyl)carbamate (3a)

To a stirred solution of $iPr_2NH$ (2.99 mL, 21.8 mmol, 1.35 equiv.) in THF, cooled to −10° C., hexyl lithium (8.79 mL, 20.0 mmol, 1.24 equiv.) was slowly added. The reaction mixture was cooled to −60° C., dimethylmethyl phosphonate (2.20 mL, 20.9 mmol, 1.29 equiv.) was added and stirred for 1 h. Then the temperature was raised to −40° C., and compound 2a (3.0 g, 16.2 mmol, 1.0 equiv.) was introduced to the reaction mixture and stirring was continued for further 1 h. After consumption of the starting material, 2N $H_2SO_4$ solution (20 mL) was added slowly to the reaction and stirred at 0° C. for 15 minutes. The aqueous layer was extracted with EtOAc (2×25 mL). The combined organic extracts were washed with water (25 mL), brine (25 ml), dried over $Na_2SO_4$, filtered and evaporated under reduced pressure to afford compound 3a as a brown liquid (5.0 g, crude).

TLC: 80% EtOAc/Hexane ($R_f$: 0.30)
$^1$H NMR (400 MHz, $CDCl_3$): δ 4.85 (brs, 1H, Exc), 3.80-3.72 (m, 8H), 3.13-3.07 (m, 2H), 2.67 (t, J=6.8 Hz, 2H), 1.87-1.76 (m, 2H), 1.43 (s, 9H)
LC-MS: m/z=308.3 [M+H]$^+$ at RT 2.67 (99.1% purity)

tert-butyl (3-(1,8-naphthyridin-2-yl)propyl)carbamate (5a)

To a stirred solution of compound 4a (0.500 g, 4.09 mmol, 1.0 equiv.) and compound 3a (1.26 g, crude, 1.0 equiv.) in MeOH (9.17 mL), 50% NaOH solution (0.314 mL) was added and the reaction mixture was stirred at 50° C. for 10 h. After consumption of the starting material (by TLC), volatiles were removed, crude residue was diluted with EtOAc (15 mL) and the organic layer was washed with water (2×15 mL). The separated organic layer was dried over $Na_2SO_4$, filtered and concentrated under reduced pressure to afford brown syrup, which was purified by column chromatography on neutral alumina (80% EtOAc: Hexane) to provide compound 5a (0.980 g, 83.3%) as an off-white solid.

TLC: EtOAc $^1$H NMR (500 MHz, $CDCl_3$): δ 9.09 (s, 1H), 8.17-8.15 (m, 1H), 8.10 (d, J=8.0 Hz, 1H), 7.45 (t, J=8.0 Hz, 1H), 7.41 (t, J=15.0, 1H), 4.76 (brs, 1H, Exc), 3.25-3.21 (m, 2H), 3.09 (t, J=10.0 Hz, 2H), 2.14-2.08 (m, 2H), 1.42 (s, 9H)

LC-MS: m/z=288 [M−H]$^-$ at RT 2.86 (94.7%)

tert-butyl (3-(5,6,7,8-tetrahydro-1,8-naphthyridin-2-yl)propyl)carbamate (S-024)

To a stirred solution of compound 5a (0.25 g, 0.87 mmol, 1.00 equiv.) in MeOH (5 mL), Rh/C (catalytic, 5 wt %) was added under $N_2$ atmosphere and stirred at RT for 8 h under hydrogen (balloon pressure) atmosphere. After completion of the starting material, the reaction mixture was filtered through pad of CELITE®, washed with MeOH (5 mL). The filtrate was evaporated under reduced pressure to afford compound S-024 (0.18 g, 71.1%) as a white solid.

TLC: EtOAc $^1$H NMR (400 MHz, $CDCl_3$): δ 7.05 (d, J=7.6 Hz, 1H), 6.34 (d, J=7.2 Hz, 1H), 5.44 (s, 1H), 4.78 (brs, 1H, Exc), 3.41-3.38 (m, 2H), 3.16 (d, J=6.0 Hz, 2H), 2.68 (t, J=6.0 Hz, 2H), 2.59 (t, J=7.6 Hz, 2H), 1.93-1.81 (m, 4H), 1.44 (s, 9H)

LC-MS: m/z=292.3 [M+H]$^+$ at RT 3.41 (97.9% purity)

3-(5,6,7,8-tetrahydro-1,8-naphthyridin-2-yl)propan-1-amine (6b)

To a stirred solution of S-024 (0.25 g, 0.85 mmol, 1.00 equiv.) in DCM (5 mL), cooled to 0° C., TFA (0.13 mL, 1.69 mmol, 2.00 equiv.) was added. The reaction was warmed to RT and stirred for 4 h. After consumption of the starting material (by TLC), the reaction mixture was concentrated under reduced pressure to afford crude compound 6b (0.30 g) as a thick syrup which was used in the next step without purification.

Synthesis of Fragment 9 and Completion of the Synthesis 5-bromo-2-(difluoromethoxy)pyridine (2)

To a stirred solution of compound 1 (4.50 g, 25.8 mmol, 1.0 equiv.) in anhydrous MeCN (80 mL), sodium 2-chloro-2,2-difluoroacetate (4.89 g, 31.0 mmol, 1.20 equiv.) was added at RT and stirred at 70° C. for 48 h. After consumption of the starting material (by TLC), the reaction mixture was brought to RT and diluted with $NH_4Cl$ solution (30 mL). The aqueous layer was extracted with EtOAc (2×40 mL). The combined organic layers were washed with brine solution (2×50 mL), dried over anhydrous $Na_2SO_4$, filtered and concentrated under reduced pressure to give the crude compound which was purified by column chromatography (2% EtOAc/hexane) to afford compound 2 (3.2 g, 57%) as pale yellow syrup.

TLC: 5% EtOAc/Hexane ($R_f$: 0.5) z $^1$H NMR (400 MHz, $CDCl_3$): δ 8.25 (d, J=2.8 Hz, 1H), 7.82 (dd, J=2.4, 6.4 Hz, 1H), 7.40 (t, J=72.8 Hz, 1H), 6.83 (d, J=8.8 Hz, 1H)

LC-MS: m/z=224.7 [M+H]$^+$ at RT 4.22 (98.2% purity)

(E)-tert-butyl 3-(6-(difluoromethoxy)pyridin-3-yl)acrylate (3)

To a stirred solution of tert-butyl acrylate (9.99 g, 78.1 mmol, 3.50 equiv.), $Et_3N$ (8.5 mL, 60.2 mmol, 2.70 equiv.), N-methyl pyrrolidine (20 mL), Tritolylphosphine (1.17 g, 3.52 mmol, 0.16 equiv.) followed by $Pd(OAc)_2$ (0.50 g, 2.22 mmol, 0.09 equiv.) were added. The temperature was gradually raised to 90° C. and compound 2 (5.00 g, 22.3 mmol, 1.0 equiv.) in NMP (10 mL) was added drop wise and stirred at 90° C. for 12 h. After consumption of the starting material (by TLC), the reaction mixture was filtered through pad of CELITE® and washed with EtOAc (50 mL). The combined filtrate was washed with cold water (2×50 mL) followed by NaOCl (50 mL), brine solution (50 mL). The organic layer was dried over anhydrous $Na_2SO_4$, filtered and concentrated under reduced pressure to give the crude residue which was purified by column chromatography (3% EtOAc/hexane) to afford compound 3 (4.0 g, 66%) as yellow solid.

TLC: 5% EtOAc/Hexane ($R_f$: 0.5)

$^1$H NMR (400 MHz, $CDCl_3$): δ 8.28 (d, J=2.4 Hz, 1H), 7.88 (dd, J=2.0, 6.4 Hz, 1H), 7.56 (d, J=16.0 Hz, 1H), 7.55 (t, J=45.6 Hz, 1H), 6.91 (d, J=8.4 Hz, 1H), 6.34 (d, J=16.0 Hz, 1H), 1.53 (s, 9H)

LC-MS: m/z=272 [M+H]$^+$ at RT 4.16 (99.5% purity)

(S)-tert-butyl 3-(benzyl ((R)-1-phenylethyl)amino)-3-(6-methoxypyridin-3-yl)propanoate (5)

To a stirred solution of compound 4 (0.39 g, 1.85 mmol, 2.0 equiv.) in THF (5 mL), cooled to −30° C., n-BuLi (0.66 mL, 1.65 mmol, 1.79 equiv.) was added and then cooled to −78° C. Compound 3 (0.25 g, 0.92 mmol, 1.0 equiv.) dissolved in THF (3 mL) was added to the reaction mixture, stirred for 30 min and quenched with saturated ammonium chloride. The reaction mixture was extracted with EtOAc (2×20 mL). The combined organic extracts were washed with 10% AcOH, brine solution which was dried over anhydrous $Na_2SO_4$, filtered and concentrated under reduced pressure to give the crude compound (mixture of 3 and 5, 0.17 g) as thick syrup, which was directly used in the next step.

TLC: 5% EtOAc/Hexane ($R_f$: 0.5)

LC-MS: m/z=483 [M+H]$^+$ at RT 4.66 (75.1% purity)

Synthesis of (S)-tert-butyl 3-amino-3-(6-(difluoromethoxy)pyridin-3-yl)propanoate (S-029)

To a stirred solution of compound 5 (0.80 g, crude mixture) in EtOAc (5 mL) and AcOH (0.5 mL), 20% $Pd(OH)_2$ (50 mg) was added under $N_2$ atmosphere. The reaction mixture was stirred under $H_2$ atmosphere (40 psi) at RT for 2 h. After consumption of the starting material (monitored by TLC), the reaction mixture was filtered through a pad of CELITE®. Filtrate was concentrated under reduced pressure to afford crude compound which was purified by column chromatography (2% MeOH/DCM) to furnish S-029 (0.3 g, 63%) as yellow syrup.

TLC: 5% MeOH/DCM (R$_f$: 0.3)

$^1$H NMR (400 MHz, CDCl$_3$): δ 8.17 (d, J=2.8 Hz, 1H), 7.78 (dd, J=2.4, 6.4 Hz, 1H), 7.44 (t, 73.2 Hz, 1H), 6.88 (d, J=8.4 Hz, 1H), 4.43-4.40 (m, 1H), 2.65-2.56 (m, 2H), 1.42 (s, 9H)

LC-MS: m/z=274 [M+H]$^+$ at RT 2.76 (99.8% purity)

(S,E)-tert-Butyl 3-(6-(tert-butoxy)pyridin-3-yl)-3-((2,2-dimethoxyethylidene)amino)propanoate (7)

To a stirred solution of dimethoxy acetaldehyde (0.44 mL, 2.50 mmol, 1.20 equiv., 60% in water) in DCM (10 mL), cooled to 0° C., anhydrous MgSO$_4$ (10 g) was added followed by S-029 (600 mg, 2.08 mmol, 1.0 equiv.) in DCM (5 mL). The reaction was continued at RT for 2 h and filtered through a pad of CELITE®, the filtrate was concentrated under reduced pressure to afford compound 7 (650 mg, crude) as a yellow liquid which was used in the next step without any purification.

TLC: 5% MeOH/DCM (R$_f$: 0.5)

(S)-tert-butyl 3-(6-(difluoromethoxy)pyridin-3-yl)-3-((2,2-dimethoxyethyl)amino)propanoate (8)

To a stirred solution of compound 7 (0.65 g, crude, 1.0 equiv.) in MeOH (7 mL), cooled to 0° C., NaBH(CN)$_3$ (0.13 g, 2.09 mmol, 1.20 equiv.) was added and the reaction mixture was stirred at RT for 2 h. After consumption of the starting material (by TLC), MeOH was removed under reduced pressure to give the crude residue which was diluted with water (10 mL) and extracted with EtOAc (2×10 ml). The combined organic extracts were dried over anhydrous Na$_2$SO$_4$, filtered and concentrated under reduced pressure to give the crude material which was purified by column chromatography (2% MeOH/DCM) to afford compound 8 (0.52 g, 79%) as a thick syrup.

TLC: 5% MeOH/DCM (R$_f$: 0.7)

$^1$H NMR (400 MHz, CDCl$_3$): δ 8.13 (d, J=2.0 Hz, 1H), 7.75 (dd, J=2.4, 6.0 Hz, 1H), 7.44 (t, J=73.2 Hz, 1H), 6.87 (d, J=8.4 Hz, 1H), 4.43-4.37 (m, 2H), 4.06-4.02 (m, 1H), 3.60-3.54 (m, 2H), 3.35 (s, 3H) 3.31 (s, 3H), 2.66-2.57 (m, 2H), 1.39 (s, 9H)

LC-MS: m/z=377 [M+H]$^+$ at RT 2.96 (92.3% purity)

(S)-tert-butyl 3-(6-(difluoromethoxy)pyridin-3-yl)-3-(1-(2,2-dimethoxyethyl)-3-(3-(5,6,7,8-tetrahydro-1,8-naphthyridin-2-yl)propyl)ureido)propanoate (10)

To a stirred solution of compound 8 (375 mg, 0.99 mmol, 1.0 equiv.) in dry DCM (5 mL), cooled to 0° C., triphosgene (1.50 mL, 2.99 mmol, 3.00 equiv., 20% in PhMe) followed by Et$_3$N (0.30 mL, 2.09 mmol, 2.10 equiv) were added. The reaction mixture was slowly brought to RT and stirred for 2 h. After completion of the starting material, volatiles were evaporated to afford the crude compound 9, which was used directly in the next step without purification. A solution of compound 9 in DCE (2 mL) was added to a solution of compound 6b (400 mg, 1.32 mmol, 1.32 equiv.) in DCM (5 mL), Et$_3$N (0.55 mL, 3.98 mmol, 4.00 equiv) at 0° C. and stirred at RT for 4 h. After consumption of the starting material (monitored by TLC), the reaction mixture was concentrated under reduced pressure to give the crude residue which was purified by column chromatography (2% MeOH/DCM) to afford compound 10 (0.40 g, 67%) as a thick syrup.

TLC: 5% MeOH/DCM (R$_f$: 0.2)

$^1$H NMR (400 MHz, CDCl$_3$): δ 8.13 (d, J=2.8 Hz, 1H), 7.79 (dd, J=2.4, 6.4 Hz, 1H), 7.62 (tt, J=72.8 Hz, 1H), 7.12 (d, J=6.4 Hz, 1H), 6.86 (d, J=8.4 Hz, 1H), 6.36 (d, J=3.6 Hz, 1H), 6.22 (t, J=4.8 Hz, 1H), 5.75 (t, J=7.6 Hz, 1H), 4.26 (t, J=5.2 Hz, 1H), 3.45-3.38 (m, 8H), 3.27-3.13 (m, 3H), 2.99-2.93 (m, 2H), 2.71-2.59 (m, 5H), 1.93-1.83 (m, 5H), 1.39 (s, 9H)

LC-MS: m/z=594 [M+H]$^+$ at RT 3.42 (88.1% purity)

(S)-tert-Butyl 3-(6-(difluoromethoxy)pyridin-3-yl)-3-(2-oxo-3-(3-(5,6,7,8-tetrahydro-1,8-naphthyridin-2-yl)propyl)-2,3-dihydro-1H-imidazol-1-yl)propanoate (11)

To a stirred solution of compound 10 (0.20 g, 0.34 mmol, 1.0 equiv.) in THF (4 mL), at −10° C., 1 M sulfuric acid (0.8 mL) was added. The reaction was slowly warmed to RT and stirred for 10 h. After consumption of the starting material (monitored by LCMS), THF was removed and the crude residue was neutralized with sodium hydroxide (50 wt %) till pH~7. The aqueous layer was extracted with 5% MeOH/DCM (3×20 mL) and the combined organic extracts were dried over anhydrous Na$_2$SO$_4$, filtered and concentrated under reduced pressure to furnish compound 11 (0.22 g, crude) as a syrup.

TLC: 10% MeOH/DCM (R$_f$: 0.5)

LC-MS: m/z=530 [M+H]$^+$ at RT 4.06 (72.8% purity)

(S)-tert-Butyl 3-(6-(difluoromethoxy)pyridin-3-yl)-3-(2-oxo-3-(3-(5,6,7,8-tetrahydro-1,8-naphthyridin-2-yl)propyl) imidazolidin-1-yl)propanoate (12)

To a stirred solution of compound 11 (0.45 g, crude, 1.0 equiv.) in EtOH (8 mL), 20% Pd/C (200 mg) was added under N$_2$ atmosphere. The reaction mixture was stirred under H$_2$ atmosphere (40 psi) at RT for 36 h. After consumption of the starting material the reaction mixture was filtered through a pad of CELITE®, and the filtrate was concentrated under reduced pressure to afford crude compound 12, which was purified by chiral preparative HPLC to afford compound 12 (450 mg, crude) as an off-white solid.

TLC: 10% MeOH/DCM (R$_f$: 0.5)

LC-MS: m/z=532.6 [M+H]$^+$ at RT 3.99 (80.1% purity)

(S)-3-(6-(difluoromethoxy)pyridin-3-yl)-3-(2-oxo-3-(3-(5,6,7,8-tetrahydro-1,8-naphthyridin-2-yl)propyl) imidazolidin-1-yl)propanoic acid (Compound A1)

To a stirred solution of compound 2 (0.40 g, crude, 1.0 equiv.) in DCM (2 mL), cooled to −10° C., TFA (0.5 mL) was added under N$_2$ atmosphere. The reaction was slowly brought to RT and stirred for 2 h; after consumption of the starting material, volatiles were evaporated to afford crude (400 mg) compound, which was purified by chiral preparative HPLC to afford compound A1 as an off-white solid.

TLC: 10% MeOH/DCM (R$_f$: 0.3)

$^1$H NMR (400 MHz, CD$_3$OD): δ 8.20 (d, J=2.4 Hz, 1H), 7.85 (dd, J=2.4, 6.4 Hz, 1H), 7.53 (t, J=2.4 Hz, 1H), 7.50 (d, J=7.2 Hz, 1H), 6.98 (d, J=8.4 Hz, 1H), 6.57 (d, J=7.2 Hz, 1H), 5.51 (dd, J=3.6, 8.0 Hz, 1H), 3.68-3.61 (m, 1H), 3.52-3.46 (m, 3H), 3.38 (m, 1H), 3.24-3.17 (m, 1H), 3.07-2.98 (m, 2H), 2.90-2.62 (m, 6H), 2.09-1.81 (m, 4H).

LC-MS: m/z=476 [M+H]$^+$ at RT 2.78 (97.9% purity)

HPLC purity: 96.4%; Chiral Purity: 99%

The compounds of the present invention described in Examples 2-7 in which Z is —CH$_2$CH$_2$CH$_2$— were synthesized using the general reaction scheme shown in Scheme 2. Dimethyl (2-oxo-6-(5,6,7,8-tetrahydro-1,8-naphthyridin-2-yl)hexyl)phosphonate was added to the fluorinated nitrogen heterocycle (Q) aldehyde to form the hept-1-en-3-one. The hept-1-en-3-one was reduced to the corresponding hept-1-en-3-ol using lithium aluminum hydride or sodium borohydride. The hept-1-en-3ol was then reacted with proprionic acid in 1,1,1-triethoxyethane and the resulting crude rearrangement product was reduced with hydrogen and palladium on carbon catalyst to the corresponding olefin reduction product which was then reacted with aqueous base to form the final nonanoic acid compounds.

Example 2. Synthesis of 9-(5,6,7,8-tetrahydro-1,8-naphthyridin-2-yl)-3-(2-(trifluoromethyl)pyrimidin-5-yl)nonanoic acid (Compound A2)

(E)-7-(5,6,7,8-tetrahydro-1,8-naphthyridin-2-yl)-1-(2-(trifluoromethyl)pyrimidin-5-yl)hept-1-en-3-one

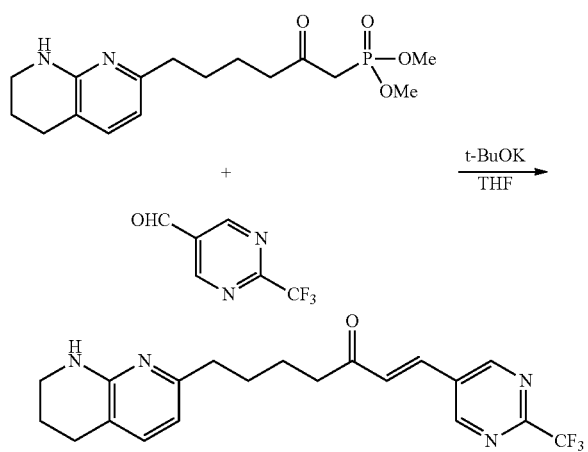

Under nitrogen, to dimethyl (2-oxo-6-(5,6,7,8-tetrahydro-1,8-naphthyridin-2-yl)hexyl)phosphonate (3.40 g, 10.0 mmol, 1.00 equiv; Coleman, P. J. et al., J. Med. Chem. 2004, 47:4829-4837) in THF (10 mL) at 23° C. was added 2-(trifluoromethyl)pyrimidine-5-carbaldehyde (1.76 g, 10.0 mmol, 1.00 equiv) and t-BuOK (1.01 g, 9.00 mmol, 0.900 equiv). After stirring for 10 min at 23° C., the reaction mixture was directly loaded on silica gel and purified by column chromatography on silica gel eluting with $CH_2Cl_2$/MeOH to afford 2.10 g of the title compound (54% yield).

$^1$H NMR (300 MHz, CDCl$_3$, 23° C., δ): 9.03 (s, 2H), 7.50 (d, J=16.2 Hz, 1H), 7.07 (d, J=7.2 Hz, 1H), 6.93 (d, J=16.2 Hz, 1H), 6.35 (d, J=7.2 Hz, 1H), 5.17 (br s, 1H), 3.42-3.37 (m, 2H), 2.79-2.64 (m, 4H), 2.62-2.55 (m, 2H), 1.95-1.85 (m, 2H), 1.77-1.66 (m, 4H). $^{19}$F NMR (282 MHz, CDCl$_3$, 23° C., δ): −70.3 (s, 3F).

(E)-7-(5,6,7,8-tetrahydro-1,8-naphthyridin-2-yl)-1-(2-(trifluoromethyl)pyrimidin-5-yl)hept-1-en-3-ol

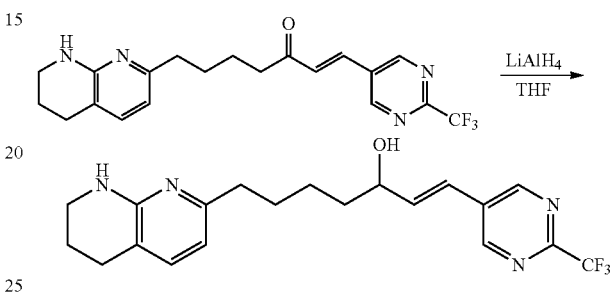

Under nitrogen, to (E)-7-(5,6,7,8-tetrahydro-1,8-naphthyridin-2-yl)-1-(2-(trifluoromethyl)pyrimidin-5-yl)hept-1-en-3-one (1.20 g, 3.07 mmol, 1.00 equiv) in THF (15 mL) at −78° C. was added LiAlH$_4$ (1.0 M in THF, 3.07 mL, 3.07 mmol, 1.00 equiv). After stirring for 10 min at −78° C., H$_2$O (116 μL), 15% NaOH aq (116 μL) and H$_2$O (348 μL) were added sequentially to the reaction mixture. The reaction mixture was warmed to 23° C. and filtered through a pad of CELITE®. The filtrate was concentrated in vacuo and the residue was purified by column chromatography on silica gel eluting with $CH_2C_2$/MeOH to afford 560 mg of the title compound (46% yield).

$^1$H NMR (300 MHz, CDCl$_3$, 23° C., δ): 8.86 (s, 2H), 7.06 (d, J=7.2 Hz, 1H), 6.66 (d, J=16.2 Hz, 1H), 6.53 (dd, J=16.2 Hz, 4.5 Hz, 1H), 6.34 (d, J=7.2 Hz, 1H), 4.81 (br s, 1H), 4.50-4.40 (m, 1H), 3.42-3.37 (m, 2H), 2.70-2.50 (m, 4H), 1.96-1.40 (m, 8H). $^{19}$F NMR (282 MHz, CDCl$_3$, 23° C., δ): −70.1 (s, 3F).

9-(5,6,7,8-tetrahydro-1,8-naphthyridin-2-yl)-3-(2-(trifluoromethyl)pyrimidin-5-yl)nonanoic acid (Compound A2)

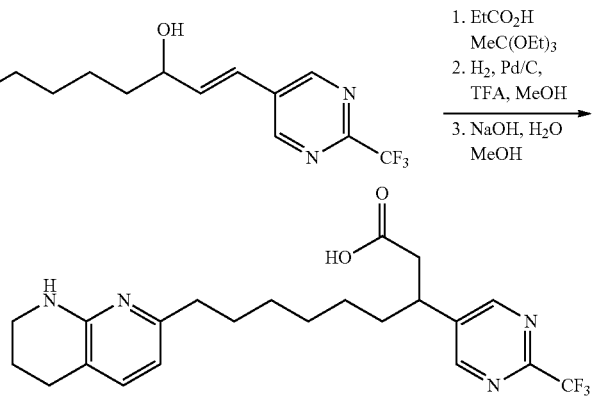

Under nitrogen, to (E)-7-(5,6,7,8-tetrahydro-1,8-naphthyridin-2-yl)-1-(2-(trifluoromethyl)pyrimidin-5-yl)hept-1-en-3-ol (560 mg, 1.43 mmol, 1.00 equiv) in MeC(OEt)₃ (14 mL) at 23° C. was added EtCO₂H (107 µL, 1.43 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C (103 mg, 0.0969 mmol, 6.78 mol %) and H₂ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (2.7 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO₃ aq (2×5 mL) and dried (MgSO₄). The filtrate was concentrated in vacuo and the residue was purified by column chromatography on silica gel eluting with CH₂Cl₂/MeOH to afford 280 mg of the title compound (45% yield over 3 steps).

$^1$H NMR (300 MHz, CDCl₃, 23° C., δ): 8.79 (s, 2H), 7.24 (d, J=7.2 Hz, 1H), 6.25 (d, J=7.2 Hz, 1H), 3.48-3.40 (m, 2H), 3.38-3.32 (m, 1H), 2.75-2.52 (m, 4H), 1.95-1.80 (m, 4H), 1.75-1.58 (m, 4H), 1.40-1.18 (m, 6H). $^{19}$F NMR (282 MHz, CDCl₃, 23° C., δ): −70.1 (s, 3F).

Example 3. Synthesis of 3-(6-(difluoromethoxy)pyridin-3-yl)-9-(5,6,7,8-tetrahydro-1,8-naphthyridin-2-yl)nonanoic acid (Compound A3)

6-(difluoromethoxy)nicotinaldehyde

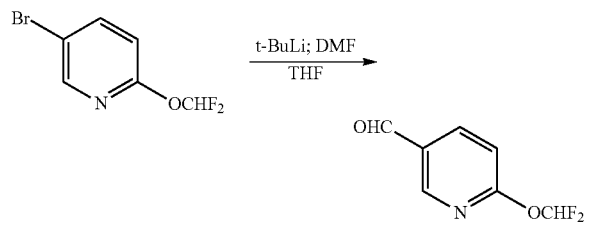

Under nitrogen, to 5-bromo-2-(difluoromethoxy)pyridine (448 mg, 2.00 mmol, 1.00 equiv; Ando, M. et al., *Org. Lett.* 2006, 8:3805-3808) in THF (10 mL) at −78° C. was added t-BuLi (1.7 M in pentane, 2.35 mL, 4.00 mmol, 2.00 equiv) dropwise over 5 min. After stirring for 20 min at −78° C., DMF (0.54 mL, 7.0 mmol, 3.5 equiv) was added to the reaction mixture. After stirring for 20 min at −78° C., 1N HCl aq (10 mL) was added to the reaction mixture and the reaction mixture was warmed to 23° C. The phases were separated and the aqueous phase was extracted with EtOAc (3×5 mL). The combined organic phases were washed with brine (10 mL) and dried (MgSO₄). The filtrate was concentrated in vacuo and the residue was purified by column chromatography on silica gel eluting with hexanes/EtOAc to afford 105 mg of the title compound (30% yield).

$^1$H NMR (300 MHz, CDCl₃, 23° C., δ): 10.05 (s, 1H), 8.69 (d, J=2.1 Hz, 1H), 8.24 (dd, J=8.4 Hz, 2.4 Hz, 1H), 7.56 (t, J=72.3 Hz, 1H), 7.04 (d, J=8.4 Hz, 1H). $^{19}$F NMR (282 MHz, CDCl₃, 23° C., δ): −89.8 (d, J=72.3 Hz, 2F).

(E)-1-(6-(difluoromethoxy)pyridin-3-yl)-7-(5,6,7,8-tetrahydro-1,8-naphthyridin-2-yl)hept-1-en-3-one

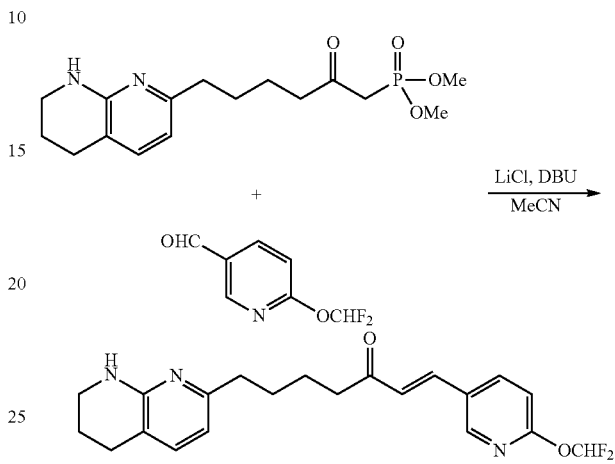

Under nitrogen, to dimethyl (2-oxo-6-(5,6,7,8-tetrahydro-1,8-naphthyridin-2-yl)hexyl)phosphonate (1.57 g, 4.62 mmol, 1.00 equiv) in MeCN (11 mL) at 23° C. was added 6-(difluoromethoxy)nicotinaldehyde (800 mg, 4.62 mmol, 1.00 equiv), LiCl (196 mg, 4.62 mmol, 1.00 equiv) and DBU (0.725 mL, 4.85 mmol, 1.05 equiv). After stirring for 1 hr at 50° C., the reaction mixture was cooled to 23° C. and was filtered through a pad of CELITE®. The filtrate was concentrated in vacuo and the residue was purified by column chromatography on silica gel eluting with CH₂Cl₂/MeOH to afford 1.27 g of the title compound (71% yield).

$^1$H NMR (300 MHz, CDCl₃, 23° C., δ): 8.32 (d, J=2.4 Hz, 1H), 7.92 (dd, J=8.4 Hz, 2.4 Hz, 1H), 7.49 (t, J=72.3 Hz, 1H), 7.47 (d, J=16.2 Hz, 1H), 7.06 (d, J=7.2 Hz, 1H), 6.93 (d, J=8.7 Hz, 1H), 6.70 (d, J=16.2 Hz, 1H), 6.35 (d, J=7.2 Hz, 1H), 4.89 (br s, 1H), 3.42-3.36 (m, 2H), 2.76-2.64 (m, 4H), 2.62-2.56 (m, 2H), 1.94-1.85 (m, 2H), 1.80-1.66 (m, 4H). $^{19}$F NMR (282 MHz, CDCl₃, 23° C., δ): −89.2 (d, J=72.3 Hz, 2F).

(E)-1-(6-(difluoromethoxy)pyridin-3-yl)-7-(5,6,7,8-tetrahydro-1,8-naphthyridin-2-yl)hept-1-en-3-ol

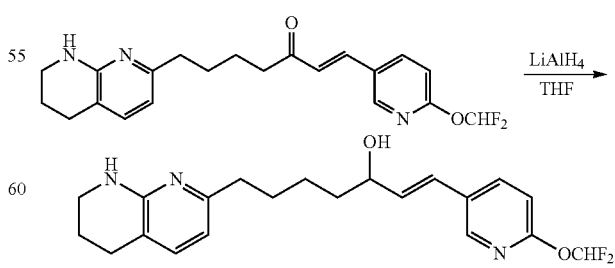

Under nitrogen, to (E)-1-(6-(difluoromethoxy)pyridin-3-yl)-7-(5,6,7,8-tetrahydro-1,8-naphthyridin-2-yl)hept-1-en-3-one (1.27 g, 3.28 mmol, 1.00 equiv) in THF (33 mL) at 0°

C. was added LiAlH₄ (1.0 M in THF, 3.28 mL, 3.28 mmol, 1.00 equiv). After stirring for 10 min at 0° C., H₂O (124 μL), 15% NaOH aq (124 μL) and H₂O (372 μL) were added sequentially to the reaction mixture. The reaction mixture was warmed to 23° C. and filtered through a pad of CELITE®. The filtrate was concentrated in vacuo and the residue was purified by column chromatography on silica gel eluting with CH₂Cl₂/MeOH to afford 1.05 g of the title compound (82% yield).

¹H NMR (300 MHz, CDCl₃, 23° C., δ): 8.22 (d, J=2.4 Hz, 1H), 7.84 (dd, J=8.4 Hz, 2.4 Hz, 1H), 7.49 (t, J=72.3 Hz, 1H), 7.05 (d, J=7.2 Hz, 1H), 6.88 (d, J=8.7 Hz, 1H), 6.66 (d, J=16.2 Hz, 1H), 6.55 (dd, J=16.2 Hz, 4.5 Hz, 1H), 6.33 (d, J=7.2 Hz, 1H), 4.84 (br s, 1H), 4.52-4.43 (m, 1H), 3.40-3.37 (m, 2H), 2.72-2.51 (m, 4H), 1.95-1.40 (m, 8H). ¹⁹F NMR (282 MHz, CDCl₃, 23° C., δ): −89.0 (d, J=72.5 Hz, 2F).

3-(6-(difluoromethoxy)pyridin-3-yl)-9-(5,6,7,8-tetrahydro-1,8-naphthyridin-2-yl)nonanoic acid (Compound A3)

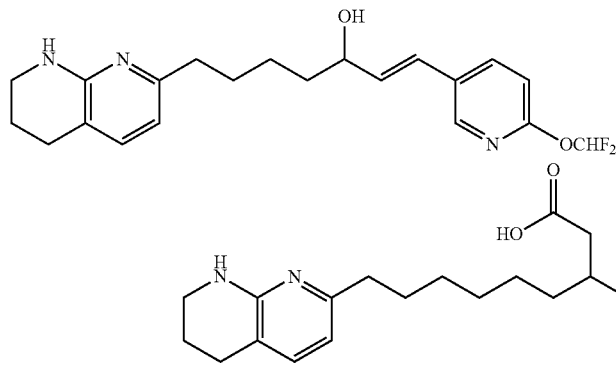

Under nitrogen, to (E)-1-(6-(difluoromethoxy)pyridin-3-yl)-7-(5,6,7,8-tetrahydro-1,8-naphthyridin-2-yl)hept-1-en-3-ol (1.05 g, 2.70 mmol, 1.00 equiv) in MeC(OEt)₃ (27 mL) at 23° C. was added EtCO₂H (201 μL, 2.70 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C (176 mg, 0.165 mmol, 6.11 mol %) and H₂ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (4.4 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO₃ aq (2×5 mL) and dried (MgSO₄). The filtrate was concentrated in vacuo and the residue was purified by column chromatography on silica gel eluting with CH₂C₂/MeOH to afford 400 mg of the title compound (34% yield over 3 steps).

¹H NMR (300 MHz, CDCl₃, 23° C., δ): 8.06 (d, J=2.4 Hz, 1H), 7.66 (dd, J=8.4 Hz, 2.4 Hz, 1H), 7.43 (t, J=72.3 Hz, 1H), 7.20 (d, J=8.7 Hz, 1H), 6.84 (d, J=7.2 Hz, 1H), 6.25 (d, J=7.2 Hz, 1H), 3.46-3.40 (m, 2H), 3.38-3.28 (m, 1H), 2.79-2.40 (m, 4H), 1.95-1.80 (m, 4H), 1.75-1.62 (m, 4H), 1.40-1.20 (m, 6H). ¹⁹F NMR (282 MHz, CDCl₃, 23° C., δ): −88.3 (d, J=72.5 Hz, 2F).

Example 4. Synthesis of 3-(6-fluoroquinolin-3-yl)-9-(5,6,7,8-tetrahydro-1,8-naphthyridin-2-yl)nonanoic acid (Compound A4)

6-fluoroquinoline-3-carbaldehyde

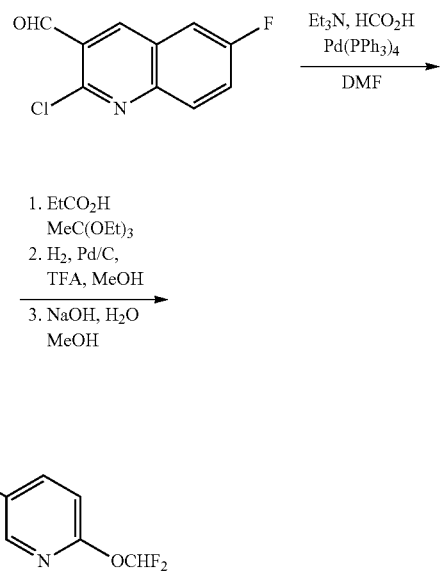

-continued

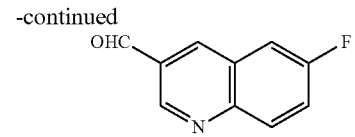

Under nitrogen, to 2-chloro-6-fluoroquinoline-3-carbaldehyde (2.03 g, 9.68 mmol, 1.00 equiv) in DMF (10 mL) at 23° C. was added triethylamine (16.2 mL, 116 mmol, 12.0 equiv), Pd(PPh₃)₄ (559 mg, 0.484 mmol, 5.00 mol %), and formic aid (1.29 mL, 34.2 mmol, 5.40 equiv). After stirring for 1 hr at 100° C., the reaction mixture was cooled to 23° C. and water (40 mL) and EtOAc (30 mL) was added. The phases were separated and the aqueous phase was extracted with EtOAc (3×30 mL). The combined organic phases were washed with brine (50 mL) and dried (MgSO₄). The filtrate was concentrated in vacuo and the residue was purified by column chromatography on silica gel eluting with hexanes/EtOAc to afford 734 mg of the title compound (43% yield).

¹H NMR (300 MHz, CDCl₃, 23° C., δ): 10.27 (s, 1H), 9.34 (d, J=2.1 Hz, 1H), 8.60 (d, J=1.8 Hz, 1H), 8.21 (dd, J=9.0 Hz, 4.8 Hz, 1H), 7.70-7.60 (m, 2H). ¹⁹F NMR (282 MHz, CDCl₃, 23° C., δ): −110.8 (m, 1F).

(E)-1-(6-fluoroquinolin-3-yl)-7-(5,6,7,8-tetrahydro-1,8-naphthyridin-2-yl)hept-1-en-3-one

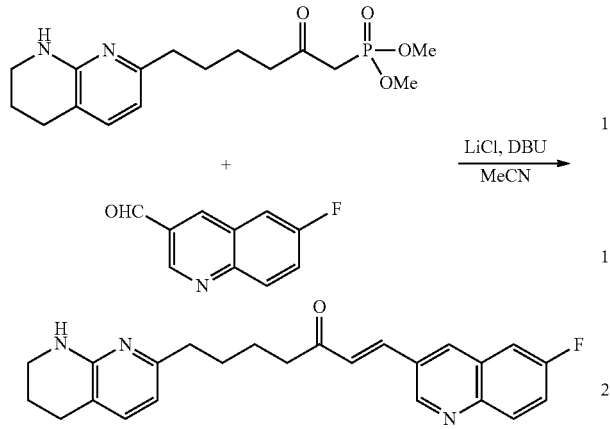

Under nitrogen, to dimethyl (2-oxo-6-(5,6,7,8-tetrahydro-1,8-naphthyridin-2-yl)hexyl)phosphonate (900 mg, 2.64 mmol, 1.10 equiv) in MeCN (22 mL) at 23° C. was added 6-fluoroquinoline-3-carbaldehyde (420 mg, 2.40 mmol, 1.00 equiv), LiCl (101 mg, 2.40 mmol, 1.00 equiv) and DBU (0.377 mL, 2.52 mmol, 1.05 equiv). After stirring for 1 hr at 75° C., the reaction mixture was cooled to 23° C. and was filtered through a pad of CELITE®. The filtrate was concentrated in vacuo and the residue was purified by column chromatography on silica gel eluting with CH$_2$Cl$_2$/MeOH to afford 900 mg of the title compound (96% yield).

$^1$H NMR (300 MHz, CDCl$_3$, 23° C., δ): 9.06 (d, J=2.4 Hz, 1H), 8.21 (d, J=2.1 Hz, 1H), 8.11 (dd, J=10.6 Hz, 5.7 Hz, 1H), 7.66 (d, J=16.2 Hz, 1H), 7.58-7.43 (m, 2H), 7.06 (d, J=7.2 Hz, 1H), 6.96 (d, J=16.2 Hz, 1H), 6.37 (d, J=7.2 Hz, 1H), 4.76 (br s, 1H), 3.43-3.35 (m, 2H), 2.78-2.65 (m, 4H), 2.63-2.56 (m, 2H), 1.94-1.85 (m, 2H), 1.82-1.66 (m, 4H). $^{19}$F NMR (282 MHz, CDCl$_3$, 23° C., δ): −111.9 (m, 1F).

(E)-1-(6-fluoroquinolin-3-yl)-7-(5,6,7,8-tetrahydro-1,8-naphthyridin-2-yl)hept-1-en-3-ol

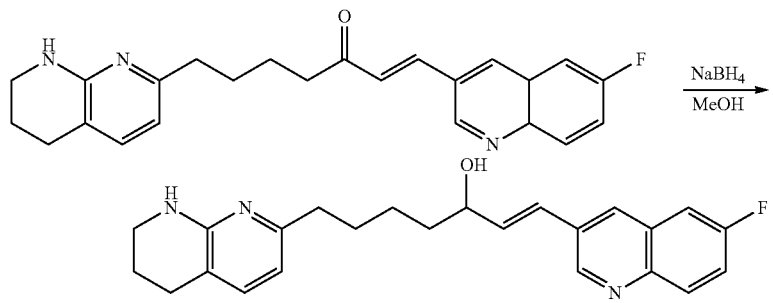

Under air, to (E)-1-(6-fluoroquinolin-3-yl)-7-(5,6,7,8-tetrahydro-1,8-naphthyridin-2-yl)hept-1-en-3-one (490 mg, 1.26 mmol, 1.00 equiv) in MeOH (29 mL) at 0° C. was added NaBH$_4$ (71.5 mg, 1.89 mmol, 1.5 equiv). After stirring for 1 hr at 0° C., 1N HCl aq (10 mL) was added to the reaction mixture and concentrated in vacuo to remove MeOH. The residue was neutralized with NaHCO$_3$ aq and EtOAc (10 mL) was added. The phases were separated and the aqueous phase was extracted with EtOAc (3×20 mL). The combined organic phases were washed with brine (30 mL) and dried (MgSO$_4$). The filtrate was concentrated in vacuo and the residue was purified by column chromatography on silica gel eluting with CH$_2$Cl$_2$/MeOH to afford 490 mg of the title compound (99% yield).

$^1$H NMR (300 MHz, CDCl$_3$, 23° C., δ): 8.95 (s, 1H), 8.06 (dd, J=10.6 Hz, 5.7 Hz, 1H), 7.99 (s, 1H), 7.50-7.40 (m, 2H), 7.06 (d, J=7.2 Hz, 1H), 6.75 (d, J=16.2 Hz, 1H), 6.49 (dd, J=16.2 Hz, 4.5 Hz, 1H), 6.34 (d, J=7.2 Hz, 1H), 4.94 (br s, 1H), 4.47-4.39 (m, 1H), 3.42-3.38 (m, 2H), 2.70-2.47 (m, 4H), 1.96-1.45 (m, 8H). $^{19}$F NMR (282 MHz, CDCl$_3$, 23° C., δ): −111.8 (m, 1F).

3-(6-fluoroquinolin-3-yl)-9-(5,6,7,8-tetrahydro-1,8-naphthyridin-2-yl)nonanoic acid (Compound A4)

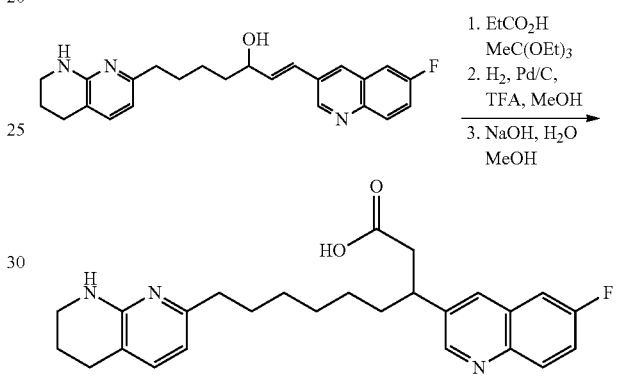

Under nitrogen, to (E)-1-(6-fluoroquinolin-3-yl)-7-(5,6,7,8-tetrahydro-1,8-naphthyridin-2-yl)hept-1-en-3-ol (489 mg, 1.25 mmol, 1.00 equiv) in MeC(OEt)$_3$ (12 mL) at 23° C. was added EtCO$_2$H (93.3 μL, 1.25 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C (128 mg, 0.121 mmol, 9.68 mol %) and H$_2$ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (3.0 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO₃ aq (2×5 mL) and dried (MgSO₄). The filtrate was concentrated in vacuo and the residue was purified by column chromatography on silica gel eluting with CH₂Cl₂/MeOH to afford 500 mg of the title compound (92% yield over 3 steps).

¹H NMR (300 MHz, CD₃OD, 23° C., δ): 8.78 (s, 1H), 8.11 (s, 1H), 8.00-7.93 (m, 1H), 7.52-7.42 (m, 2H), 7.31 (d, J=7.2 Hz, 1H), 6.35 (d, J=7.2 Hz, 1H), 3.38-3.20 (m, 3H), 2.77-2.42 (m, 4H), 1.90-1.20 (m, 14H). ¹⁹F NMR (282 MHz, CD₃OD, 23° C., δ): −110.9 (m, 1F).

Example 5. Synthesis of 3-(7-fluoroquinolin-3-yl)-9-(5,6,7,8-tetrahydro-1,8-naphthyridin-2-yl)nonanoic acid (Compound A5)

(E)-1-(7-fluoroquinolin-3-yl)-7-(5,6,7,8-tetrahydro-1,8-naphthyridin-2-yl)hept-1-en-3-one

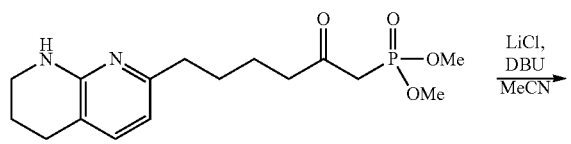

+

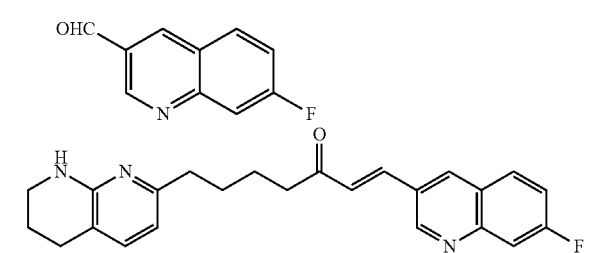

Under nitrogen, to dimethyl (2-oxo-6-(5,6,7,8-tetrahydro-1,8-naphthyridin-2-yl)hexyl)phosphonate (749 mg, 2.20 mmol, 1.10 equiv) in MeCN (22 mL) at 23° C. was added 7-fluoroquinoline-3-carbaldehyde (350 mg, 2.00 mmol, 1.00 equiv; Sato, I. et al., *Synthesis* 2004, 9:1419-1428), LiCl (84.8 mg, 2.00 mmol, 1.00 equiv) and DBU (0.314 mL, 2.10 mmol, 1.05 equiv). After stirring for 1 hr at 75° C., the reaction mixture was cooled to 23° C. and was filtered through a pad of CELITE®. The filtrate was concentrated in vacuo and the residue was purified by column chromatography on silica gel eluting with CH₂Cl₂/MeOH to afford 570 mg of the title compound (73% yield).

¹H NMR (300 MHz, CDCl₃, 23° C., δ): 9.10 (d, J=2.4 Hz, 1H), 8.28 (d, J=2.1 Hz, 1H), 7.87 (dd, J=9.0 Hz, 6.0 Hz, 1H), 7.74 (dd, J=9.9 Hz, 2.4 Hz, 1H), 7.69 (d, J=16.2 Hz, 1H), 7.42-7.33 (m, 1H), 7.11 (d, J=7.2 Hz, 1H), 6.94 (d, J=16.2 Hz, 1H), 6.37 (d, J=7.2 Hz, 1H), 5.41 (br s, 1H), 3.43-3.37 (m, 2H), 2.78-2.58 (m, 6H), 1.93-1.85 (m, 2H), 1.81-1.69 (m, 4H). ¹⁹F NMR (282 MHz, CDCl₃, 23° C., δ): −107.0 (m, 1F).

(E)-1-(7-fluoroquinolin-3-yl)-7-(5,6,7,8-tetrahydro-1,8-naphthyridin-2-yl)hept-1-en-3-ol

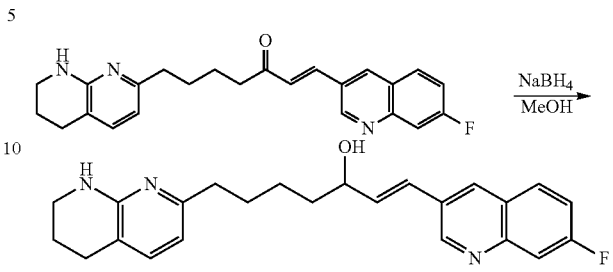

Under air, to (E)-1-(7-fluoroquinolin-3-yl)-7-(5,6,7,8-tetrahydro-1,8-naphthyridin-2-yl)hept-1-en-3-one (300 mg, 0.770 mmol, 1.00 equiv) in MeOH (8 mL) at 0° C. was added NaBH₄ (87.4 mg, 2.31 mmol, 3.00 equiv). After stirring for 30 min at 0° C., 1N HCl aq (10 mL) was added to the reaction mixture and concentrated in vacuo to remove MeOH. The residue was neutralized with NaHCO₃ aq and EtOAc (10 mL) was added. The phases were separated and the aqueous phase was extracted with EtOAc (3×20 mL). The combined organic phases were washed with brine (30 mL) and dried (MgSO₄). The filtrate was concentrated in vacuo and the residue was purified by column chromatography on silica gel eluting with CH₂C₂/MeOH to afford 210 mg of the title compound (70% yield).

¹H NMR (300 MHz, CDCl₃, 23° C., δ): 8.98 (s, 1H), 8.07 (s, 1H), 7.81 (dd, J=9.0 Hz, 6.0 Hz, 1H), 7.78 (dd, J=9.9 Hz, 2.4 Hz, 1H), 7.63 (br s, 1H), 7.39-7.28 (m, 1H), 6.78 (d, J=16.2 Hz, 1H), 6.47 (dd, J=16.2 Hz, 4.5 Hz, 1H), 6.36 (d, J=7.2 Hz, 1H), 4.48-4.41 (m, 1H), 3.48-3.41 (m, 2H), 2.79-2.67 (m, 4H), 1.97-1.48 (m, 8H). ¹⁹F NMR (282 MHz, CDCl₁₃, 23° C., δ): −109.9 (m, 1F).

3-(7-fluoroquinolin-3-yl)-9-(5,6,7,8-tetrahydro-1,8-naphthyridin-2-yl)nonanoic acid (Compound A5)

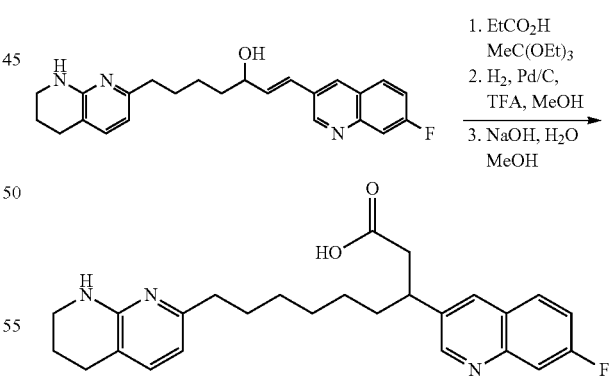

Under nitrogen, to (E)-1-(7-fluoroquinolin-3-yl)-7-(5,6,7,8-tetrahydro-1,8-naphthyridin-2-yl)hept-1-en-3-ol (730 mg, 1.71 mmol, 1.00 equiv) in MeC(OEt)₃ (17 mL) at 23° C. was added EtCO₂H (128 µL, 1.71 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C (125 mg, 0.117 mmol, 6.84 mol %) and H₂ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (3.0 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO₃ aq (2×5 mL) and dried (MgSO₄). The filtrate was concentrated in vacuo and the residue was purified by column chromatography on silica gel eluting with CH₂Cl₂/MeOH to afford 480 mg of the title compound (64% yield over 3 steps).

$^1$H NMR (300 MHz, CD₃OD, 23° C., δ): 8.79 (s, 1H), 8.21 (s, 1H), 8.00-7.91 (m, 1H), 7.62-7.57 (m, 1H), 7.48-7.38 (m, 2H), 6.47 (d, J=7.2 Hz, 1H), 3.48-3.30 (m, 3H), 2.80-2.52 (m, 4H), 1.90-1.20 (m, 14H). $^{19}$F NMR (282 MHz, CD₃OD, 23° C., δ): −111.9 (m, 1F).

Example 6. Synthesis of 3-(6,7-difluoroquinolin-3-yl)-9-(5,6,7,8-tetrahydro-1,8-naphthyridin-2-yl) nonanoic acid (Compound A6)

6,7-difluoroquinoline-3-carbaldehyde

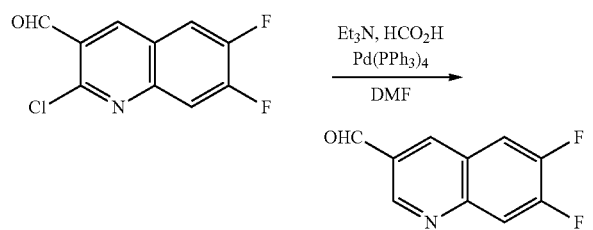

Under nitrogen, to 2-chloro-6,7-difluoroquinoline-3-carbaldehyde (1.44 g, 6.33 mmol, 1.00 equiv) in DMF (6.3 mL) at 23° C. was added triethylamine (10.6 mL, 76.0 mmol, 12.0 equiv), Pd(PPh₃)₄ (366 mg, 0.317 mmol, 5.00 mol %), and formic aid (1.29 mL, 34.2 mmol, 5.40 equiv). After stirring for 1 hr at 100° C., the reaction mixture was cooled to 23° C. and water (30 mL) and EtOAc (20 mL) was added. The phases were separated and the aqueous phase was extracted with EtOAc (3×20 mL). The combined organic phases were washed with brine (50 mL) and dried (MgSO₄). The filtrate was concentrated in vacuo and the residue was purified by column chromatography on silica gel eluting with hexanes/EtOAc to afford 500 mg of the title compound (41% yield).

$^1$H NMR (300 MHz, CDCl₃, 23° C., δ): 10.26 (s, 1H), 9.35 (d, J=1.2 Hz, 1H), 8.60 (d, J=1.5 Hz, 1H), 7.97 (dd, J=10.8 Hz, 7.5 Hz, 1H), 7.97 (dd, J=9.0 Hz, 8.7 Hz, 1H). $^{19}$F NMR (282 MHz, CDCl₃, 23° C., δ): −125.3 (m, 1F), −132.3 (m, 1F).

(E)-1-(6,7-difluoroquinolin-3-yl)-7-(5,6,7,8-tetrahydro-1,8-naphthyridin-2-yl)hept-1-en-3-one

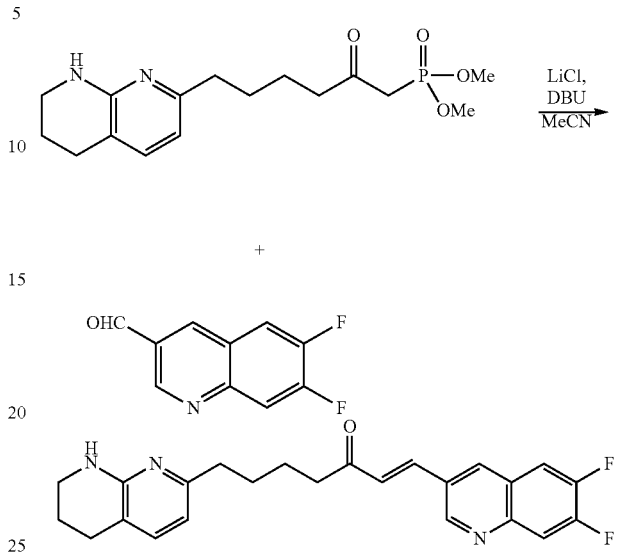

Under nitrogen, to dimethyl (2-oxo-6-(5,6,7,8-tetrahydro-1,8-naphthyridin-2-yl)hexyl)phosphonate (599 mg, 1.76 mmol, 1.10 equiv) in MeCN (5 mL) at 23° C. was added 6,7-difluoroquinoline-3-carbaldehyde (310 mg, 1.60 mmol, 1.00 equiv), LiCl (67.8 mg, 1.60 mmol, 1.00 equiv) and DBU (0.251 mL, 1.68 mmol, 1.05 equiv). After stirring for 1 hr at 75° C., the reaction mixture was cooled to 23° C. and was filtered through a pad of CELITE®. The filtrate was concentrated in vacuo and the residue was purified by column chromatography on silica gel eluting with CH₂Cl₂/MeOH to afford 570 mg of the title compound (84% yield).

$^1$H NMR (300 MHz, CDCl₃, 23° C., δ): 9.07 (d, J=2.4 Hz, 1H), 8.20 (d, J=2.1 Hz, 1H), 7.87 (dd, J=10.8 Hz, 7.5 Hz, 1H), 7.66 (d, J=16.2 Hz, 1H), 7.62-7.53 (m, 1H), 7.06 (d, J=7.2 Hz, 1H), 6.93 (d, J=16.2 Hz, 1H), 6.36 (d, J=7.2 Hz, 1H), 4.77 (br s, 1H), 3.43-3.38 (m, 2H), 2.79-2.58 (m, 6H), 1.96-1.85 (m, 2H), 1.81-1.69 (m, 4H). $^{19}$F NMR (282 MHz, CDCl₃, 23° C., δ): −129.1 (m, 1F), −133.6 (m, 1F).

(E)-1-(6,7-difluoroquinolin-3-yl)-7-(5,6,7,8-tetrahydro-1,8-naphthyridin-2-yl)hept-z1-en-3-ol

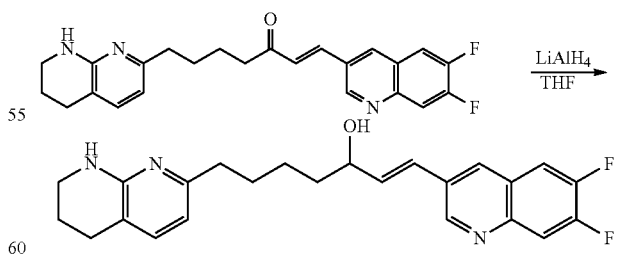

Under nitrogen, to (E)-1-(6,7-difluoroquinolin-3-yl)-7-(5,6,7,8-tetrahydro-1,8-naphthyridin-2-yl)hept-1-en-3-one (1.03 g, 2.53 mmol, 1.00 equiv) in THF (25 mL) at 0° C. was added LiAlH₄ (1.0 M in THF, 2.53 mL, 2.53 mmol, 1.00 equiv). After stirring for 10 min at 0° C., H₂O (96 μL), 15% NaOH aq (96 μL) and H₂O (288 μL) were added sequentially to the reaction mixture. The reaction mixture was warmed to 23° C. and filtered through a pad of CELITE®. The filtrate was concentrated in vacuo and the residue was purified by column chromatography on silica gel eluting with CH$_2$Cl$_2$/MeOH to afford 780 mg of the title compound (75% yield).

$^1$H NMR (300 MHz, CDCl$_3$, 23° C., δ): 8.95 (d, J=2.4 Hz, 1H), 8.00 (d, J=2.1 Hz, 1H), 7.81 (dd, J=10.8 Hz, 7.5 Hz, 1H), 7.52 (d, J=16.2 Hz, 1H), 7.21 (d, J=7.2 Hz, 1H), 6.76 (d, J=16.2 Hz, 1H), 6.48 (dd, J=16.2 Hz, 4.5 Hz, 1H), 6.34 (d, J=7.2 Hz, 1H), 4.48-4.42 (m, 1H), 3.47-3.41 (m, 2H), 2.79-2.67 (m, 4H), 1.97-1.47 (m, 8H). $^{19}$F NMR (282 MHz, CDCl$_3$, 23° C., δ): −132.1 (m, 1F), −135.1 (m, 1F).

3-(6,7-difluoroquinolin-3-yl)-9-(5,6,7,8-tetrahydro-1,8-naphthyridin-2-yl)nonanoic acid (Compound A6)

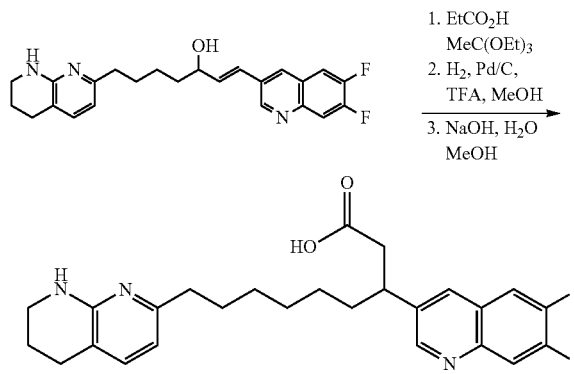

Under nitrogen, to (E)-1-(6,7-difluoroquinolin-3-yl)-7-(5,6,7,8-tetrahydro-1,8-naphthyridin-2-yl)hept-1-en-3-ol (780 mg, 1.90 mmol, 1.00 equiv) in MeC(OEt)$_3$ (19 mL) at 23° C. was added EtCO$_2$H (142 µL, 1.90 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C (127 mg, 0.119 mmol, 6.26 mol %) and H$_2$ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (3.2 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO$_3$ aq (2×5 mL) and dried (MgSO$_4$). The filtrate was concentrated in vacuo and the residue was purified by column chromatography on silica gel eluting with CH$_2$Cl$_2$/MeOH to afford 500 mg of the title compound (58% yield over 3 steps).

$^1$H NMR (300 MHz, CDCl$_3$, 23° C., δ): 8.79 (s, 1H), 7.97 (s, 1H), 7.90-7.81 (m, 1H), 7.58-7.47 (m, 1H), 7.24 (d, J=7.2 Hz, 1H), 6.23 (d, J=7.2 Hz, 1H), 3.48-3.32 (m, 3H), 2.80-2.57 (m, 4H), 1.95-1.20 (m, 14H). $^{19}$F NMR (282 MHz, CDCl$_3$, 23° C., δ): −132.3 (m, 1F), −135.5 (m, 1F).

Example 7. Synthesis of 9-(5,6,7,8-tetrahydro-1,8-naphthyridin-2-yl)-3-(7-(trifluoromethyl)quinolin-3-yl)nonanoic acid (Compound A7)

2-chloro-7-iodoquinoline-3-carbaldehyde

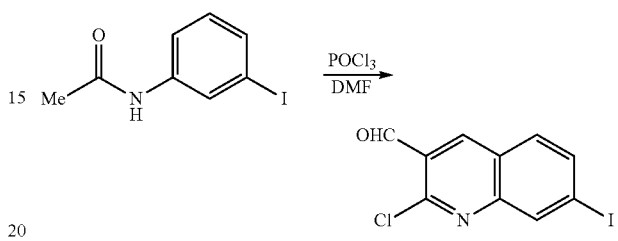

Under nitrogen, to POCl$_3$ (14.9 mL, 160 mmol, 7.00 equiv) at 0° C. was added DMF (4.40 mL, 57.1 mmol, 2.50 equiv). After stirring for 10 min at 0° C., N-(3-iodophenyl)acetamide (5.96 g, 22.8 mmol, 1.00 equiv; Pialat, A. et al., Org. Lett. 2013, 15:1764-1767) was added to the reaction mixture. After stirring for 17 hr at 75° C., the reaction mixture was poured into iced. The phases were separated and the aqueous phase was extracted with CH$_2$Cl$_2$ (3×50 mL). The combined organic phases were washed with brine (100 mL) and dried (MgSO$_4$). The filtrate was concentrated in vacuo and the residue was purified by column chromatography on silica gel eluting with CH$_2$Cl$_2$/MeOH to afford 2.9 g of the title compound (40% yield).

$^1$H NMR (300 MHz, CDCl$_3$, 23° C., δ): 10.55 (s, 1H), 8.72 (s, 1H), 8.52 (s, 1H), 7.93 (dd, J=8.4 Hz, 1.5 Hz, 1H), 7.69 (d, J=8.4 Hz, 1H).

2-chloro-7-(trifluoromethyl)quinoline-3-carbaldehyde

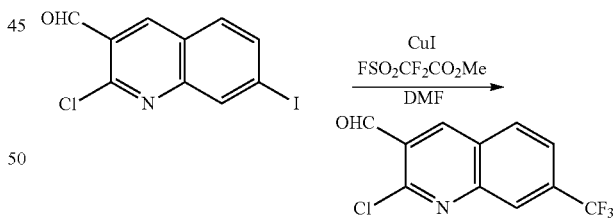

Under nitrogen, to 2-chloro-7-iodoquinoline-3-carbaldehyde (2.90 g, 9.13 mmol, 1.00 equiv) in DMF (18 mL) at 23° C. was added CuI (4.35 g, 22.8 mmol, 2.50 equiv) and FSO$_2$CF$_2$CO$_2$Me (11.6 mL, 91.3 mmol, 10.0 equiv). After stirring for 2 hr at 95° C., the reaction mixture was cooled to 23° C. and filtered through a pad of CELITE®. The filtrate was concentrated in vacuo and the residue was purified by column chromatography on silica gel eluting with hexanes/EtOAc to afford 1.5 g of the title compound (63% yield).

$^1$H NMR (300 MHz, CDCl$_3$, 23° C., δ): 10.60 (s, 1H), 8.82 (s, 1H), 8.39 (s, 1H), 8.14 (d, J=8.4 Hz, 1H), 7.84 (d, J=8.4 Hz, 1H). $^{19}$F NMR (282 MHz, CDCl$_3$, 23° C., δ): −63.2 (s, 3F).

7-(trifluoromethyl)quinoline-3-carbaldehyde

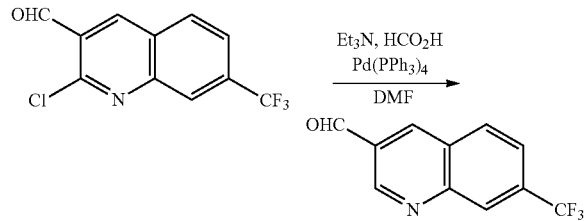

Under nitrogen, to 2-chloro-7-(trifluoromethyl)quinoline-3-carbaldehyde (1.50 g, 5.78 mmol, 1.00 equiv) in DMF (5.8 mL) at 23° C. was added triethylamine (9.67 mL, 69.4 mmol, 12.0 equiv), Pd(PPh$_3$)$_4$ (334 mg, 0.289 mmol, 5.00 mol %), and formic aid (1.18 mL, 31.2 mmol, 5.40 equiv). After stirring for 1 hr at 100° C., the reaction mixture was cooled to 23° C. and water (30 mL) and EtOAc (20 mL) was added. The phases were separated and the aqueous phase was extracted with EtOAc (3×20 mL). The combined organic phases were washed with brine (50 mL) and dried (MgSO$_4$). The filtrate was concentrated in vacuo and the residue was purified by column chromatography on silica gel eluting with hexanes/EtOAc to afford 412 mg of the title compound (32% yield).

$^1$H NMR (300 MHz, CDCl$_3$, 23° C., δ): 10.32 (s, 1H), 9.48 (d, J=1.5 Hz, 1H), 8.71 (d, J=1.5 Hz, 1H), 8.51 (s, 1H), 8.15 (d, J=8.4 Hz, 1H), 7.86 (d, J=8.4 Hz, 1H). $^{19}$F NMR (282 MHz, CDCl$_3$, 23° C., δ): −63.1 (s, 3F).

(E)-7-(5,6,7,8-tetrahydro-1,8-naphthyridin-2-yl)-1-(7-(trifluoromethyl)quinolin-3-yl)hept-1-en-3-one

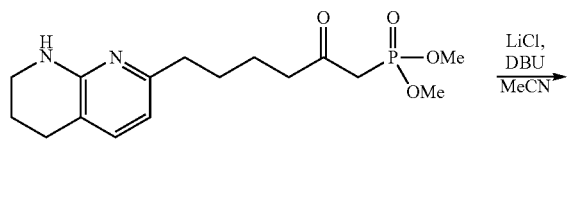

Under nitrogen, to dimethyl (2-oxo-6-(5,6,7,8-tetrahydro-1,8-naphthyridin-2-yl)hexyl)phosphonate (685 mg, 2.01 mmol, 1.10 equiv) in MeCN (9 mL) at 23° C. was added 7-(trifluoromethyl)quinoline-3-carbaldehyde (412 mg, 1.83 mmol, 1.00 equiv), LiCl (77.6 mg, 1.83 mmol, 1.00 equiv) and DBU (0.287 mL, 1.92 mmol, 1.05 equiv). After stirring for 1 hr at 75° C., the reaction mixture was cooled to 23° C. and was filtered through a pad of CELITE®. The filtrate was concentrated in vacuo and the residue was purified by column chromatography on silica gel eluting with CH$_2$Cl$_2$/MeOH to afford 706 mg of the title compound (88% yield).

$^1$H NMR (300 MHz, CDCl$_3$, 23° C., δ): 9.19 (d, J=2.4 Hz, 1H), 8.42 (d, J=2.1 Hz, 1H), 8.31 (d, J=2.1 Hz, 1H), 8.00 (d, J=9.0 Hz, 1H), 7.79 (d, J=9.0 Hz, 1H), 7.69 (d, J=16.2 Hz, 1H), 7.04 (d, J=7.2 Hz, 1H), 6.99 (d, J=16.2 Hz, 1H), 6.37 (d, J=7.2 Hz, 1H), 4.78 (br s, 1H), 3.41-3.37 (m, 2H), 2.80-2.58 (m, 6H), 1.93-1.85 (m, 2H), 1.81-1.69 (m, 4H). $^{19}$F NMR (282 MHz, CDCl$_3$, 23° C., δ): −62.8 (s, 3F).

(E)-7-(5,6,7,8-tetrahydro-1,8-naphthyridin-2-yl)-1-(7-(trifluoromethyl)quinolin-3-yl)hept-1-en-3-ol

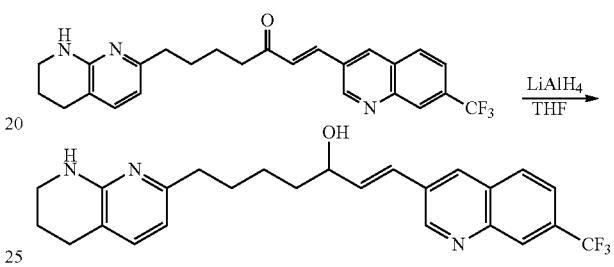

Under nitrogen, to (E)-7-(5,6,7,8-tetrahydro-1,8-naphthyridin-2-yl)-1-(7-(trifluoromethyl)quinolin-3-yl)hept-1-en-3-one (705 mg, 1.60 mmol, 1.00 equiv) in THF (16 mL) at 0° C. was added LiAlH$_4$ (1.0 M in THF, 1.60 mL, 1.60 mmol, 1.00 equiv). After stirring for 10 min at 0° C., H$_2$O (54 μL), 15% NaOH aq (54 μL) and H$_2$O (162 μL) were added sequentially to the reaction mixture. The reaction mixture was warmed to 23° C. and filtered through a pad of CELITE®. The filtrate was concentrated in vacuo and the residue was purified by column chromatography on silica gel eluting with CH$_2$C$_2$/MeOH to afford 515 mg of the title compound (73% yield).

$^1$H NMR (300 MHz, CDCl$_3$, 23° C., δ): 9.08 (d, J=2.4 Hz, 1H), 8.37 (d, J=2.1 Hz, 1H), 8.08 (d, J=2.1 Hz, 1H), 7.91 (d, J=9.0 Hz, 1H), 7.71 (d, J=9.0 Hz, 1H), 7.06 (d, J=7.2 Hz, 1H), 6.79 (d, J=16.2 Hz, 1H), 6.53 (dd, J=16.2 Hz, 4.5 Hz, 1H), 6.34 (d, J=7.2 Hz, 1H), 4.89 (br s, 1H), 4.48-4.40 (m, 1H), 3.43-3.37 (m, 2H), 2.75-2.57 (m, 4H), 1.97-1.42 (m, 8H). $^{19}$F NMR (282 MHz, CDCl$_3$, 23° C., δ): −62.6 (s, 3F).

9-(5,6,7,8-tetrahydro-1,8-naphthyridin-2-yl)-3-(7-(trifluoromethyl)quinolin-3-yl)nonanoic acid (Compound A7)

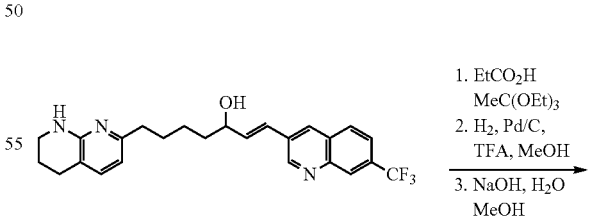

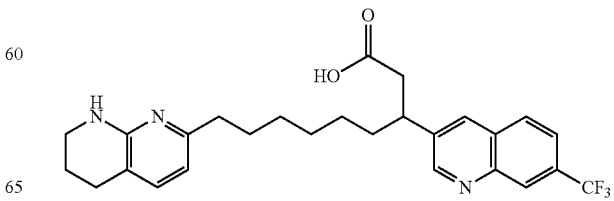

Under nitrogen, to (E)-7-(5,6,7,8-tetrahydro-1,8-naphthyridin-2-yl)-1-(7-(trifluoromethyl)quinolin-3-yl)hept-1-en-3-ol (515 mg, 1.17 mmol, 1.00 equiv) in MeC(OEt)$_3$ (12 mL) at 23° C. was added EtCO$_2$H (87.3 μL, 1.17 mmol, 1.00 equiv). After stirring for 2 hr at 140° C., the reaction mixture was directly loaded on silica gel and purified by column chromatography on silica gel eluting with hexanes/EtOAc to afford a crude rearrangement product, which was used in the next step without further purification.

Under air, to the above obtained residue in MeOH-TFA (10 mL-1 mL) at 23° C. was added 10% Pd/C 66.6 mg, 0.0626 mmol, 5.35 mol %) and H$_2$ was introduced with a balloon. After stirring for 1 hr at 23° C., the reaction mixture was filtered through a pad of CELITE®. The filtrate was concentrated in vacuo to afford a crude olefin reduction product, which was used in the next step without further purification.

Under air, to the above obtained residue in MeOH (10 mL) at 23° C. was added 15% NaOH aq (4.4 mL). After stirring for 20 min at 60° C., the reaction mixture was neutralized with 3N HCl and concentrated in vacuo to remove MeOH. The residual aqueous solution was extracted with EtOAc (3×10 mL) and the combined organic phases were washed with NaHCO$_3$ aq (2×5 mL) and dried (MgSO$_4$). The filtrate was concentrated in vacuo and the residue was purified by column chromatography on silica gel eluting with CH$_2$C$_2$/MeOH to afford 300 mg of the title compound (53% yield over 3 steps).

$^1$H NMR (300 MHz, CDCl$_3$, 23° C., δ): 8.93 (s, 1H), 8.40 (s, 1H), 8.03 (s, 1H), 7.91 (d, J=9.0 Hz, 1H), 7.70 (d, J=9.0 Hz, 1H), 7.24 (d, J=7.2 Hz, 1H), 6.23 (d, J=7.2 Hz, 1H), 3.48-3.40 (m, 3H), 2.80-2.59 (m, 4H), 1.95-1.20 (m, 14H). $^{19}$F NMR (282 MHz, CDCl$_3$, 23° C., δ): −62.7 (s, 3F).

Example 8. Synthesis of (S)-3-(6-(difluoromethoxy)pyridin-3-yl)-3-(2-oxo-3-((3-((5,6,7,8-tetrahydro-1,8-naphthyridin-2-yl)methyl)oxetan-3-yl)methyl)imidazolidin-1-yl)propanoic acid The synthetic route is the same as Example 1 except for substituting at Step-8: (3-((5,6,7,8-tetrahydro-1,8-naphthyridin-2-yl)methyl)oxetan-3-yl)methanamine for compound 6b and continuing the synthetic scheme using the same reaction conditions.

Example 9. Synthesis of (S)-3-(3-(2,2-difluoro-3-(5,6,7,8-tetrahydro-1,8-naphthyridin-2-yl)propyl)-2-oxoimidazolidin-1-yl)-3-(6-(difluoromethoxy)pyridin-3-yl)propanoic acid

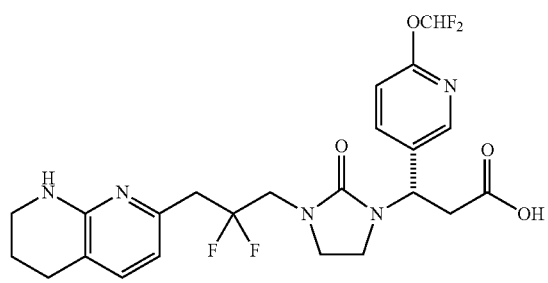 [SMILES: O=C(O)C[C@@H](c1ccc(OC(F)F)nc1)N1CCN(CC(F)(F)Cc2ccc3c(n2)NCCC3)C1=O]

The synthetic route is the same as Example 1 except for substituting at Step-8: 2,2-difluoro-3-(5,6,7,8-tetrahydro-1,8-naphthyridin-2-yl)propan-1-amine for compound 6b and continuing the synthetic scheme using the same reaction conditions.

The synthesis of 2,2-difluoro-3-(5,6,7,8-tetrahydro-1,8-naphthyridin-2-yl)propan-1-amine is performed as shown in Scheme 3.

Example 10. Synthesis of (S)-3-(3-(2,2-difluoro-3-(5,6,7,8-tetrahydro-1,8-naphthyridin-2-yl)propyl)-2-oxoimidazolidin-1-yl)-3-(6-methoxypyridin-3-yl)propanoic acid

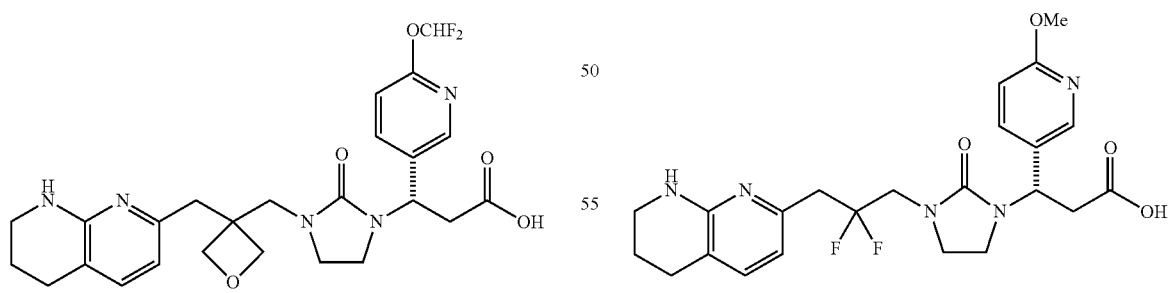

The synthetic scheme is the same as Example 9, except the synthesis in Step 1 uses sodium 2-chloroacetate instead of sodium 2-chloro-2,2-difluoroacetate. The synthesis proceeds under the same conditions as Example 3.

Example 10-1

Scheme 3

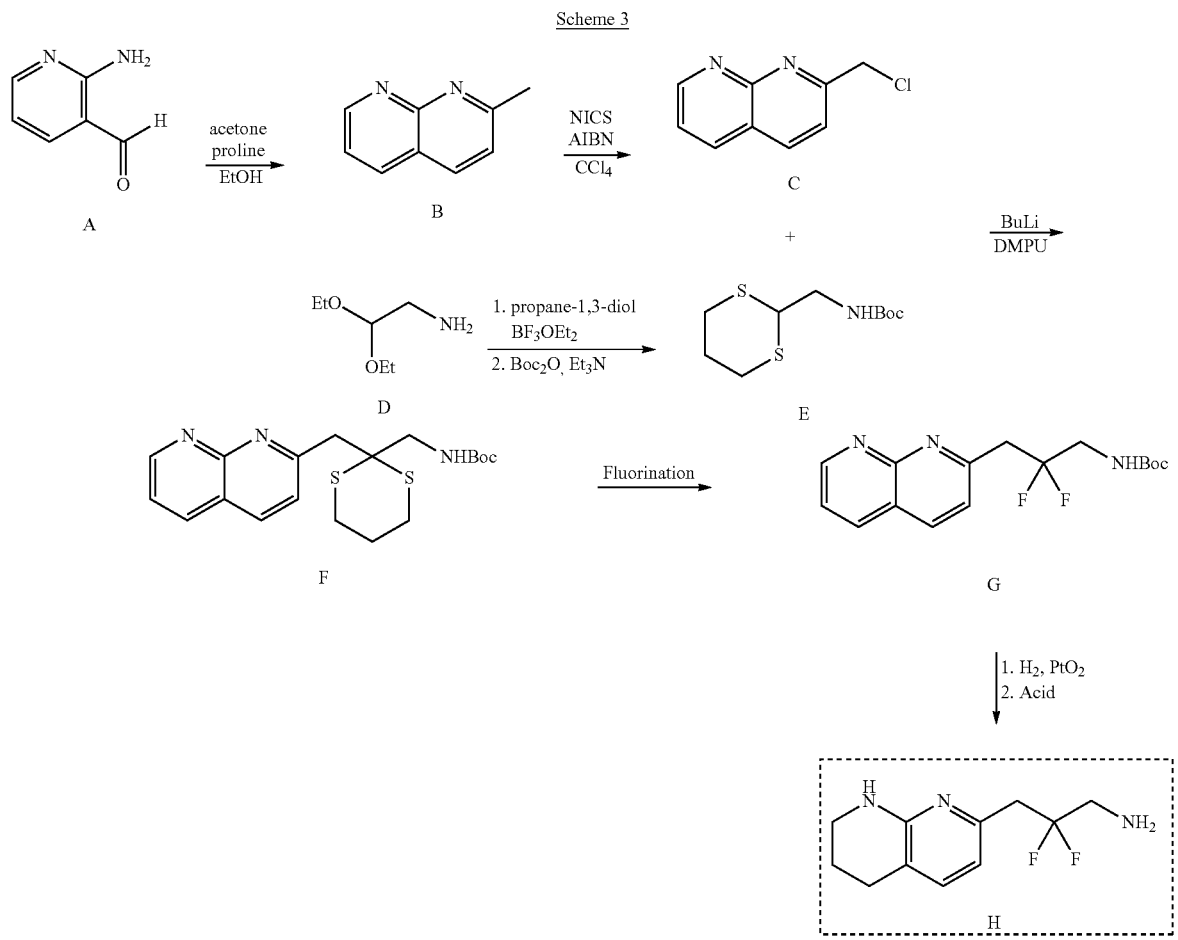

The preparation of intermediates C and E is detailed in the literature and is depicted above (for C; WO2011150156 and for E; Seebach, D. et al., *Liebigs Ann. Chem.*, 1994, 701-717). The formation of the dianion of E has been described, and it was used to displace substituted benzylic chlorides (Bradshaw, B. et al., *Org. Biomol. Chem.*, 2008, 6:2138-2157). This event similarly affords complex dithiane F. Fluorodesulfurization of thioketals has been described with several reagents (Sondej, S. C. et al., *J. Org. Chem.*, 1986, 51:3508-13.); intermediate G is reduced and deprotected as described in the literature (US20040038963). Fragment H is inserted into the known route to produce the target compounds.

Example 11. Testing of the Compounds of Present Invention in Cell Adhesion Assays The ability of compounds to block adhesion of three primary cell cultures: human dermal microvascular endothelial (HMVEC), rat lung microvascular endothelial (RLMVEC), and rabbit aortic endothelial (RAEC) cells, to vitronectin coated plates was determined using the following procedure. This test demonstrates inhibition of the interaction of αv integrin on the cell surface with the ligand, vitronectin.

Adhesion Plates Preparation.

96-well plates were coated with vitronectin in PBS, pH 7.4 by incubating 50 μL of the solution (10 μg/ml) for 1.5 h at room temperature or overnight at 4° C. The plates then were blocked with 1% BSA in PBS (30 min at room temperature) and washed with PBS.

Cell Culturing and Loading.

HMVEC cells (passages (p) 9-14) (from Lonza, Allendale, N.J.) RLMVEC cells (p4-14) (from Vec Technology, Rensselaer, N.Y.) and RAEC cells (p4-14) (from CellBiologics, Chicago, Ill.) were used for the compound testing. Cells were grown in T175 tissue culture flasks and dislodged by gentle 3 min treatment with Accutase (Life Technologies). After washing, the cells in suspension in RPMI-1640 (Life Technologies) were loaded with calcein-AM (5 μM) (Life Technologies) for 30 min at 37° C. and re-suspended into RPMI w/o phenol red medium containing 10% FBS.

Adhesion Assay.

The cell suspension was aliquoted into the wells at a density of $1.0 \times 10^5$ cells/well (RLMVEC) and $5.0 \times 10^4$ (HMVEC, and RAEC). The test compounds are added at the same time with the cells. The plates are incubated for 1.5 h at 37° C. The cells that did not adhere during this incubation were removed by gentle washing. The wash was performed by 2 cycles of aspiration of the supernatant and addition of 100 μL of the pre-warmed fresh DPBS (Life Technologies). A fluorescence of the remaining cells is measured using a multimode plate reader (Victor 2V, PerkinElmer) at an excitation/emission wavelengths of 485/535 nm. The compounds were tested starting with maximal concentration of 1 μM with half-log dilution schedule. $IC_{50}$ values were calculated with Prism 5 (GraphPad, CA) by fixing the bottom of the curves to a value of blank for empty wells fluorescence.

As shown in Table 2, all the fluorinated αv antagonists are active in inhibiting cellular adhesion to vitronectin through the αv integrin. Non-fluorinated reference antagonist, L-845704, is shown for comparison.

TABLE 2

Potencies of test compounds to block adhesion of different cell cultures to vitronectin.

| Compound # | IC50 (M) | | |
|---|---|---|---|
| | HMVEC | RLMVEC | RAEC |
| L-845704 | 2.5E−08 | 5.5E−09 | 1.0E−08 |
| A1 | 9.4E−09 | 3.1E−08 | 8.4E−09 |
| A2 | 1.6E−07 | 6.8E−08 | 1.6E−08 |
| A3 | 6.2E−07 | 2.3E−07 | 5.9E−08 |
| A4 | 4.2E−08 | 3.2E−08 | 8.5E−09 |
| A5 | 2.5E−07 | 3.7E−08 | 2.0E−08 |
| A6 | 4.4E−08 | 5.5E−09 | 4.4E−08 |
| A7 | 1.3E−07 | 4.0E−07 | 2.1E−07 |

Example 12. Anti-Angiogenic Activity Using Chick Chorioallantoic Membrane (CAM) Assay CAM surfaces were grafted with gelatin sponges impregnated with the concentrations of test compounds and 50 ng VEGF dissolved in PBS. Untreated CAM received only VEGF and PBS. Error bars represent SEM, N=5, P values for the treated groups were calculated by comparing with the untreated group (*p<0.05, p<0.01, *p<0.001).

Test Substance Preparation:

Test samples and standards were dissolved in PBS and sterilized by passing through a syringe filter (0.22 μm). hVEGF(SIGMA) 50 ng/μl was prepared in sterile PBS.

Grafting:

Gelatin sponge (Abogel) was cut in approximately 2 mm³ pieces and loaded with required test substance or PBS and VEGF. The graft was placed on the CAM.

Eggs:

Fertile hen eggs were procured from a hatchery and were cleaned and decontaminated using alcohol. 1 ml of albumin was removed using a syringe and incubated for 8 days. Grafts were placed on developing CAMs and further incubated to day 12. On day 12, CAMs were fixed with 4% formaldehyde in PBS, dissected and imaged.

Imaging:

Fixed CAMs were imaged under constant illumination and magnification under a stereomicroscope fitted with a digital camera (CANON).

Image Analysis:

Images were analyzed on MS PowerPoint keeping the image size constant. A ring was drawn around the graft and the size was kept constant. Blood vessels crossing the ring were counted for each test group.

Statistical Analysis:

Data were analyzed on MSExcel 2007.

As shown in FIG. 1, Compounds A1 and A2 each shows anti-angiogenic activity in the chick CAM assay, and significantly decreases the number of blood vessels, as compared to the untreated control.

Example 13. Distribution in Plasma, Aqueous Humor, Vitreous Humor, and Retina after Topical Ocular Administration in Dutch Belted Rabbits The plasma concentrations and ocular distribution (aqueous humor, vitreous humor, and retina) of Compounds A1, A2, and A3 were determined following topical ocular administration in Dutch Belted rabbits. The test compounds were administered in each eye at a volume of 50 μL/eye at a concentration of 1.0-2.5 mg/mL (compound A2, 1.0 mg/mL; compounds A1 and A3 at 2.5 mg/mL). Plasma and different ocular tissue samples were collected at pre-determined time points (1.0 and 8.0 hours for compound A1; 0.5 and 8 hours for compounds A2 and A3). Aqueous humor, vitreous humor, and retina were collected from each eye at each time point post-dose. Also, weights were recorded. Plasma and ocular sample concentrations of the compounds were determined by LC-MS/MS.

Animal Dosing:

The exposure of compounds A1, A2, and A3 was evaluated in Dutch Belted rabbits. The study was not blinded. Each compound was dosed as n=3/time point for a total of nine rabbits. Rabbits were housed one per cage. Animals were not fasted, and food and water were supplied ad libitum.

Animals were anesthetized following the 13IA5 IACUC protocol for the dosing. Each rabbit received a bolus dose of test formulation via topical ocular administration into both eyes at time zero on the day of dosing. Plasma and ocular samples were collected at pre-determined time points. Animals for the 30-minute and 1-hour time points were anesthetized for the entire duration of the study. The animals for the 8-hour time point were recovered after dosing and then euthanized for sampling purposes.

At each time point, approximately 0.5 mL of blood was collected and placed into chilled Na-heparin tubes containing citric acid. Blood samples were centrifuged at a speed of 3,000 g for 5 minutes to obtain plasma as quickly as possible. Samples were stored frozen at −80° C. until analysis. Animals were euthanized per the 13IA5 IACUC protocol and both eyes were enucleated immediately. Following enucleation, each eye was rinsed with PBS. Ocular samples from both eyes of each animal were collected and weights were recorded. All the samples were frozen immediately on dry ice, and stored at −60 to −80° C. for analysis.

Analysis of Plasma and Ocular Samples:

An LC-MS/MS method was developed for the determination of Compounds A1, A2, and A3 in rabbit plasma and ocular samples. A pre-study standard curve was analyzed to determine the specificity, range, and lower limit of quantitation of the method.

Figure 2:
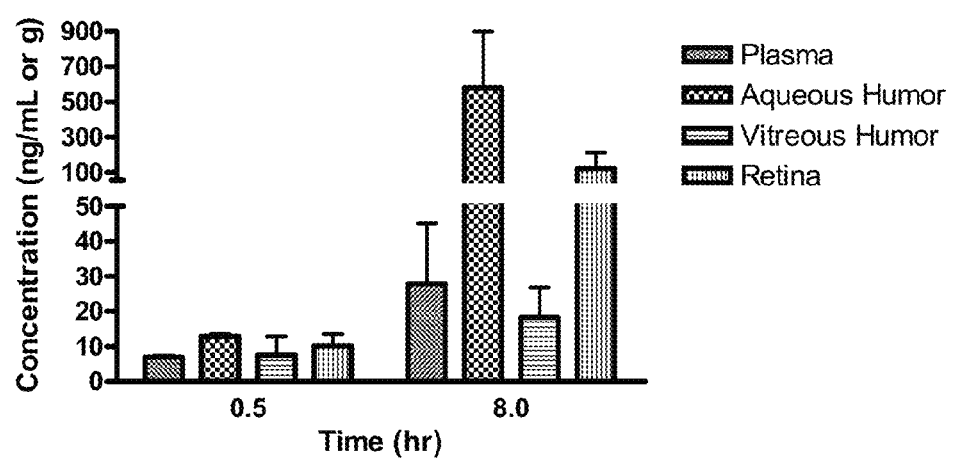
Figure 3:
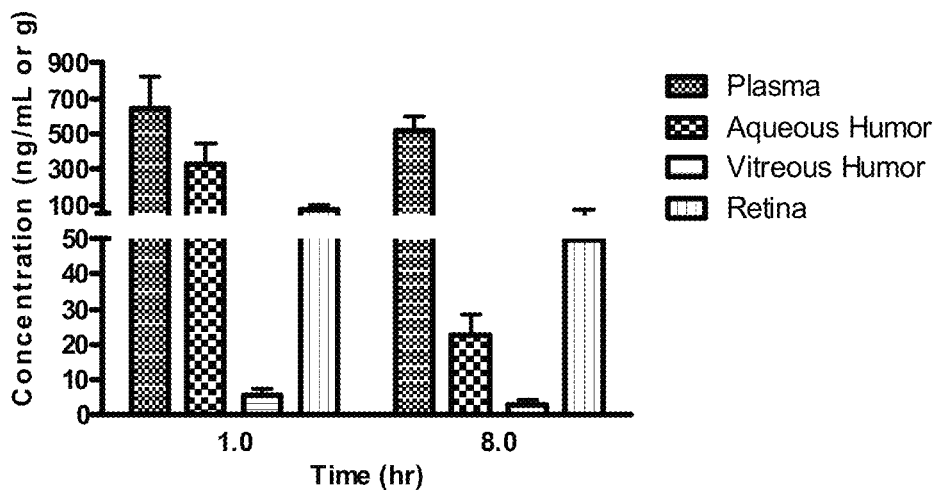
Figure 4:
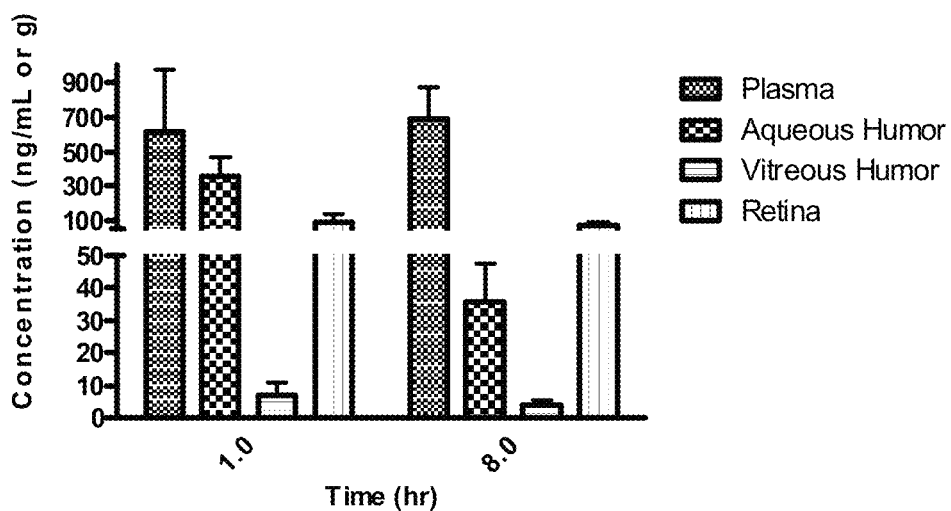

As shown in FIGS. 2, 3, and 4, Compounds A1, A2, and A3 are each efficiently distributed to the retina.

The following examples of ophthalmic formulations are given by way of illustration:

Example 14. Ophthalmic Formulation of Compound A1

| Solution Composition | I | II | III |
|---|---|---|---|
| Compound A1 | 2.5 g | 2.0 | 1.0 |
| β-cyclodextrin sulfobutyl ether | 10 g | 10 g | 5 g |
| Boric acid | 1.05 g | 1.05 g | 1.05 g |
| Disodium tetraborate | 0.285 g | 0.285 g | 0.285 g |
| Sodium Chloride | 0.25 g | 0.25 g | 0.25 g |
| Edetate disodium | 2.5 mg | 2.5 mg | 2.5 mg |
| Propylaminopropyl biguanide | 0.03 mg | 0.03 mg | 0.03 mg |
| Water for injection q.s. | 100 ml | 100 ml | 100 ml |

The active compounds were added to a solution of borate buffered saline containing the β-cyclodextrin sulfobutyl ether, edetate disodium, and propylamino biguanidate dissolved in sterile water for injection in a tared sterile vessel. The pH of the solution was adjusted to 7.5 by the addition of hydrochloric acid. The composition is sterilized by filtration through a 0.45 micron filter.

Example 15. Ophthalmic Formulation of Compound A1

| Solution Composition | I | II | III |
|---|---|---|---|
| Compound A1 | 2.5 g | 2.0 | 1.0 |
| Hyrdoxypropyl β-cyclodextrin | 10 g | 10 g | 5 g |
| Boric acid | 1.05 g | 1.05 g | 1.05 g |
| Disodium tetraborate | 0.285 g | 0.285 g | 0.285 g |
| Sodium Chloride | 0.25 g | 0.25 g | 0.25 g |
| Edetate disodium | 2.5 mg | 2.5 mg | 2.5 mg |
| Propylaminopropyl biguanide | 0.03 mg | 0.03 mg | 0.03 mg |
| Water for injection q.s. | 100 ml | 100 ml | 100 ml |

The active compounds were added to a solution of borate buffered saline containing the hydroxylpropyl-β-cyclodextrin, edetate disodium, and propylamino biguanidate dissolved in sterile water for injection in a tared sterile vessel. The pH of the solution was adjusted to 7.5 by the addition of hydrochloric acid. The composition is sterilized by filtration through a 0.45 micron filter.

Example 16. Ophthalmic Formulation of Compound A2

| Solution Composition | I | II | III |
|---|---|---|---|
| Compound A2 | 2.0 g | 1.5 | 1.0 |
| β-cyclodextrin sulfobutyl ether | 10 g | 10 g | 5 g |
| Boric acid | 1.05 g | 1.05 g | 1.05 g |
| Disodium tetraborate | 0.285 g | 0.285 g | 0.285 g |
| Sodium Chloride | 0.25 g | 0.25 g | 0.25 g |
| Edetate disodium | 2.5 mg | 2.5 mg | 2.5 mg |
| Propylaminopropyl biguanide | 0.03 mg | 0.03 mg | 0.03 mg |
| Water for injection q.s. | 100 ml | 100 ml | 100 ml |

The active compounds were added to a solution of borate buffered saline containing the β-cyclodextrin sulfobutyl ether, edetate disodium, and propylamino biguanidate dissolved in sterile water for injection in a tared sterile vessel. The pH of the solution was adjusted to 7.5 by the addition of hydrochloric acid. The composition is sterilized by filtration through a 0.45 micron filter.

Example 17. Ophthalmic Formulation of Compound A3

| Solution Composition | I | II | III |
|---|---|---|---|
| Compound A3 | 2.5 g | 2.0 | 1.0 |
| β-cyclodextrin sulfobutyl ether | 10 g | 10 g | 5 g |
| Boric acid | 1.05 g | 1.05 g | 1.05 g |
| Disodium tetraborate | 0.285 g | 0.285 g | 0.285 g |
| Sodium Chloride | 0.25 g | 0.25 g | 0.25 g |
| Edetate disodium | 2.5 mg | 2.5 mg | 2.5 mg |
| Propylaminopropyl biguanide | 0.03 mg | 0.03 mg | 0.03 mg |
| Water for injection q.s. | 100 ml | 100 ml | 100 ml |

The active compounds were added to a solution of borate buffered saline containing the β-cyclodextrin sulfobutyl ether, edetate disodium, and propylamino biguanidate dissolved in sterile water for injection in a tared sterile vessel. The pH of the solution was adjusted to 7.5 by the addition of hydrochloric acid. The composition is sterilized by filtration through a 0.45 micron filter.

Example 18. Evaluation of the Safety and Efficacy of Topically Applied Test Compounds in the Laser-Induced Choroidal Neovascularization (CNV) Model in Dutch Belted Rabbits Healthy male animals weighing between 1.5 and 2.0 kg were used in these studies. Animals were weighed prior to dosing and at euthanasia, and more often if needed. Baseline fundus photography and fluorescein angiography was performed on each animal prior to CNV induction.

Animals were anesthetized with an intramuscular injection of ketamine hydrochloride (20 mg/kg) and xylazine (2 mg/kg) for CNV induction, fundus photography, fluorescein angiography, and intravitreal (IVT) injections. Rabbits were maintained on isoflurane (approximately 1 to 3%) in oxygen (approximately 1 to 2 L/min) as necessary. One drop of topical proparacaine hydrochloride anesthetic (0.5%) was placed in each eye before procedures. Additional topical ocular anesthesia was utilized during the procedure if needed.

CNV was induced by laser photocoagulation treatment. An external diode laser was applied to the retina using a laser contact lens and a slit lamp biomicroscope. On Day 1, both eyes of each animal underwent laser photocoagulation treatment using the following laser settings:
Number of Spots: 12-15 spots per eye
Power Range: 50-200 mW
Spot Size: 20-100 μm
Time: 0.05-0.1 seconds Following laser treatment, 50 μL of a 25-μg/mL VEGF solution (1.25 μg dose) was intravitreally injected into each eye. Daily gross ocular exams were performed throughout the study period.

Clinical ophthalmic exams (slit-lamp biomicroscopy and indirect ophthalmoscopy), fundus photography, and fluorescein angiography were performed at baseline and then weekly for up to 6 weeks post-induction. Exams were scored using the McDonald-Shadduck Score System. Optical Coherence Tomography OCT imaging was performed weekly for diagnostic imaging during the exams.

On the last day of the study, blood sampling was performed just prior to administration of the AM dose and at 2 hours post dosing. Blood samples were centrifuged at a speed of 3,000 g for 5 minutes to obtain plasma as quickly as possible. Samples were stored frozen at −80° C. until analysis. At the conclusion of the study, animals were euthanized per the 13C232Q3 IACUC protocol and both eyes enucleated immediately. Following enucleation, each eye was rinsed with phosphate-buffered saline. Ocular samples (aqueous humor, vitreous humor retina and choroid) from both eyes of each animal were collected and weights were recorded. All the samples were frozen immediately on dry ice, and stored at −60 to −80° C. for analysis.

Figure 5:
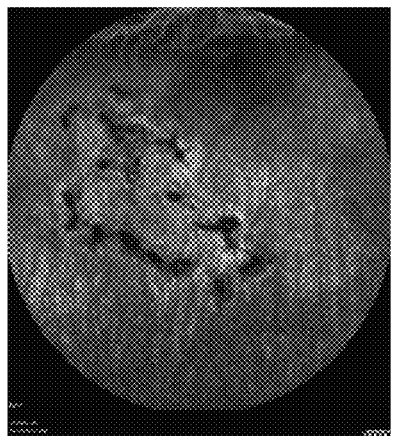
Figure 5:
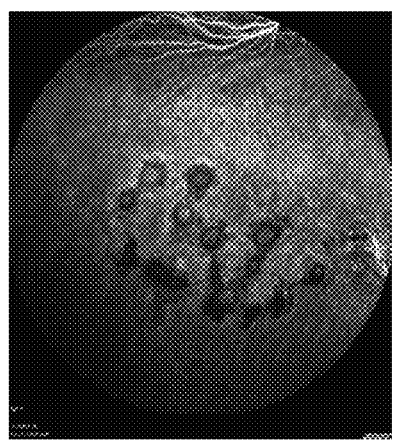
Figure 5:
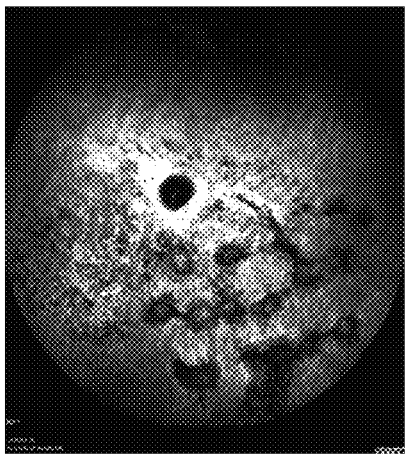

As shown in FIG. 5, Compound A1 or Compound A2 effectively reduced laser-induced choroidal neovascularization, as compared to the vehicle control.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A method of treating or preventing a disease or condition selected from the group consisting of macular degeneration, diabetic retinopathy (DR), macular edema, diabetic macular edema (DME), and macular edema following retinal vein occlusion (RVO) in a subject, comprising administering to a subject in need thereof a therapeutically effective amount of a compound of formula I:

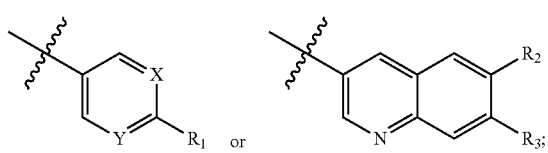

(I)

or a pharmaceutically acceptable salt or solvate thereof, wherein:

Z is

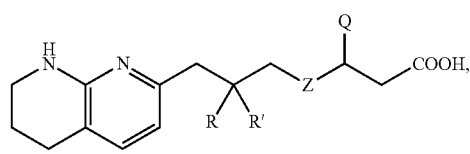

R and R' are each independently H or F, or R and R', together with the carbon atom to which they are attached, form a 3- or 4-membered carbocyclic or heterocyclic ring;

Q is

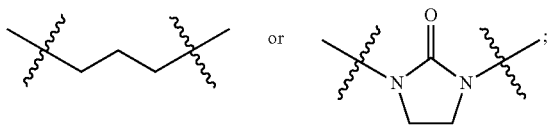 [SMILES: *CCC* ; *N1CCN(*)C1=O]

X is CH or N;

Y is CH or N;

$R_1$ is $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms; and $R_2$ and $R_3$ are each independently H, F, $CH_2F$, $CHF_2$, or $CF_3$, provided that one of $R_2$ and $R_3$ is not H, provided that the compound of formula I contains at least one fluorine atom.

2. The method of claim 1, wherein R and R' are each H.

3. The method of claim 1, wherein Q is

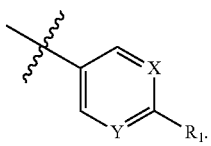

4. The method of claim 3, wherein X is N and Y is CH.

5. The method of claim 3, wherein X and Y are each CH.

6. The method of claim 3, wherein X and Y are each N.

7. The method of claim 3, wherein $R_1$ is straight chain $C_1$-$C_4$ or branched $C_3$-$C_4$ alkyl, and is substituted with 1, 2, 3, 4, 5, 6, 7, 8, or 9 fluorine atoms.

8. The method of claim 3, wherein $R_1$ is methyl substituted with 1, 2, or 3 fluorine atoms.

9. The method of claim 3, wherein $R_1$ is straight chain $C_1$-$C_6$ or branched $C_3$-$C_6$ alkoxy, and is substituted with 0, 1, 2, 3, 4, 5, 6, or 7 fluorine atoms.

10. The method of claim 9, wherein $R_1$ is methoxy substituted with 0, 1, 2, or 3 fluorine atoms.

11. The method of claim 3, wherein Z is

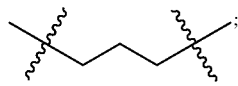 [SMILES: *CCC*]

R and R' are each H; and $R_1$ is methyl substituted with 1, 2, or 3 fluorine atoms or methoxy substituted with 0, 1, 2, or 3 fluorine atoms.

12. The method of claim 11, wherein X is N and Y is CH; and $R_1$ is $OCHF_2$.

13. The method of claim 11, wherein X and Y are each N; and $R_1$ is $CF_3$.

14. The method of claim 3, wherein Z is

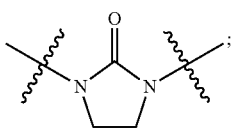 [SMILES: *N1CCN(*)C1=O]

R and R' are each H; X is N and Y is CH; and $R_1$ is methoxy substituted with 0, 1, 2, or 3 fluorine atoms.

15. The method of claim 1, wherein the compound of formula I is of formula II:

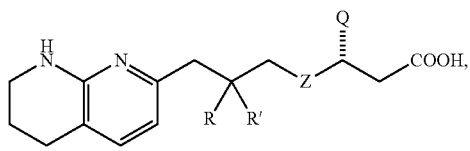

(II)

or a pharmaceutically acceptable salt or solvate thereof.

16. The method of claim 1, wherein the compound of formula I is selected from the group consisting of:

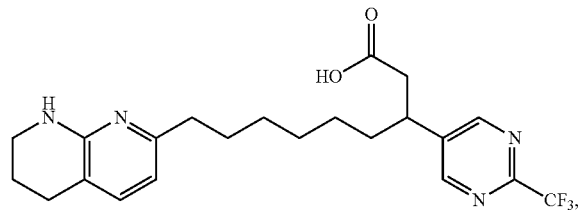

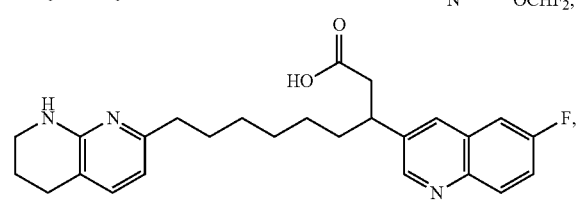

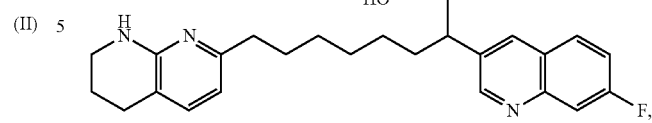

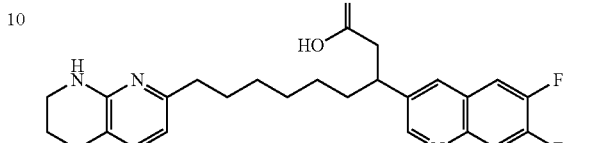

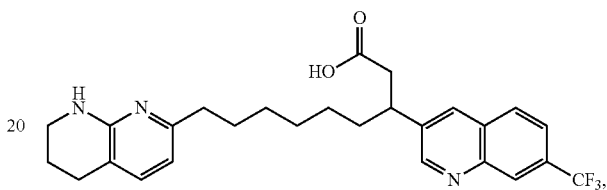

or a pharmaceutically acceptable salt or solvate thereof.

17. The method of claim 1, wherein the αv integrin is an αvβ3 or αvβ5 integrin.

18. The method of claim 1, further comprising administering a second therapy.

19. The method of claim 18, wherein the second therapy comprises administering an agent selected from the group consisting of a) an antagonist of integrin α5β1, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof.

\* \* \* \* \*